United States Patent
Dasseux

(10) Patent No.: US 12,220,462 B1
(45) Date of Patent: Feb. 11, 2025

(54) COMPLEXES FOR DELIVERY OF CYCLIC DINUCLEOTIDES

(71) Applicant: ABIONYX PHARMA SA, Balma (FR)

(72) Inventor: Jean-Louis Dasseux, Toulouse (FR)

(73) Assignee: ABIONYX PHARMA SA, Balma (FR)

( * ) Notice: Subject to any disclaimer, the term of this patent is extended or adjusted under 35 U.S.C. 154(b) by 32 days.

(21) Appl. No.: 17/826,633

(22) Filed: May 27, 2022

Related U.S. Application Data

(63) Continuation of application No. 16/275,054, filed on Feb. 13, 2019, now abandoned.

(60) Provisional application No. 62/630,212, filed on Feb. 13, 2018.

(51) Int. Cl.
| | | |
|---|---|---|
| *A61K 47/69* | (2017.01) | |
| *A61K 47/54* | (2017.01) | |
| *A61K 47/64* | (2017.01) | |
| *A61P 37/00* | (2006.01) | |

(52) U.S. Cl.
CPC ........ *A61K 47/6917* (2017.08); *A61K 47/549* (2017.08); *A61K 47/6455* (2017.08); *A61P 37/00* (2018.01)

(58) Field of Classification Search
CPC ............ A61K 47/6917; A61K 47/6455; A61K 47/549; A61P 37/00
USPC ....................................................... 424/450
See application file for complete search history.

(56) References Cited

U.S. PATENT DOCUMENTS

| | | |
|---|---|---|
| 7,592,326 B2 | 9/2009 | Karaolis |
| 7,709,458 B2 | 5/2010 | Karaolis et al. |
| 8,206,750 B2 | 6/2012 | Dasseux et al. |
| 9,724,408 B2 | 8/2017 | Dubsensky, Jr. et al. |
| 2012/0232005 A1 | 9/2012 | Dasseux et al. |
| 2017/0252417 A1* | 9/2017 | Irvine ............... A61P 37/04 |
| 2017/0340658 A1 | 11/2017 | Vernejoul et al. |
| 2019/0046608 A1 | 2/2019 | Dasseux et al. |
| 2019/0048049 A1 | 2/2019 | Dasseux et al. |
| 2019/0161754 A1* | 5/2019 | Hammond ........... C12N 15/115 |

FOREIGN PATENT DOCUMENTS

| | | |
|---|---|---|
| WO | 2014/093936 | 6/2014 |
| WO | 2014/099824 | 6/2014 |
| WO | 2014/189805 | 11/2014 |
| WO | 2015/017652 | 2/2015 |
| WO | 2015/185565 | 12/2015 |
| WO | 2016/096174 | 6/2016 |
| WO | 2016/120305 | 8/2016 |
| WO | 2018/009466 | 1/2018 |
| WO | 2018/060323 | 4/2018 |

OTHER PUBLICATIONS

Bose, et al., An RNA-Based Fluorescent Biosensor for High-Throughput Analysis of the cGAS-cGAMP-STING Pathway, Cell Chemical Biology 12, 2016, pp. 1539-1549.
Bridgeman, et al., Viruses transfer the antiviral second messenger of cGAMP between cells, Science Magazine, Sep. 11, 2015, vol. 249, Issue 6253.
Corrales, et al., Direct Activation of STING in the Tumor Microenvironment Leads to Potent and Systemic Tumor Regression and Immunity, Cell Reports 11, 2015, pp. 1-13.
Derouchey, et al., A comparison of DNA compaction by arginine and lysine peptides: A physical basis for arginine rich protamines, Apr. 30, 2013, 52(17), pp. 3000-3009.
Fu, et al., STING agonist formulated cancer vaccines can cure established tumors resistant to PD-1 blockade, Science Translational Medicine, Apr. 15, 2015, vol. 7, Issue 283.
Gentili, et al., Transmission of innate immune signaling by packaing of cGAMP in viral particles, Science Magazine, Sep. 11, 2015, vol. 349, Issue 6253.
Li et al., Antitumor Activity of cGAMP via Stimulation of cGAS-cGAMP-STING-IRF3 Mediated Innate Immune Response, Sci. Rep. 6: 19049, 2016.
Lemros, et al., Activiation of the Stimulator of Interferon Genes (STING) adaptor attenuates experimental autoimmune encephalitis, J Immunol, Jun. 15, 2014, 192 (12), pp. 5571-5578.
Lemros, et al., STING, nanoparticles, autoimmune disease and cancer: a novel paradigm for immunotherapy?, Expert Rev. Clin. Immunol, 11 (1), 2015, pp. 155-165.
Nelson et al., Control of bacterial exoelectrogenesis by c-AMP-GMP, PNAS, Apr. 28, 2015, vol. 112, No. 17, pp. 5389-5394.
Opoku-Temeng et al., Cyclic dinucleotide (c-di-GMP, c-di-AMP, and cGAMP) signalings have come of age to be inhibited by small molecules, Chem. Commun., 2016, 52, pp. 9327-9342.
Ren, et al., Structural Basis for Molecular Discrimination by a 3',3'-cGAMP Sensing Riboswitch, Cell Reports 11, Apr. 7, 2015, pp. 1-12.

* cited by examiner

*Primary Examiner* — Yih-Horng Shiao
(74) *Attorney, Agent, or Firm* — Biospark Intellectual Property Law

(57) ABSTRACT

Lipid binding protein based complexes for carrying cyclic dinucleotides (CDNs) and uses thereof, pharmaceutical compositions comprising the complexes, and methods of making the complexes.

Figure 1B:
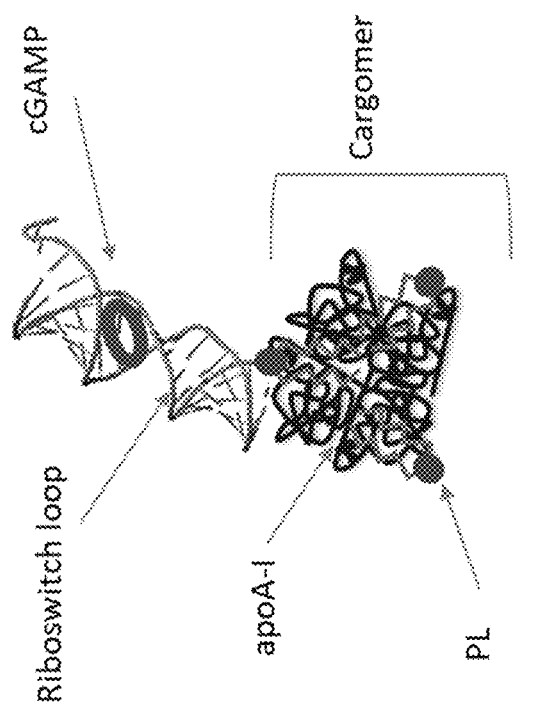

19 Claims, 1 Drawing Sheet
Specification includes a Sequence Listing.

SEQUENCE LISTING

```
<160> NUMBER OF SEQ ID NOS: 26

<210> SEQ ID NO 1
<211> LENGTH: 243
<212> TYPE: PRT
<213> ORGANISM: Homo sapiens

<400> SEQUENCE: 1

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
```

Asn Thr Gln

<210> SEQ ID NO 2
<211> LENGTH: 152
<212> TYPE: RNA
<213> ORGANISM: Artificial Sequence
<220> FEATURE:
<223> OTHER INFORMATION: Exemplary loop forming oligonucleotide

<400> SEQUENCE: 2
gauguaacug aaugaaaugg ugaaggacgg guccaaauag ggaagcaacg aagcauagcc    60
uuuauaugga acacuugggu uauguggagc uacuaguguaa accagcccuu ccuuuuguug    120
aguagagugu gagcuccgua acuaguuaca uc    152

<210> SEQ ID NO 3
<211> LENGTH: 90
<212> TYPE: RNA
<213> ORGANISM: Artificial Sequence
<220> FEATURE:
<223> OTHER INFORMATION: Exemplary loop forming oligonucleotide

<400> SEQUENCE: 3
uccaaauagg gaagcaacga agcauagccu uuauauggaa cacuuggguu auguggagcu    60
acuaguguaa ccagcccuuc cuuuuguuga    90

<210> SEQ ID NO 4
<211> LENGTH: 48
<212> TYPE: RNA
<213> ORGANISM: Artificial Sequence
<220> FEATURE:
<223> OTHER INFORMATION: Exemplary loop forming oligonucleotide

<400> SEQUENCE: 4
aauagggaag caacgaagug gagcuacuag uguaaccagc ccuuccuu    48

<210> SEQ ID NO 5
<211> LENGTH: 59
<212> TYPE: RNA
<213> ORGANISM: Artificial Sequence
<220> FEATURE:
<223> OTHER INFORMATION: Exemplary loop forming oligonucleotide

<400> SEQUENCE: 5
uccaaauagg gaagcaacga aguggagcua cuaguguaac cagcccuucc uuuuguuga    59

<210> SEQ ID NO 6
<211> LENGTH: 52
<212> TYPE: RNA
<213> ORGANISM: Artificial Sequence
<220> FEATURE:
<223> OTHER INFORMATION: Exemplary loop forming oligonucleotide

<400> SEQUENCE: 6
uccaaaaggg aagcaacgaa guggagcuac uaguguaacc agcccuuuug ga    52

<210> SEQ ID NO 7
<211> LENGTH: 44
<212> TYPE: RNA
<213> ORGANISM: Artificial Sequence
<220> FEATURE:
<223> OTHER INFORMATION: Exemplary loop forming oligonucleotide

<400> SEQUENCE: 7

```
aaagggaagc aacgaagugg agcuacuagu guaaccagcc cuuu                44
```

<210> SEQ ID NO 8
<211> LENGTH: 101
<212> TYPE: RNA
<213> ORGANISM: Artificial Sequence
<220> FEATURE:
<223> OTHER INFORMATION: Exemplary loop forming oligonucleotide

<400> SEQUENCE: 8

```
ggguuggugg uaagcgauaa uacuaaacca uucgcgagaa uggggcggaa agccuauagg    60
gucucccuga dacagcgggu ugccgaaaua ucacgcgaua u                       101
```

<210> SEQ ID NO 9
<211> LENGTH: 101
<212> TYPE: RNA
<213> ORGANISM: Artificial Sequence
<220> FEATURE:
<223> OTHER INFORMATION: Exemplary loop forming oligonucleotide

<400> SEQUENCE: 9

```
ggguuggugg uaagcgauaa ugcuaaacca uucgcgagaa uggggcggaa agccuauagg    60
gucucccuga gacagcgggu ugccgaaaua ucacgcgaua u                       101
```

<210> SEQ ID NO 10
<211> LENGTH: 122
<212> TYPE: RNA
<213> ORGANISM: Artificial Sequence
<220> FEATURE:
<223> OTHER INFORMATION: Exemplary loop forming oligonucleotide

<400> SEQUENCE: 10

```
cuccgauauc gacaauacua aaccauccgc gaggguggga cggaaagcua ccaggguguc    60
ucugagacag ccgggaugcc gaaauauacac aauuuuuuuu uuuuuguccc ggcauucuuu    120
uu                                                                   122
```

<210> SEQ ID NO 11
<211> LENGTH: 87
<212> TYPE: RNA
<213> ORGANISM: Artificial Sequence
<220> FEATURE:
<223> OTHER INFORMATION: Exemplary loop forming oligonucleotide

<400> SEQUENCE: 11

```
ucagauacac gacaauacua aaccauccgc gaggauggg cgaaagccua aggucuccc     60 ugagacagcc gggugccgug uaucuga                                       87
```

<210> SEQ ID NO 12
<211> LENGTH: 117
<212> TYPE: RNA
<213> ORGANISM: Artificial Sequence
<220> FEATURE:
<223> OTHER INFORMATION: Exemplary loop forming oligonucleotide

<400> SEQUENCE: 12

```
ggucagauac acgacaauac uaaaccaucc gcgaggaugg ggcggaaagc cuaaggcucu    60
cccugagaca gccgggucgc cgaaauaucu gaacgauauc aggccccggc uuuugu        117
```

<210> SEQ ID NO 13
<211> LENGTH: 84
<212> TYPE: RNA

```
<213> ORGANISM: Artificial Sequence
<220> FEATURE:
<223> OTHER INFORMATION: Exemplary loop forming oligonucleotide

<400> SEQUENCE: 13
gguacacgac aauacuaaac cauccgcgag gaugggcgg aaagccuaag ggucucccug    60
agacagccgg gcugccgaaa uauc                                          84

<210> SEQ ID NO 14
<211> LENGTH: 89
<212> TYPE: RNA
<213> ORGANISM: Artificial Sequence
<220> FEATURE:
<223> OTHER INFORMATION: Exemplary loop forming oligonucleotide

<400> SEQUENCE: 14
ggucacgcac agagcaacca uucgaaagag ugggacgcaa agccuccggc cuaaaccauu    60
gcacuccggu agguagcggu uaccgaugg                                     89

<210> SEQ ID NO 15
<211> LENGTH: 84
<212> TYPE: RNA
<213> ORGANISM: Artificial Sequence
<220> FEATURE:
<223> OTHER INFORMATION: loop forming oligonucleotide

<400> SEQUENCE: 15
gauaucgaca auacuaaacc auccgcgagg gugggacgga aagccuacag ggucucucug    60
agacagccgg gaugccgaaa uauc                                          84

<210> SEQ ID NO 16
<211> LENGTH: 150
<212> TYPE: RNA
<213> ORGANISM: Artificial Sequence
<220> FEATURE:
<223> OTHER INFORMATION: loop forming oligonucleotide

<400> SEQUENCE: 16
gauguaacug aaugaaaugg ugaaggacgg guccaaauag ggaagcaacg aagcauagcc    60
uuuauaugga cacuuggguu auguggagcu acuaguguaa ccggcccucc uuuuguugag   120
uagaguguga gcuccguaac uaguuacauc                                    150

<210> SEQ ID NO 17
<211> LENGTH: 92
<212> TYPE: RNA
<213> ORGANISM: Artificial Sequence
<220> FEATURE:
<223> OTHER INFORMATION: loop forming oligonucleotide

<400> SEQUENCE: 17
ggucacgcac agggcaaacc auucgaaaga gugggacgca agccuccgg ccuaaaccau    60 ugcacuccgg uagguagcgg gguuaccgau gg                                 92

<210> SEQ ID NO 18
<211> LENGTH: 77
<212> TYPE: RNA
<213> ORGANISM: Artificial Sequence
<220> FEATURE:
<223> OTHER INFORMATION: loop forming oligonucleotide

<400> SEQUENCE: 18
aauagggaag caacgaagca uagccuuuau auggacacuu ggguuauguu gagcuacuag    60
```
uguaaccggc ccuccuu                                                          77

<210> SEQ ID NO 19
<211> LENGTH: 20
<212> TYPE: DNA
<213> ORGANISM: Artificial Sequence
<220> FEATURE:
<223> OTHER INFORMATION: Class A CpG oligonucleotide

<400> SEQUENCE: 19 ggggacgat cgtcggggg                                                         20

<210> SEQ ID NO 20
<211> LENGTH: 21
<212> TYPE: DNA
<213> ORGANISM: Artificial Sequence
<220> FEATURE:
<223> OTHER INFORMATION: Class A CpG oligonucleotide

<400> SEQUENCE: 20
ggggacgacg tcgtggggg g                                                      21

<210> SEQ ID NO 21
<211> LENGTH: 24
<212> TYPE: DNA
<213> ORGANISM: Artificial Sequence
<220> FEATURE:
<223> OTHER INFORMATION: Class B CpG oligonucleotide

<400> SEQUENCE: 21
tcgtcgtttt gtcgttttgt cgtt                                                  24

<210> SEQ ID NO 22
<211> LENGTH: 23
<212> TYPE: DNA
<213> ORGANISM: Artificial Sequence
<220> FEATURE:
<223> OTHER INFORMATION: Class B CpG oligonucleotide

<400> SEQUENCE: 22
tcgacgttcg tcgttcgtcg ttc                                                   23

<210> SEQ ID NO 23
<211> LENGTH: 26
<212> TYPE: DNA
<213> ORGANISM: Artificial Sequence
<220> FEATURE:
<223> OTHER INFORMATION: Class B CpG oligonucleotide

<400> SEQUENCE: 23
tcgcgacgtt cgcccgacgt tcggta                                                26

<210> SEQ ID NO 24
<211> LENGTH: 22
<212> TYPE: DNA
<213> ORGANISM: Artificial Sequence
<220> FEATURE:
<223> OTHER INFORMATION: Class C CpG oligonucleotide

<400> SEQUENCE: 24
tcgtcgtttt cggcgcgcgc cg                                                    22

<210> SEQ ID NO 25
<211> LENGTH: 25
<212> TYPE: DNA

```
<213> ORGANISM: Artificial Sequence
<220> FEATURE:
<223> OTHER INFORMATION: Class C CpG oligonucleotide

<400> SEQUENCE: 25
tcgtcgtcgt tcgaacgacg ttgat                                         25

<210> SEQ ID NO 26
<211> LENGTH: 29
<212> TYPE: DNA
<213> ORGANISM: Artificial Sequence
<220> FEATURE:
<223> OTHER INFORMATION: Class C CpG oligonucleotide

<400> SEQUENCE: 26
tcgcgaacgt tcgccgcgtt cgaacgcgg                                     29
```

COMPLEXES FOR DELIVERY OF CYCLIC DINUCLEOTIDES

1. CROSS-REFERENCE TO RELATED APPLICATIONS

The application is a continuation of U.S. application Ser. No. 16/275,054, filed Feb. 12, 2019, which claims the benefit of U.S. provisional application No. 62/630,212, filed Feb. 13, 2018, the contents of which are incorporated herein in their entireties by reference thereto.

2. SEQUENCE LISTING

The instant application contains a Sequence Listing which has been submitted electronically in ASCII format and is hereby incorporated by reference in its entirety. Said ASCII copy, created on Feb. 6, 2019, is named CRN-024US_Seqeunce_Listing_ST25 and is 8,781 bytes in size.

3. BACKGROUND

The mammalian innate immune system uses pattern recognition receptors (PRRs) to sense extracellular or intracellular pathogens by recognizing pathogen-associated molecular patterns to trigger the proper immune response. Nucleic acid sensors are one important class of PRRs that recognize foreign DNA or RNA upon microbial and other pathological conditions.

The cyclic GMP-AMP synthase/stimulator of interferon gene pathway (cGAS-STING pathway) is a component of the innate immune system that was recently discovered to be an important cytosolic immune surveillance pathway. cGAS is a universal DNA sensor that is activated upon binding to cytosolic DNA to produce the signaling molecule (2'-5',3'-5') cyclic guanosine monophosphate (GMP)-AMP. Acting as a second messenger during microbial infection, 2',3'-cGAMP binds and activates STING, leading to production of type I interferon (IFN) and other co-stimulatory molecules that trigger the immune response. STING has been shown to recognize bacterial-derived cyclic dinucleotides and elicit the type I IFN response.

Besides its role in infection, the cGAS/STING pathway has emerged as a promising new target for cancer immunotherapy and autoimmune diseases. Studies have shown that STING-dependent cytosolic DNA sensing can mediate innate immune recognition of immunogenic tumors and promote type I IFN dependent antitumor immunity. Unfortunately, natural cyclic dinucleotides (CDNs) that activate STING, such as cGAMP, are highly susceptible to phosphodiesterases. Synthetic CDN derivatives are more stable than natural CDNs but have higher toxicity and are less potent in humans.

New strategies to protect and deliver CDNs are needed.

4. SUMMARY

This disclosure provides lipid binding protein—(e.g., apolipoprotein-) based complexes for carrying one or more (e.g., one, two, three, four, or more than four) CDNs as cargo moieties. Without being bound by theory, it is believed that by incorporating the CDN into the complexes of the disclosure as cargo moieties, the complexes can be used to protect CDNs from degradation and deliver CDNs to target cells following administration to a subject. It is believed that CDNs bound to a complex of the disclosure will be released from the complex once the complex reaches a target cell because it is expected that the affinity of the CDN for its natural target is higher than the affinity of the CDN for the complex. Again without being bound by theory, it is believed CDNs delivered to a subject using complexes of the disclosure can modulate (e.g., induce) an immune response in the subject via STING activation. Thus, the complexes of the disclosure are useful, for example, for treating a subject having or being predisposed to a disease or disorder associated with or modulated by STING. For example, the complexes of the disclosure can be used to modulate an immune response in a subject having a cancer or an infectious disease.

In one aspect, the disclosure provides complexes comprising one or more lipid binding protein molecules (e.g., one or more Apolipoprotein A-I molecules) and one or more CDN binding moieties that bind one or more CDNs and indirectly couple the one or more CDNs to the lipid binding protein molecules.

In one aspect, complexes of the disclosure can be "Cargomer" based. Generally, Cargomers have a relatively low ratio of amphipathic molecules to apolipoprotein molecules. Typically, Cargomers comprise 1 to 8 apolipoprotein molecules (e.g., 1, 2, 4, or 8 apolipoprotein molecules) complexed with a sufficient number of amphipathic molecules (e.g., phospholipid molecules) to solubilize the apolipoprotein molecules. Cargomers also include cargo moieties, which can be, but are not necessarily, amphipathic molecules. Cargomers of the disclosure contain one or more cargo moieties which are CDN binding moieties. In addition to CDN binding moieties, a Cargomer of the disclosure can include one or more additional cargo moieties which are not CDN binding moieties. Such additional cargo moieties can be biologically active and/or diagnostically useful following administration to a subject. For example, an additional cargo moiety can be a biologically active molecule such as a drug, biologic, or immunogen. Cargomer-based complexes are further described in Section 6.1.1.

In another aspect, complexes of the disclosure can be non-Cargomer based, for example HDL-based or HDL mimetic-based. HDL-based and HDL mimetic-based complexes contain a relatively high number of amphipathic molecules (e.g., phospholipid molecules) compared to Cargomer-based complexes and are generally larger in size than Cargomer-based complexes. An HDL-based or HDL mimetic-based complex of the disclosure can comprise one or more CDN binding moieties which have been integrated into a reconstituted HDL or HDL mimetic such as CER-001, CSL-111, CSL-112, or ETC-216. A CDN binding moiety integrated into an HDL or an HDL mimetic complex can be considered a "cargo moiety" of the HDL-based or HDL mimetic complexes. HDL-based and HDL mimetic-based complexes are further described in Section 6.1.2. Such complexes can also include one or more cargo moieties in addition to the CDN binding moieties.

Lipid binding protein molecules and amphipathic molecules that can be included in Cargomer and non-Cargomer based complexes of the disclosure are described in Sections 6.1.3 and 6.1.4, respectively.

In some embodiments, the complexes of the disclosure include CDN binding moieties that comprise cationic peptides capable of binding a CDN. Such cationic peptides can be integrated into a lipid binding protein complex (e.g., an HDL mimetic or a Cargomer as described herein, where the cationic peptide is a "cargo moiety").

In some embodiments, the complexes of the disclosure include CDN binding moieties that comprise loop forming oligonucleotides (LFOs) such as riboswitch loops. LFOs can be attached, for example, to lipids embedded in a lipid binding protein complex (e.g., an HDL mimetic or a Cargomer as described herein, where the LFO is a "cargo moiety").

Further features of exemplary CDN binding moieties are described in detail in Section 6.1.5.

Optionally, a complex of the disclosure can comprise one or more anchor moieties directly or indirectly coupling the CDN binding moieties to amphipathic molecule(s) and/or to lipid binding protein molecule(s) present in the complex. An "anchor" as used herein refers to an amphipathic or apolar moiety that is covalently bound to a cargo moiety (which may be a CDN binding moiety) and which is non-covalently coupled to a lipid binding protein in the complex, either directly or, where the complex includes an amphipathic molecule other than the anchor moiety, via another amphipathic molecule in the complex. The use of an amphipathic anchor moiety can, in certain embodiments, contribute to the lipid binding protein: amphipathic molecule molar ratio in the complex. In other embodiments, the amphipathic anchor molecule does not contribute the lipid binding protein: amphipathic molecule molar ratio in the complex.

Amphipathic molecules useful as anchor moieties can have a positive net charge, a negative net charge, or a net charge of zero. The use of a charged amphipathic anchor moiety may circumvent or reduce the need for additional amphipathic molecules to solubilize the lipid binding protein molecule(s). Thus, in certain embodiments, anchor moieties and amphipathic molecules in a complex are the same. Features of exemplary anchors are described in Section 6.1.6.

Complexes of the disclosure optionally can also comprise, in addition to or in lieu of anchor moieties, one or more linker moieties. A "linker" as used herein refers to a moiety that covalently links one moiety (such as a CDN binding moiety or other cargo moiety) to an apolipoprotein molecule, an amphipathic molecule, or an anchor. Features of exemplary linker moieties are described in Section 6.1.7.

CDNs that can be incorporated into the complexes of the disclosure can be naturally occurring or synthetic. In the context of this disclosure, a "synthetic" CDN refers to a non-naturally occurring CDN. Naturally occurring CDNs that can be incorporated into the complexes of the disclosure can be isolated from a natural source or can be made by chemical synthesis. Exemplary CDNs are described in Section 6.1.8.

The disclosure further provides compositions comprising a complex of the disclosure. Compositions of the disclosure include compositions comprising complexes having bound CDNs and compositions comprising "empty" complexes that do not have bound CDNs. Compositions of the disclosure include pharmaceutical compositions. Exemplary compositions are described in Section 6.2.

The disclosure further provides processes for making complexes of the disclosure. Exemplary processes are described in Section 6.3.

The disclosure further provides methods of treating a subject that comprise administering a therapeutically effective amount of a complex or pharmaceutical composition of the disclosure to the subject.

The disclosure further provides methods of inducing an immune response in a subject that comprise administering a therapeutically effective amount of a complex or pharmaceutical composition of the disclosure to the subject.

The disclosure further provides methods of treating a subject afflicted with a cancer that comprise administering a therapeutically effective amount of a complex or pharmaceutical composition of the disclosure to the subject.

The disclosure further provides methods of treating an infection or infectious disease in a subject that comprise administering a therapeutically effective amount of a complex or pharmaceutical composition of the disclosure to the subject.

Exemplary methods of treating a subject are described in Section 6.4.

5. BRIEF DESCRIPTION OF THE FIGURES

Figure 1A:
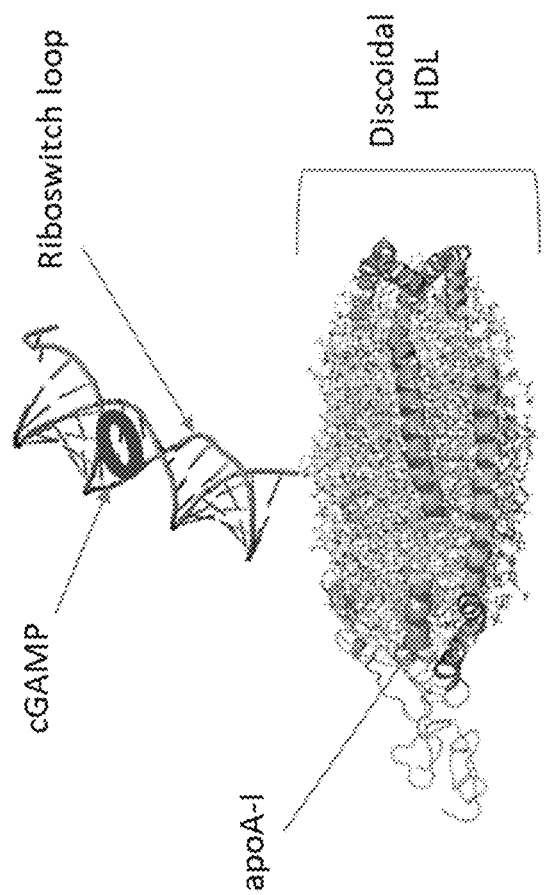

FIGS. 1A-1B: schematic representations of exemplary HDL-based (FIG. 1A) and exemplary Cargomer-based (FIG. 1B) complexes of the disclosure. In both FIG. 1A and FIG. 1B, the complex is shown carrying a CDN bound to a riboswitch loop.

6. DETAILED DESCRIPTION 6.1. CDN Carrying Complexes

This disclosure provides lipid binding protein-based complexes for delivering CDNs.

In one aspect, a complex of the disclosure comprises:
one or more lipid binding protein molecules;
one or more CDNs;
one or more CDN binding moieties that (i) non-covalently bind the one or more CDNs and (ii) indirectly couple the one or more CDNs to the one or more lipid binding protein molecules;
optionally, an amount of amphipathic molecules sufficient to solubilize the lipid binding protein molecules;
optionally, one or more anchors non-covalently coupling one or more CDN binding moieties to the lipid binding protein molecules; and
optionally, one or more linkers covalently coupling one or more CDN binding moieties to one or more lipid binding protein molecules, one or more amphipathic molecules or one or more anchors.

In some embodiments, the complex does not include amphipathic molecules. Without being bound by theory, it is believed that a charged CDN binding moiety can solubilize a lipid binding protein (e.g., ApoA-I or other lipid binding protein described in Section 6.1.3) without any amphipathic molecules such as a phospholipid.

Complexes of the disclosure can be Cargomer based, for example as described in Section 6.1.1. Complexes of the disclosure can also be non-Cargomer based, for example as described in Section 6.1.2.

6.1.1. Cargomer Based Complexes

In one aspect, complexes of the disclosure comprise Cargomers. Features of Cargomers that can be included in Cargomer based complexes of the disclosure are described in U.S. application Ser. No. 16/100,628, the contents of which are incorporated herein by reference in their entireties.

Cargomers of the disclosure generally comprise an apolipoprotein in monomeric or multimeric form (e.g., 2, 4, or 8 apolipoprotein molecules) and one or more CDN binding moieties as cargo moieties. One or more additional non-CDN binding moiety cargo moieties can also be included. Cargo moieties can be amphipathic or non-amphipathic. Amphipathic cargo moieties can solubilize the apolipoprotein and prevent it from aggregating. Where the cargo moieties are not amphipathic or insufficient to solubilize the apolipoprotein molecule(s), the Cargomers can also comprise one or more additional amphipathic molecules to solubilize the apolipoprotein. Thus, reference to amphipathic molecules in the context of the Cargomers of the disclosure encompasses amphipathic molecules that are cargo moieties, amphipathic molecules that are not cargo moieties, or some combination thereof. Preferably, Cargomers of the disclosure are not discoidal, for example as determined using NMR spectroscopy.

Both monomeric and multimeric apolipoproteins can be used to form Cargomers, thereby making it possible to make delivery vehicles with increasing cargo carrying capacity as the number of apolipoprotein molecules increases. Cargomers comprising multimeric apolipoproteins are believed to have a cargo carrying capacity that is higher than albumin, which has a limited apolar pocket to carry cargo molecules. Cargomers also contain a relatively low number of amphipathic molecules compared to discoidal or spherical HDL, which can provide lower toxicity, lower costs of production and a simpler manufacturing process. It is also believed that, due to their reduced size as compared to HDL-based delivery vehicles, Cargomers can penetrate the blood brain barrier and be taken up into the lymph, providing yet another advantage over larger drug delivery vehicles.

Cargo moieties can include biologically active molecules (e.g., drugs, biologics, and/or immunogens) or other agents, for example agents used in diagnostics. As used herein, the terms "molecule" and "agent" also include complexes and conjugates (for example, antibody-drug conjugates). The terms "biologically active," "diagnostically useful" and the like are not limited to substances with direct pharmacological or biological activity, and may include substances that become active following administration, for example due to metabolism of a prodrug or cleavage of a linker. According, the terms "biologically active" and "diagnostically useful" also includes substances that become biologically active or diagnostically useful after administration, through creation or metabolites or other cleavage products that exert a pharmacological or a biological effect and/or are detectable in a diagnostic test. In some embodiments, a Cargomer of the disclosure comprises one or more cargo moieties that are CDN binding moieties and one or more cargo moieties that are not CDN binding moieties. In some embodiments, a Cargomer of the disclosure comprises one or more cargo moieties that are CDN binding moieties and no other cargo moieties.

Cargomers are believed to provide several advantages over other delivery vehicles based on liposomes, discoidal or spherical HDL particles, and albumin. Once the CDN(s) is delivered in vivo, the remaining apolipoprotein can be integrated into the natural lipoprotein metabolism pathways, thereby avoiding accumulation of an empty carrier. Because the Cargomers of the disclosure contain a relatively small amount of amphipathic molecules relative to apolipoprotein, it is believed that the Cargomers of the disclosure can avoid toxicity problems, such as, but not limited to liver toxicity and C activation-related pseudoallergy (CARPA), than can potentially result from lipid based carriers. Without being bound by theory, it is believed that another advantage over other carriers is the flexibility of apolipoproteins to adapt to different complex sizes. Unlike the cavity of albumin, which due to its small size restrains the cargo to only few molecules, Cargomers offers a wide range of cargo carrying capacity.

Amphipathic molecules in a Cargomer can solubilize the apolipoprotein and/or reduce or minimize apolipoprotein aggregation, and can also have other functions in the Cargomer. For example, amphipathic molecules can have therapeutic utility, and thus may be cargo moieties intended for delivery by the Cargomer upon administration to a subject (e.g., such a Cargomer can comprise cargo moieties which are CDN binding moieties and additional cargo moieties which are amphipathic molecules having therapeutic utility). Additionally, as discussed in Section 6.1.6 below, amphipathic molecules can be used to anchor a non-amphipathic cargo moiety such as a non-amphipathic CDN binding moiety to the apolipoprotein in the Cargomer. Thus, in some embodiments, a cargo moiety and an amphipathic molecule in a Cargomer are the same. In other embodiments, an anchor moiety and an amphipathic molecule in a Cargomer are the same. In yet other embodiments, cargo moieties, anchor moieties and amphipathic molecules in a Cargomer are the same (for example, where an amphipathic molecule has therapeutic activity and also anchors another biologically active molecule or CDN binding moiety to the apolipoprotein molecule(s)).

Anchor and/or linker moieties are particularly useful for a Cargomer having a cargo moiety that is not an amphipathic molecule.

In some embodiments, at least one of the cargo moieties, a majority of the cargo moieties, or all of the cargo moieties in a Cargomer of the disclosure are coupled to the Cargomer via anchors. In some embodiments, at least one of the cargo moieties in a Cargomer is coupled to the Cargomer via an anchor. In some embodiments, a majority of the cargo moieties in a Cargomer are coupled to the Cargomer via anchors. In some embodiments, all of the cargo moieties in a Cargomer are coupled to the Cargomer via anchors. Each anchor in a Cargomer can be the same or, alternatively, different types of anchors can be included in a single Cargomer (e.g., one type of cargo moiety such as a CDN binding moiety can be coupled to the Cargomer via one type of anchor and a second type of cargo moiety can be coupled to the Cargomer via a second type of anchor).

In certain aspects, the amphipathic molecules, the CDN binding moieties, the CDNs and, if present, the anchors and/or linkers together contribute a net charge of at least +1 or −1 per apolipoprotein molecule in the Cargomer (e.g., +1, +2, +3, −1, −2, or −3). In some embodiments, the net charge is a negative charge. In other embodiments, the net charge is a positive charge. Unless required otherwise by context, charge is measured at physiological pH.

The molar ratio of apolipoprotein molecules to amphipathic molecules in a Cargomer of the disclosure can be but does not necessarily have to be in integers or reflect a one to one relationship between the apolipoprotein and amphipathic molecules. By way of example and not limitation, a Cargomer can have an apolipoprotein to amphipathic molecule molar ratio of 2:5, 8:7, 3:2, or 4:7.

In some embodiments, a complex of the disclosure comprises a Cargomer in which apolipoprotein molecules are complexed with amphipathic molecules in an apolipoprotein: amphipathic molecule molar ratio ranging from 8:1 to 1:15 (e.g., from 8:1 to 1:15, from 7:1 to 1:15, from 6:1 to 1:15, from 5:1 to 1:15, from 4:1 to 1:15, from 3:1 to 1:15, from 2:1 to 1:15, from 1:1 to 1:15, from 8:1 to 1:14, from 7:1 to 1:14, from 6:1 to 1:14, from 5:1 to 1:14, from 4:1 to 1:14, from 3:1 to 1:14, from 2:1 to 1:14, from 1:1 to 1:14, from 8:1 to 1:13, from 7:1 to 1:13, from 6:1 to 1:13, from 5:1 to 1:13, from 4:1 to 1:13, from 3:1 to 1:13, from 2:1 to 1:13, from 1:1 to 1:13, from 8:1 to 1:12, from 7:1 to 1:12, from 6:1 to 1:12, from 5:1 to 1:12, from 4:1 to 1:12, from 3:1 to 1:12, from 2:1 to 1:12, from 1:1 to 1:12, from 8:1 to 1:11, from 7:1 to 1:11, from 6:1 to 1:11, from 5:1 to 1:11, from 4:1 to 1:11, from 3:1 to 1:11, from 2:1 to 1:11, from 1:1 to 1:11, from 8:1 to 1:10, from 7:1 to 1:10, from 6:1 to 1:10, from 5:1 to 1:10, from 4:1 to 1:10, from 3:1 to 1:10, from 2:1 to 1:10, from 1:1 to 1:10, from 8:1 to 1:9, from 7:1 to 1:9, from 6:1 to 1:9, from 5:1 to 1:9, from 4:1 to 1:9, from 3:1 to 1:9, from 2:1 to 1:9, from 1:1 to 1:9, from 8:1 to 1:8, from 7:1 to 1:8, from 6:1 to 1:8, from 5:1 to 1:8, from 4:1 to 1:8, from 3:1 to 1:8, from 2:1 to 1:8, from 1:1 to 1:8, from 8:1 to 1:7, from 7:1 to 1:7, from 6:1 to 1:7, from 5:1 to 1:7, from 4:1 to 1:7, from 3:1 to 1:7, from 2:1 to 1:7, from 1:1 to 1:7, from 8:1 to 1:6, from 7:1 to 1:6, from 6:1 to 1:6, from 5:1 to 1:6, from 4:1 to 1:6, from 3:1 to 1:6, from 2:1 to 1:6, from 1:1 to 1:6, from 8:1 to 1:5, from 7:1 to 1:5, from 6:1 to 1:5, from 5:1 to 1:5, from 4:1 to 1:5, from 3:1 to 1:5, from 2:1 to 1:5, from 1:1 to 1:5, from 8:1 to 1:4, from 7:1 to 1:4, from 6:1 to 1:4, from 5:1 to 1:4, from 4:1 to 1:4, from 3:1 to 1:4, from 2:1 to 1:4, from 1:1 to 1:4, from 8:1 to 1:3, from 7:1 to 1:3, from 6:1 to 1:3, from 5:1 to 1:3, from 4:1 to 1:3, from 3:1 to 1:3, from 2:1 to 1:3, from 1:1 to 1:3, from 8:1 to 1:2, from 7:1 to 1:2, from 6:1 to 1:2, from 5:1 to 1:2, from 4:1 to 1:2, from 3:1 to 1:2, from 2:1 to 1:2, from 1:1 to 1:2, from 8:1 to 1:1, from 7:1 to 1:1, from 6:1 to 1:1, from 5:1 to 1:1, from 4:1 to 1:1, from 3:1 to 1:1, or from 2:1 to 1:1).

In some embodiments, the apolipoprotein to amphipathic molecule molar ratio in the Cargomer ranges from 6:1 to 1:6. In some embodiments, the apolipoprotein to amphipathic molecule molar ratio ranges from 5:1 to 1:6. In some embodiments, the apolipoprotein to amphipathic molecule molar ratio ranges from 4:1 to 1:6. In some embodiments, the apolipoprotein to amphipathic molecule molar ratio ranges from 3:1 to 1:6. In some embodiments, the apolipoprotein to amphipathic molecule molar ratio ranges from 2:1 to 1:6. In some embodiments, the apolipoprotein to amphipathic molecule molar ratio ranges from 5:1 to 1:5. In some embodiments, the apolipoprotein to amphipathic molecule molar ratio ranges from 4:1 to 1:5. In some embodiments, the apolipoprotein to amphipathic molecule molar ratio ranges from 3:1 to 1:5. In some embodiments, the apolipoprotein to amphipathic molecule molar ratio ranges from 2:1 to 1:5. In some embodiments, the apolipoprotein to amphipathic molecule molar ratio ranges from 5:1 to 1:4. In some embodiments, the apolipoprotein to amphipathic molecule molar ratio ranges from 4:1 to 1:4. In some embodiments, the apolipoprotein to amphipathic molecule molar ratio ranges from 3:1 to 1:4. In some embodiments, the apolipoprotein to amphipathic molecule molar ratio ranges from 2:1 to 1:4. In some embodiments, the apolipoprotein to amphipathic molecule molar ratio ranges from 5:1 to 1:3. In some embodiments, the apolipoprotein to amphipathic molecule molar ratio ranges from 4:1 to 1:3. In some embodiments, the apolipoprotein to amphipathic molecule molar ratio ranges from 3:1 to 1:3. In some embodiments, the apolipoprotein to amphipathic molecule molar ratio ranges from 2:1 to 1:3. In some embodiments, the apolipoprotein to amphipathic molecule molar ratio ranges from 5:1 to 1:2. In some embodiments, the apolipoprotein to amphipathic molecule molar ratio ranges from 4:1 to 1:2. In some embodiments, the apolipoprotein to amphipathic molecule molar ratio ranges from 3:1 to 1:2. In some embodiments, the apolipoprotein to amphipathic molecule molar ratio ranges from 2:1 to 1:2. In some embodiments, the apolipoprotein to amphipathic molecule molar ratio ranges from 5:1 to 1:1. In some embodiments, the apolipoprotein to amphipathic molecule molar ratio ranges from 4:1 to 1:1. In some embodiments, the apolipoprotein to amphipathic molecule molar ratio ranges from 3:1 to 1:1. In some embodiments, the apolipoprotein to amphipathic molecule molar ratio ranges from 2:1 to 1:1. In some embodiments, the apolipoprotein to amphipathic molecule molar ratio ranges from 1:1 to 1:6. In some embodiments, the apolipoprotein to amphipathic molecule molar ratio ranges from 1:1 to 1:5. In some embodiments, the apolipoprotein to amphipathic molecule molar ratio ranges from 1:1 to 1:4. In some embodiments, the apolipoprotein to amphipathic molecule molar ratio ranges from 1:1 to 1:3. In some embodiments, the apolipoprotein to amphipathic molecule molar ratio ranges from 1:1 to 1:2. In some embodiments, the apolipoprotein to amphipathic molecule molar ratio ranges from 1:2 to 1:6. In some embodiments, the apolipoprotein to amphipathic molecule molar ratio ranges from 1:2 to 1:5. In some embodiments, the apolipoprotein to amphipathic molecule molar ratio ranges from 1:2 to 1:4. In some embodiments, the apolipoprotein to amphipathic molecule molar ratio ranges from 1:2 to 1:3. In some embodiments, the apolipoprotein to amphipathic molecule molar ratio ranges from 1:3 to 1:6. In some embodiments, the apolipoprotein to amphipathic molecule molar ratio ranges from 1:3 to 1:5. In some embodiments, the apolipoprotein to amphipathic molecule molar ratio ranges from 1:3 to 1:4. In some embodiments, the apolipoprotein to amphipathic molecule molar ratio ranges from 1:4 to 1:6. In some embodiments, the apolipoprotein to amphipathic molecule molar ratio ranges from 1:4 to 1:5. In some embodiments, the apolipoprotein to amphipathic molecule molar ratio ranges from 1:5 to 1:6. In some embodiments, the apolipoprotein to amphipathic molecule molar ratio ranges from 1.5:1 to 1:2. In some embodiments, the apolipoprotein to amphipathic molecule molar ratio ranges from 5:4 to 4:5. In some embodiments, the apolipoprotein to amphipathic molecule molar ratio ranges from 5:3 to 3:5. In some embodiments, the apolipoprotein to amphipathic molecule molar ratio ranges from 5:2 to 2:5. In some embodiments, the apolipoprotein to amphipathic molecule molar ratio ranges from 3:2 to 2:3.

In some embodiments, the ratio of the apolipoprotein molecules to amphipathic molecules is about 1:1. In other embodiments, the ratio of the apolipoprotein molecules to amphipathic molecules is about 1:2. In yet other embodiments, the ratio of the apolipoprotein molecules to amphipathic molecules is about 1:3. In yet other embodiments, the ratio of the apolipoprotein molecules to amphipathic molecules is about 1:4. In yet other embodiments, the ratio of the apolipoprotein molecules to amphipathic molecules is about 1:5. In yet other embodiments, the ratio of the apolipoprotein molecules to amphipathic molecules is about 1:6.

In some embodiments, a Cargomer comprises 1 apolipoprotein molecule.

In other embodiments, a Cargomer comprises 2 apolipoprotein molecules. Cargomers comprising 2 apolipoprotein molecules preferably have a Stokes radius of 3 nm or less. In some embodiments, a Cargomer can comprise 2 apolipoprotein molecules and 1, 2, or 3 negatively charged amphipathic molecules (e.g., negatively charged phospholipid molecules) per apolipoprotein molecule.

In other embodiments, a Cargomer comprises 4 apolipoprotein molecules. Cargomers comprising 4 apolipoprotein molecules preferably have a Stokes radius of 4 nm or less. In some embodiments, a Cargomer can comprise 4 apolipoprotein molecules and 1, 2, or 3 negatively charged amphipathic molecules (e.g., negatively charged phospholipid molecules) per apolipoprotein molecule.

In other embodiments, a Cargomer comprises 8 apolipoprotein molecules. Cargomers comprising 8 apolipoprotein molecules preferably have a Stokes radius of 5 nm or less. In some embodiments, a Cargomer can comprise 8 apolipoprotein molecules and 1, 2, or 3 negatively charged amphipathic molecules (e.g., negatively charged phospholipid molecules) per apolipoprotein molecule. In certain embodiments, the Cargomers of the disclosure do not contain cholesterol and/or a cholesterol derivative (e.g., a cholesterol ester).

In some embodiments, a Cargomer of the disclosure comprises an apolipoprotein to phospholipid ratio in the range of about 1:2 to about 1:3 by weight.

In some embodiments, a Cargomer of the disclosure comprises an apolipoprotein to phospholipid ratio of 1:2.7 by weight.

The Cargomers of the disclosure are preferably soluble in a biological fluid, for example one or more of lymph, cerebrospinal fluid, vitreous humor, aqueous humor, and blood or a blood fraction (e.g., serum or plasma).

Cargomers may include a targeting functionality, for example to target the Cargomers to a particular cell or tissue type, or to an infectious agent. In some embodiments, the Cargomer includes a targeting moiety attached to an apolipoprotein molecule or an amphipathic molecule. In some embodiments, one or more cargo moieties that are incorporated into the Cargomer has a targeting capability.

6.1.2. HDL and HDL Mimetic-Based Complexes

In one aspect, the complexes of the disclosure comprise HDL or HDL mimetic-based complexes having one or more CDN binding moieties (as with Cargomer-based complexes, CDN binding moieties can be considered "cargo moieties" in HDL or HDL mimetic-based complexes). For example, complexes of the disclosure can comprise a lipoprotein complex as described in U.S. Pat. No. 8,206,750, PCT publication WO 2012/109162, PCT publication WO 2015/173633 A2 (e.g., CER-001) or US 2004/0229794 A1, the contents of each of which are incorporated herein by reference in their entireties, into which one or more CDN binding moieties have been incorporated (e.g., by being covalently attached to phospholipid molecules in the complex, either directly or via a linker and/or by being covalently attached to lipoprotein molecules in the complex, either directly or via a linker). Lipoprotein complexes of the disclosure can also include one or more additional cargo moieties in addition to the one or more CDN binding moieties. Lipoprotein complexes (e.g., as described in U.S. Pat. No. 8,206,750, WO 2012/109162, WO 2015/173633 A2 or US 2004/0229794 A1) can be adapted for carrying CDNs, for example, by combining a CDN binding moiety (e.g. anchored to a phospholipid) with one or more of the lipoprotein complex components prior to complex formation, or covalently attaching a CDN binding moiety to a component of the lipoprotein complex via a linker (e.g., to an apolipoprotein molecule). The terms "lipoproteins" and "apolipoproteins" are used interchangeably herein, and unless required otherwise by context, the term "lipoprotein" encompasses lipoprotein mimetics.

Lipoprotein complexes can comprise a protein fraction (e.g., an apolipoprotein fraction) and a lipid fraction (e.g., a phospholipid fraction). The protein fraction includes one or more lipid-binding protein molecules, such as apolipoproteins, peptides, or apolipoprotein peptide analogs or mimetics, for example one or more lipid binding protein molecules described in Section 6.1.3.

The lipid fraction typically includes one or more phospholipids which can be neutral, negatively charged, positively charged, or a combination thereof. Exemplary phospholipids and other amphipathic molecules which can be included in the lipid fraction are described in Section 6.1.4

In certain embodiments, the lipid fraction contains at least one neutral phospholipid (e.g., a sphingomyelin (SM)) and, optionally, one or more negatively charged phospholipids. In lipoprotein complexes that include both neutral and negatively charged phospholipids, the neutral and negatively charged phospholipids can have fatty acid chains with the same or different number of carbons and the same or different degree of saturation. In some instances, the neutral and negatively charged phospholipids will have the same acyl tail, for example a C16: 0, or palmitoyl, acyl chain. In specific embodiments, particularly those in which egg SM is used as the neutral lipid, the weight ratio of the apolipoprotein fraction: lipid fraction ranges from about 1:2.7 to about 1:3 (e.g., 1:2.7).

Any phospholipid that bears at least a partial negative charge at physiological pH can be used as the negatively charged phospholipid. Non-limiting examples include negatively charged forms, e.g., salts, of phosphatidylinositol, a phosphatidylserine, a phosphatidylglycerol and a phosphatidic acid. In a specific embodiment, the negatively charged phospholipid is 1,2-dipalmitoyl-sn-glycero-3-[phospho-rac-(1-glycerol)], or DPPG, a phosphatidylglycerol. Preferred salts include potassium and sodium salts.

In some embodiments, a lipoprotein complex which can be adapted to carry a CDN is a lipoprotein complex as described in U.S. Pat. No. 8,206,750 or WO 2012/109162 (and its U.S. counterpart, US 2012/0232005), the contents of each of which are incorporated herein in its entirety by reference. In particular embodiments, the protein component of the lipoprotein complex is as described in Section 6.1 and preferably in Section 6.1.1 of WO 2012/109162 (and US 2012/0232005), the lipid component is as described in Section 6.2 of WO 2012/109162 (and US 2012/0232005), which can optionally be complexed together in the amounts described in Section 6.3 of WO 2012/109162 (and US 2012/0232005). The contents of each of these sections are incorporated by reference herein. In certain aspects, a lipoprotein complex of the disclosure is in a population of complexes that is at least 85%, at least 90%, at least 95%, at least 97%, or at least 99% homogeneous, as described in Section 6.4 of WO 2012/109162 (and US 2012/0232005), the contents of which are incorporated by reference herein.

In a specific embodiment, the complex of the disclosure, in addition to any CDN binding moieties, anchors, linkers and additional cargo moieties, consists essentially of 2-4 ApoA-I equivalents, 2 molecules of charged phospholipid, 50-80 molecules of lecithin and 20-50 molecules of SM.

In another specific embodiment, the complex of the disclosure, in addition to any CDN binding moieties, anchors, linkers and additional cargo moieties, consists essentially of 2-4 ApoA-I equivalents, 2 molecules of charged phospholipid, 50 molecules of lecithin and 50 molecules of SM.

In yet another specific embodiment, the complex of the disclosure, in addition to any CDN binding moieties, anchors, linkers and additional cargo moieties, consists essentially of 2-4 ApoA-I equivalents, 2 molecules of charged phospholipid, 80 molecules of lecithin and 20 molecules of SM.

In yet another specific embodiment, the complex of the disclosure, in addition to any CDN binding moieties, anchors, linkers and additional cargo moieties, consists essentially of 2-4 ApoA-I equivalents, 2 molecules of charged phospholipid, 70 molecules of lecithin and 30 molecules of SM.

In yet another specific embodiment, the complex of the disclosure, in addition to any CDN binding moieties, anchors, linkers and additional cargo moieties, consists essentially of 2-4 ApoA-I equivalents, 2 molecules of charged phospholipid, 60 molecules of lecithin and 40 molecules of SM.

In a specific embodiment, the complex of the disclosure comprises a lipid component that consists essentially of about 90 to 99.8 wt % SM and about 0.2 to 10 wt % negatively charged phospholipid, for example, about 0.2-1 wt %, 0.2-2 wt %, 0.2-3 wt %, 0.2-4 wt %, 0.2-5 wt %, 0.2-6 wt %, 0.2-7 wt %, 0.2-8 wt %, 0.2-9 wt %, or 0.2-10 wt % total negatively charged phospholipid(s). In another specific embodiment, the complex of the disclosure comprises a lipid fraction that consists essentially of about 90 to 99.8 wt % lecithin and about 0.2 to 10 wt % negatively charged phospholipid, for example, about 0.2-1 wt %, 0.2-2 wt %, 0.2-3 wt %, 0.2-4 wt %, 0.2-5 wt %, 0.2-6 wt %, 0.2-7 wt %, 0.2-8 wt %, 0.2-9 wt % or 0.2-10 wt % total negatively charged phospholipid(s). In the embodiments described in this paragraph, one or more CDN binding moieties can, for example, be covalently bound to phospholipid molecules in the lipid component, either directly or via a linker.

In still another specific embodiment, the complex of the disclosure comprises a lipid fraction that consists essentially of about 9.8 to 90 wt % SM, about 9.8 to 90 wt % lecithin and about 0.2-10 wt % negatively charged phospholipid, for example, from about 0.2-1 wt %, 0.2-2 wt %, 0.2-3 wt %, 0.2-4 wt %, 0.2-5 wt %, 0.2-6 wt %, 0.2-7 wt %, 0.2-8 wt %, 0.2-9 wt %, to 0.2-10 wt % total negatively charged phospholipid(s). In the embodiments described in this paragraph, one or more CDN binding moieties can, for example, be covalently bound to phospholipid molecules in the lipid component, either directly or via a linker.

In another specific embodiment, a complex of the disclosure comprises an ApoA-I apolipoprotein and a lipid fraction, wherein the lipid fraction (in addition to any CDN binding moieties or additional cargo moieties) consists essentially of sphingomyelin and about 3 wt % of a negatively charged phospholipid, wherein the molar ratio of the lipid fraction to the ApoA-I apolipoprotein is about 2:1 to 200:1, and wherein said complex is a small or large discoidal particle containing 2-4 ApoA-I equivalents.

The HDL-based or HDL mimetic-based complexes of the disclosure can include a single type of lipid-binding protein, or mixtures of two or more different lipid-binding proteins, which may be derived from the same or different species. Although not required, the complexes will preferably comprise lipid-binding proteins that are derived from, or correspond in amino acid sequence to, the animal species being treated, in order to avoid inducing an immune response to the therapy. Thus, for treatment of human patients, lipid-binding proteins of human origin are preferably used. The use of peptide mimetic apolipoproteins may also reduce or avoid an immune response.

In some embodiments, the lipid component includes two types of phospholipids: a sphingomyelin (SM) and a negatively charged phospholipid. Exemplary SMs and negatively charged lipids are described in Section 6.1.4.1.

Lipid components including SM can optionally include small quantities of additional lipids. Virtually any type of lipids may be used, including, but not limited to, lysophospholipids, galactocerebroside, gangliosides, cerebrosides, glycerides, triglycerides, and cholesterol and its derivatives. When included, such optional lipids will typically comprise less than about 15 wt % of the lipid fraction, although in some instances more optional lipids could be included. In some embodiments, the optional lipids comprise less than about 10 wt %, less than about 5 wt %, or less than about 2 wt %. In some embodiments, the lipid fraction does not include optional lipids.

In a specific embodiment, the phospholipid fraction contains egg SM or palmitoyl SM or phytosphingomyelin and DPPG in a weight ratio (SM: negatively charged phospholipid) ranging from 90:10 to 99:1, more preferably ranging from 95:5 to 98:2. In one embodiment, the weight ratio is 97:3.

The molar ratio of the lipid component to the protein component of complexes of the disclosure can vary, and will depend upon, among other factors, the identity(ies) of the apolipoprotein comprising the protein component, the identities and quantities of the lipids comprising the lipid component, and the desired size of the complex. Because the biological activity of apolipoproteins such as ApoA-I are thought to be mediated by the amphipathic helices comprising the apolipoprotein, it is convenient to express the apolipoprotein fraction of the lipid: apolipoprotein molar ratio using ApoA-I protein equivalents. It is generally accepted that ApoA-I contains 6-10 amphipathic helices, depending upon the method used to calculate the helices. Other apolipoproteins can be expressed in terms of ApoA-I equivalents based upon the number of amphipathic helices they contain. For example, ApoA-IM, which typically exists as a disulfide-bridged dimer, can be expressed as 2 ApoA-I equivalents, because each molecule of ApoA-IM contains twice as many amphipathic helices as a molecule of ApoA-I. Conversely, a peptide apolipoprotein that contains a single amphipathic helix can be expressed as a 1/10-1/6 ApoA-I equivalent, because each molecule contains 1/10-1/6 as many amphipathic helices as a molecule of ApoA-I. In general, the lipid: ApoA-I equivalent molar ratio of the lipoprotein complexes (defined herein as "Ri") will range from about 105:1 to 110:1. In some embodiments, the Ri is about 108:1. Ratios in weight can be obtained using a MW of approximately 650-800 for phospholipids.

In some embodiments, the molar ratio of lipid: ApoA-I equivalents ("RSM") ranges from about 80:1 to about 110:1, e.g., about 80:1 to about 100:1. In a specific example, the RSM for complexes can be about 82:1.

In some embodiments, the complexes of the disclosure are negatively charged complexes which comprise a protein fraction which is preferably mature, full-length ApoA-I, and a lipid fraction comprising a neutral phospholipid, sphingomyelin (SM), and negatively charged phospholipid.

In a specific embodiment, the lipid component contains SM (e.g., egg SM, palmitoyl SM, phytoSM, or a combination thereof) and negatively charged phospholipid (e.g., DPPG) in a weight ratio (SM: negatively charged phospholipid) ranging from 90:10 to 99:1, more preferably ranging from 95:5 to 98:2, e.g., 97:3.

In specific embodiments, the ratio of the protein component to lipid component can range from about 1:2.7 to about 1:3, with 1:2.7 being preferred. This corresponds to molar ratios of ApoA-I protein to lipid ranging from approximately 1:90 to 1:140. In some embodiments, the molar ratio of protein to lipid in the complex is about 1:90 to about 1:120, about 1:100 to about 1:140, or about 1:95 to about 1:125.

In particular embodiments, the complex comprises CER-001, CSL-111, CSL-112, CER-522 or ETC-216 adapted to contain a CDN binding moiety. For example, CDN binding moieties can be attached to a protein or lipid component of one of these complexes by a linker or direct bond. In a preferred embodiment, the complex comprises CER-001 adapted to contain a CDN binding moiety.

CER-001 comprises ApoA-I, sphingomyelin (SM) and DPPG in a 1:2.7 ApoA-I wt: total phospholipid wt ratio with a SM: DPPG wt: wt ratio of 97:3. Preferably, the SM is egg SM, although synthetic SM or phyto SM can be substituted. In some embodiments, the complex is made according to the method described in Example 4 of WO 2012/109162.

CSL-111 is a reconstituted human ApoA-I purified from plasma complexed with soybean phosphatidylcholine (SBPC) (Tardif et al., 2007, JAMA 297:1675-1682).

CSL-112 is a formulation of ApoA-I purified from plasma and reconstituted to form HDL suitable for intravenous infusion (Diditchenko et al., 2013, DOI 10.1161/ATVBAHA. 113.301981).

ETC-216 (also known as MDCO-216) is a lipid-depleted form of HDL containing recombinant ApoA-I$_{Milano}$. See Nicholls et al., 2011, Expert Opin Biol Ther. 11 (3): 387-94. doi: 10.1517/14712598.2011.557061.

In another embodiment, a complex of the disclosure comprise CER-522 adapted to contain a CDN binding moiety. CER-522 is a lipoprotein complex comprising a combination of three phospholipids and a 22 amino acid peptide, CT80522:

line (Dipalmitoylphosphatidylcholine, DPPC) and 1,2-dipalmitoyl-sn-glycero-3-[phospho-rac-(1-glycerol)] (Dipalmitoylphosphatidyl-glycerol, DPPG) in a 48.5:48.5:3 weight ratio. The ratio of peptide to total phospholipids in the CER-522 complex is 1:2.5 (w/w).

In certain embodiments, a complex of the disclosure comprises a bioactive agent delivery particle as described in US 2004/0229794 adapted to carry a CDN binding moiety.

A bioactive agent delivery particle can comprise a lipid binding polypeptide (e.g., an apolipoprotein as described previously in this Section or in Section 6.1.3), a lipid bilayer (e.g., comprising one or more phospholipids as described previously in this Section or in Section 6.1.4.1), and a bioactive agent (e.g., an anti-cancer agent), wherein the interior of the lipid bilayer comprises a hydrophobic region, and wherein the bioactive agent is associated with the hydrophobic region of the lipid bilayer. Such bioactive agent delivery particles can be adapted to carry a CDN binding moiety, for example, by attaching a CDN binding moiety to a lipid binding polypeptide or phospholipid (directly or via a linker), and then incorporating the lipid binding polypeptide or phospholipid into a bioactive agent delivery particle.

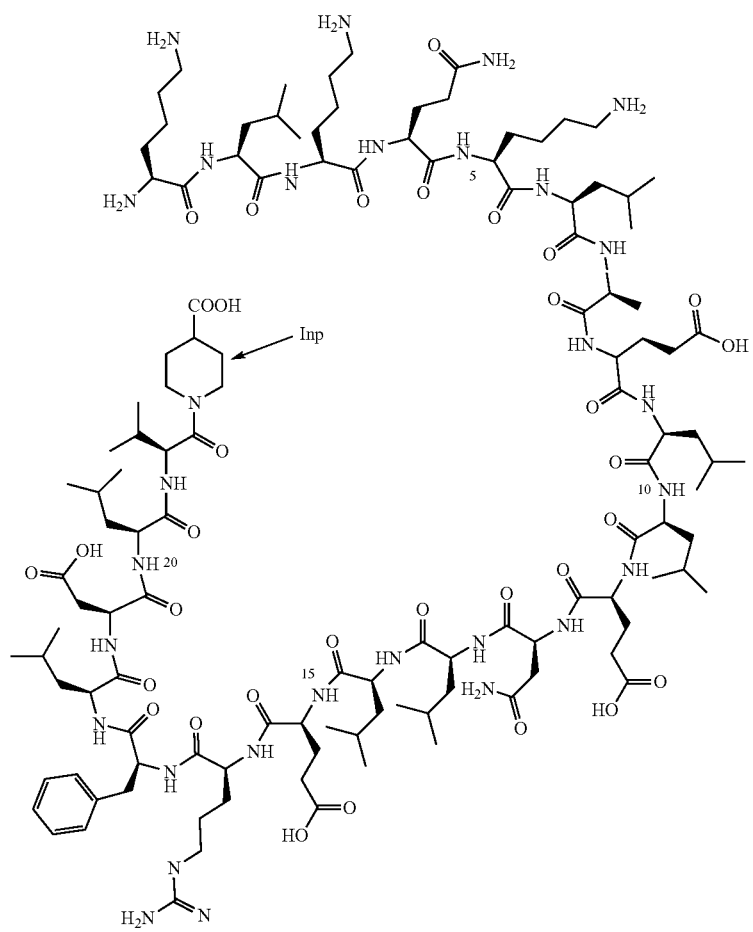

CT80522

Molecular weight: 2637.20
Exact Mass: 2634
$C_{123}H_{210}N_{30}O_{33}$

The phospholipid component of CER-522 consists of egg sphingomyelin, 1,2-dipalmitoyl-sn-glycero-3-phosphocho- In some embodiments, a bioactive agent delivery particle as described in US 2004/0229794 can be adapted to carry a CDN binding moiety by substituting a CDN binding moiety in place of one of the bioactive agents described in US 2004/0229794 or including a CDN binding moiety in addition to a bioactive agent described in US 2004/0229794.

In some embodiments, a bioactive agent delivery particle does not comprise a hydrophilic core.

In some embodiments, a bioactive agent delivery particle is disc shaped (e.g., having a diameter from about 7 to about 29 nm).

Bioactive agent delivery particles include bilayer-forming lipids, for example phospholipids (e.g., as described previously in this Section or in Section 6.1.4.1). In some embodiments, a bioactive agent delivery particle includes both bilayer-forming and non-bilayer-forming lipids. In some embodiments, the lipid bilayer of a bioactive agent delivery particle includes phospholipids. In one embodiment, the phospholipids incorporated into a delivery particle include dimyristoylphosphatidylcholine (DMPC) and dimyristoylphosphatidylglycerol (DMPG). In one embodiment, the lipid bilayer includes DMPC and DMPG in a 7:3 molar ratio.

In some embodiments, the lipid binding polypeptide is an apolipoprotein (e.g., as described previously in this Section or in Section 6.1.3). The predominant interaction between lipid binding polypeptides. e.g., apolipoprotein molecules, and the lipid bilayer is generally a hydrophobic interaction between residues on a hydrophobic face of an amphipathic structure, e.g., an α-helix of the lipid binding polypeptide and fatty acyl chains of lipids on an exterior surface at the perimeter of the particle. Bioactive agent delivery particles may include exchangeable and/or non-exchangeable apolipoproteins. In one embodiment, the lipid binding polypeptide is ApoA-I.

In some embodiments, bioactive agent delivery particles include lipid binding polypeptide molecules, e.g., apolipoprotein molecules, that have been modified to increase stability of the particle. In one embodiment, the modification includes introduction of cysteine residues to form intramolecular and/or intermolecular disulfide bonds.

In another embodiment, bioactive agent delivery particles include a chimeric lipid binding polypeptide molecule, e.g., a chimeric apolipoprotein molecule, with one or more bound functional moieties, for example one or more targeting moieties and/or one or more moieties having a desired biological activity, e.g., antimicrobial activity, which may augment or work in synergy with the activity of a bioactive agent incorporated into the delivery particle.

6.1.3. Lipid Binding Protein Molecules

Lipid binding protein molecules that can be used in the complexes of the disclosure include apolipoproteins such as those described in Section 6.1.3.1 and apolipoprotein mimetic peptides such as those described in Section 6.1.3.2. In some embodiments, the complex comprises a mixture of lipid binding protein molecules. In some embodiments, the complex comprises a mixture of one or more lipid binding protein molecules and one or more apolipoprotein mimetic peptides.

In some embodiments, the complex comprises 1 to 8 ApoA-I equivalents (e.g., 1, 2, 3, 4, 5, 6, 7, 8, 1 to 7, 1 to 6, 1 to 5, 1 to 4, 1 to 3, 1 to 2, 2 to 8, 2 to 6, 2 to 4, 4 to 6, or 4 to 8 ApoA-I equivalents). Lipid binding proteins can be expressed in terms of ApoA-I equivalents based upon the number of amphipathic helices they contain. For example, ApoA-IM, which typically exists as a disulfide-bridged dimer, can be expressed as 2 ApoA-I equivalents, because each molecule of ApoA-IM contains twice as many amphipathic helices as a molecule of ApoA-I. Conversely, a peptide mimetic that contains a single amphipathic helix can be expressed as a 1/10-1/6 ApoA-I equivalent, because each molecule contains 1/10-1/6 as many amphipathic helices as a molecule of ApoA-I.

6.1.3.1. Apolipoproteins

Suitable apolipoproteins that can be included in the complexes of the disclosure include apolipoproteins ApoA-I, ApoA-II, ApoA-IV, ApoA-V, ApoB, ApoC-I, ApoC-II, ApoC-III, ApoD, ApoE, ApoJ, ApoH, and any combination of two or more of the foregoing. Polymorphic forms, isoforms, variants and mutants as well as truncated forms of the foregoing apolipoproteins, the most common of which are Apolipoprotein A-$I_{Milano}$ (ApoA-$I_M$), Apolipoprotein A-$I_{Paris}$ (ApoA-$I_p$), and Apolipoprotein A-$I_{Zaragoza}$ (ApoA-$I_Z$), can also be used. Apolipoproteins mutants containing cysteine residues are also known, and can also be used (see, e.g., U.S. Publication No. 2003/0181372). The apolipoproteins may be in the form of monomers or dimers, which may be homodimers or heterodimers. For example, homo- and heterodimers (where feasible) of ApoA-I (Duverger et al., 1996, Arterioscler. Thromb. Vasc. Biol. 16 (12): 1424-29), ApoA-$I_M$ (Franceschini et al., 1985, J. Biol. Chem. 260: 1632-35), ApoA-$I_p$ (Daum et al., 1999, J. Mol. Med. 77:614-22), ApoA-II (Shelness et al., 1985, J. Biol. Chem. 260 (14): 8637-46; Shelness et al., 1984, J. Biol. Chem. 259 (15): 9929-35), ApoA-IV (Duverger et al., 1991, Euro. J. Biochem. 201 (2): 373-83), ApoE (McLean et al., 1983, J. Biol. Chem. 258 (14): 8993-9000), ApoJ and ApoH may be used.

The apolipoproteins can be modified in their primary sequence to render them less susceptible to oxidations, for example, as described in U.S. Publication Nos. 2008/0234192 and 2013/0137628, and U.S. Pat. Nos. 8,143,224 and 8,541,236. The apolipoproteins can include residues corresponding to elements that facilitate their isolation, such as His tags, or other elements designed for other purposes. Preferably, the apolipoprotein in the complex is soluble in a biological fluid (e.g., lymph, cerebrospinal fluid, vitreous humor, aqueous humor, blood, or a blood fraction (e.g., serum or plasma).

In some embodiments, the complex comprises covalently bound lipid-binding protein monomers, e.g., dimeric apolipoprotein A-$I_{Milano}$, which is a mutated form of ApoA-I containing a cysteine. The cysteine allows the formation of a disulfide bridge which can lead to the formation of homodimers or heterodimers (e.g., ApoA-I Milano-ApoA-II).

In some embodiments, the apolipoprotein molecules comprise ApoA-I, ApoA-II, ApoA-IV, ApoA-V, ApoB, ApoC-I, ApoC-II, ApoC-III, ApoD, ApoE, ApoJ, or ApoH molecules or a combination thereof.

In some embodiments, the apolipoprotein molecules comprise or consist of ApoA-I molecules. In some embodiments, said ApoA-I molecules are human ApoA-I molecules. In some embodiments, said ApoA-I molecules are recombinant.

In some embodiments, the ApoA-I molecules are Apolipoprotein A-$I_{Milano}$ (ApoA-$I_M$), Apolipoprotein A-$I_{Paris}$ (ApoA-IP), or Apolipoprotein A-$I_{Zaragoza}$ (ApoA-$I_Z$) molecules.

Apolipoproteins can be purified from animal sources (and in particular from human sources) or produced recombinantly as is well-known in the art, see, e.g., Chung et al., 1980, J. Lipid Res. 21 (3): 284-91; Cheung et al., 1987, J. Lipid Res. 28 (8): 913-29. See also U.S. Pat. Nos. 5,059,528, 5,128,318, 6,617,134; U.S. Publication Nos. 2002/0156007, 2004/0067873, 2004/0077541, and 2004/0266660; and PCT Publications Nos. WO 2008/104890 and WO 2007/023476. Other methods of purification are also possible, for example as described in PCT Publication No. WO 2012/109162, the disclosure of which is incorporated herein by reference in its entirety.

The apolipoprotein can be in prepro-form, pro-form, or mature form. For example, a complex can comprise ApoA-I (e.g., human ApoA-I) in which the ApoA-I is preproApoA-I, proApoA-I, or mature ApoA-I. In some embodiments, the complex comprises ApoA-I that has at least 90% sequence identity to SEQ ID NO: 1. In other embodiments, the complex comprises ApoA-I that has at least 95% sequence identity to SEQ ID NO:1. In other embodiments, the complex comprises ApoA-I that has at least 98% sequence identity to SEQ ID NO:1. In other embodiments, the complex comprises ApoA-I that has at least 99% sequence identity to SEQ ID NO:1. In other embodiments, the complex comprises ApoA-I that has 100% sequence identity to SEQ ID NO:1.

In some embodiments, the complex comprises 1 to 8 apolipoprotein molecules (e.g., 1 to 6, 1 to 4, 1 to 2, 2 to 8, 2 to 6, 2 to 4, 4 to 8, 4 to 6, or 6 to 8 apolipoprotein molecules). In some embodiments, the complex comprises 1 apolipoprotein molecule. In some embodiments, the complex comprises 2 apolipoprotein molecules. In some embodiments, the complex comprises 3 apolipoprotein molecules. In some embodiments, the complex comprises 4 apolipoprotein molecules. In some embodiments, the complex comprises 5 apolipoprotein molecules. In some embodiments, the complex comprises 6 apolipoprotein molecules. In some embodiments, the complex comprises 7 apolipoprotein molecules. In some embodiments, the complex comprises 8 apolipoprotein molecules.

The apolipoprotein molecule(s) can comprise a chimeric apolipoprotein comprising an apolipoprotein and one or more attached functional moieties, such as for example, one or more CDN binding moieties, one or more targeting moieties, a moiety having a desired biological activity, an affinity tag to assist with purification, and/or a reporter molecule for characterization or localization studies. An attached moiety with biological activity may have an activity that is capable of augmenting and/or synergizing with the biological activity of a compound or cargo moiety incorporated into a complex of the disclosure. For example, a moiety with biological activity may have antimicrobial (for example, antifungal, antibacterial, anti-protozoal, bacteriostatic, fungistatic, or antiviral) activity. In one embodiment, an attached functional moiety of a chimeric apolipoprotein is not in contact with hydrophobic surfaces of the complex. In another embodiment, an attached functional moiety is in contact with hydrophobic surfaces of the complex. In some embodiments, a functional moiety of a chimeric apolipoprotein may be intrinsic to a natural protein. In some embodiments, a chimeric apolipoprotein includes a ligand or sequence recognized by or capable of interaction with a cell surface receptor or other cell surface moiety.

In one embodiment, a chimeric apolipoprotein includes a targeting moiety that is not intrinsic to the native apolipoprotein, such as for example, S. cerevisiae α-mating factor peptide, folic acid, transferrin, or lactoferrin. In another embodiment, a chimeric apolipoprotein includes a moiety with a desired biological activity that augments and/or synergizes with the activity of a compound or cargo moiety incorporated into a complex of the disclosure. In one embodiment, a chimeric apolipoprotein may include a functional moiety intrinsic to an apolipoprotein. One example of an apolipoprotein intrinsic functional moiety is the intrinsic targeting moiety formed approximately by amino acids 130-150 of human ApoE, which comprises the receptor binding region recognized by members of the low density lipoprotein receptor family. Other examples of apolipoprotein intrinsic functional moieties include the region of ApoB-100 that interacts with the low density lipoprotein receptor and the region of ApoA-I that interacts with scavenger receptor type B 1. In other embodiments, a functional moiety may be added synthetically or recombinantly to produce a chimeric apolipoprotein. Another example is an apolipoprotein with the prepro or pro sequence from another preproapolipoprotein (e.g., prepro sequence from preproapoA-II substituted for the prepro sequence of preproapoA-I). Another example is an apolipoprotein for which some of the amphipathic sequence segments have been substituted by other amphipathic sequence segments from another apolipoprotein.

As used herein, "chimeric" refers to two or more molecules that are capable of existing separately and are joined together to form a single molecule having the desired functionality of all of its constituent molecules. The constituent molecules of a chimeric molecule may be joined synthetically by chemical conjugation or, where the constituent molecules are all polypeptides or analogs thereof, polynucleotides encoding the polypeptides may be fused together recombinantly such that a single continuous polypeptide is expressed. Such a chimeric molecule is termed a fusion protein. A "fusion protein" is a chimeric molecule in which the constituent molecules are all polypeptides and are attached (fused) to each other such that the chimeric molecule forms a continuous single chain. The various constituents can be directly attached to each other or can be coupled through one or more linkers. One or more segments of various constituents can be, for example, inserted in the sequence of an apolipoprotein, or, as another example, can be added N-terminal or C-terminal to the sequence of an apolipoprotein. For example, a fusion protein can comprise an antibody light chain, an antibody fragment, a heavy-chain antibody, or a single-domain antibody.

In some embodiments, a chimeric apolipoprotein is prepared by chemically conjugating the apolipoprotein and the functional moiety to be attached (e.g., a CDN binding moiety). Means of chemically conjugating molecules are well known to those of skill in the art. Such means will vary according to the structure of the moiety to be attached, but will be readily ascertainable to those of skill in the art. Polypeptides typically contain a variety of functional groups, e.g., carboxylic acid (—COOH), free amino (—NH2), or sulfhydryl (—SH) groups, that are available for reaction with a suitable functional group on the functional moiety or on a linker to bind the moiety thereto. A functional moiety may be attached at the N-terminus, the C-terminus, or to a functional group on an interior residue (i.e., a residue at a position intermediate between the N- and C-termini) of an apolipoprotein molecule. Alternatively, the apolipoprotein and/or the moiety to be tagged can be derivatized to expose or attach additional reactive functional groups.

In some embodiments, fusion proteins that include a polypeptide functional moiety are synthesized using recombinant expression systems. Typically, this involves creating a nucleic acid (e.g., DNA) sequence that encodes the apolipoprotein and the functional moiety such that the two polypeptides will be in frame when expressed, placing the DNA under the control of a promoter, expressing the protein in a host cell, and isolating the expressed protein.

A nucleic acid encoding a chimeric apolipoprotein can be incorporated into a recombinant expression vector in a form suitable for expression in a host cell. As used herein, an "expression vector" is a nucleic acid which, when introduced into an appropriate host cell, can be transcribed and translated into a polypeptide. The vector may also include regulatory sequences such as promoters, enhancers, or other expression control elements (e.g., polyadenylation signals). Such regulatory sequences are known to those skilled in the art (see, e.g., Goeddel, 1990, Gene Expression Technology: Meth. Enzymol. 185, Academic Press, San Diego, Calif.; Berger and Kimmel, Guide to Molecular Cloning Techniques, Methods in Enzymology 152 Academic Press, Inc., San Diego, Calif.; Sambrook et al., 1989, Molecular Cloning—A Laboratory Manual (2nd ed.) Vol. 1-3, Cold Spring Harbor Laboratory, Cold Spring Harbor Press, NY, etc.).

In some embodiments, an apolipoprotein has been modified such that when the apolipoprotein is incorporated into a complex of the disclosure, the modification will increase stability of the complex, confer targeting ability or increase capacity. In one embodiment, the modification includes introduction of cysteine residues into apolipoprotein molecules to permit formation of intramolecular or intermolecular disulfide bonds, e.g., by site-directed mutagenesis. In another embodiment, a chemical crosslinking agent is used to form intermolecular links between apolipoprotein molecules to enhance stability of the complex. Intermolecular crosslinking prevents or reduces dissociation of apolipoprotein molecules from the complex and/or prevents displacement by endogenous apolipoprotein molecules within an individual to whom the complexes are administered. In other embodiments, an apolipoprotein is modified either by chemical derivatization of one or more amino acid residues or by site directed mutagenesis, to confer targeting ability to or recognition by a cell surface receptor.

Complexes of the disclosure can be targeted to a specific cell surface receptor by engineering receptor recognition properties into an apolipoprotein. For example, complexes may be targeted to a particular cell type known to harbor a particular type of infectious agent, for example by modifying the apolipoprotein to render it capable of interacting with a receptor on the surface of the cell type being targeted. For example, complexes may be targeted to macrophages by altering the apolipoprotein to confer recognition by the macrophage endocytic class A scavenger receptor (SR-A). SR-A binding ability can be conferred to a complex by modifying the apolipoprotein by site directed mutagenesis to replace one or more positively charged amino acids with a neutral or negatively charged amino acid. SR-A recognition can also be conferred by preparing a chimeric apolipoprotein that includes an N- or C-terminal extension having a ligand recognized by SR-A or an amino acid sequence with a high concentration of negatively charged residues. Complexes comprising apolipoproteins can also interact with apolipoprotein receptors such as, but not limited to, ABCA1 receptors, ABCG1 receptors, Megalin, Cubulin and HDL receptors such as SR-B1.

The SR-B1 and other HDL receptors (e.g., ABCA1) are scavenger receptors essential to cell homeostasis, proliferation, and growth that can be up-regulated in cancer cells. Therefore, complexes of the disclosure can be used to target delivery of CDNs (e.g., as described in Section 6.1.8) and other therapeutic agents to cancer cells and tumors via the expression of SR-B1 and other HDL receptors on the surface of cancer cells.

A complex of the disclosure can comprise a lipid binding protein (e.g., an apolipoprotein molecule) which anchors a CDN binding moiety or an additional cargo moiety which is not a CDN binding moiety to the complex. In some embodiments, the apolipoprotein molecule is coupled to a CDN binding moiety or additional cargo moiety by a direct bond. In other embodiments, the apolipoprotein molecule is coupled to the CDN binding moiety or additional cargo moiety by a linker, e.g., as described in Section 6.1.7.

6.1.3.2. Apolipoprotein Mimetics

Peptides, peptide analogs, and agonists that mimic the activity of an apolipoprotein (collectively referred to herein as "apolipoprotein peptide mimetics") can also be used in the complexes of the disclosure, either alone, in combination with one or more other lipid binding proteins. Non-limiting examples of peptides and peptide analogs that correspond to apolipoproteins, as well as agonists that mimic the activity of ApoA-I, ApoA-I$_M$, ApoA-II, ApoA-IV, and ApoE, that are suitable for inclusion in the complexes and compositions described herein are disclosed in U.S. Pat. Nos. 6,004,925, 6,037,323 and 6,046,166 (issued to Dasseux et al.), U.S. Pat. No. 5,840,688 (issued to Tso), U.S. Pat. No. 6,743,778 (issued to Kohno), U.S. Publication Nos. 2004/0266671, 2004/0254120, 2003/0171277 and 2003/0045460 (to Fogelman), U.S. Publication No. 2006/0069030 (to Bachovchin), U.S. Publication No. 2003/0087819 (to Bielicki), U.S. Publication No. 2009/0081293 (to Murase et al.), and PCT Publication No. WO/2010/093918 (to Dasseux et al.), the disclosures of which are incorporated herein by reference in their entireties. These peptides and peptide analogues can be composed of L-amino acid or D-amino acids or mixture of L- and D-amino acids. They may also include one or more non-peptide or amide linkages, such as one or more well-known peptide/amide isosteres. Such apolipoprotein peptide mimetic can be synthesized or manufactured using any technique for peptide synthesis known in the art, including, e.g., the techniques described in U.S. Pat. Nos. 6,004,925, 6,037,323 and 6,046,166.

In some embodiments, the lipid binding protein molecules comprise apolipoprotein peptide mimetic molecules and optionally one or more apolipoprotein molecules such as those described above.

In some embodiments, the apolipoprotein peptide mimetic molecules comprise an ApoA-I peptide mimetic, ApoA-II peptide mimetic, ApoA-IV peptide mimetic, or ApoE peptide mimetic or a combination thereof.

A complex of the disclosure can comprise an apolipoprotein peptide mimetic molecule which anchors a CDN binding moiety or an additional cargo moiety which is not a CDN binding moiety to the complex. In some embodiments, the apolipoprotein peptide mimetic molecule is coupled to the CDN binding moiety or additional cargo moiety by a direct bond. In other embodiments, the apolipoprotein peptide mimetic molecule is coupled to the CDN binding moiety by a linker, e.g., as described in Section 6.1.7.

6.1.4. Amphipathic Molecules

An amphipathic molecule is a molecule that possesses both hydrophobic (apolar) and hydrophilic (polar) elements. Amphipathic molecules that can be used in the complexes of the disclosure include lipids (e.g., as described in Section 6.1.4.1), detergents (e.g., as described in Section 6.1.4.2), fatty acids (e.g., as described in Section 6.1.4.3), and apolar molecules and sterols covalently attached to polar molecules such as, but not limited to, sugars or nucleic acids (e.g., as described in Section 6.1.4.4). The complexes of the disclosure can include a single class of amphipathic molecule (e.g., a single species of phospholipids or a mixture of phospholipids), or can contain a combination of classes of amphipathic molecules (e.g., phospholipids and detergents). The complex can contain one species of amphipathic molecules or a combination of amphipathic molecules configured to facilitate solubilization of the lipid binding protein molecule(s).

In some embodiments, Cargomer-based complexes comprise only an amount of amphipathic molecules sufficient to solubilize the lipid binding protein molecules. In other words, a Cargomer-based complex can comprise the minimum amount of one or more amphipathic molecules necessary to solubilize the lipid binding protein molecules.

In some embodiments, the amphipathic molecules included in complexes of the disclosure comprise a phospholipid, a detergent, a fatty acid, an apolar moiety or sterol covalently attached to a sugar, or a combination thereof (e.g., selected from the types of amphipathic molecules discussed above).

In some embodiments, the amphipathic molecules comprise or consist of phospholipid molecules. In some embodiments, the phospholipid molecules comprise negatively charged phospholipids, neutral phospholipids, positively charged phospholipids or a combination thereof. In some embodiments, the phospholipid molecules contribute a net charge of 1-3 per apolipoprotein molecule in the complex. In some embodiments, the net charge is a negative net charge. In some embodiments, the net charge is a positive net charge. In some embodiments, the phospholipid molecules consist of a combination of negatively charged and neutral phospholipids. In some embodiments, the molar ratio of negatively charge phospholipid to neutral phospholipid ranges from 1:1 to 1:3. In some embodiments, the molar ratio of negatively charged phospholipid to neutral phospholipid is about 1:1 or about 1:2.

In some embodiments, a complex of the disclosure comprises at least one amphipathic molecule which is an anchor. In some embodiments, the amphipathic molecule which is an anchor is coupled to one of the CDN binding moieties by a direct bond. In some embodiments, the amphipathic molecule which is an anchor is coupled to one of the CDN binding moieties by a linker.

In some embodiments, the amphipathic molecules comprise neutral phospholipids and negatively charged phospholipids in a weight ratio of 95:5 to 99:1.

6.1.4.1. Lipids

Complexes of the disclosure can include one or more lipids. In various embodiments, one or more lipids can be saturated and/or unsaturated, natural and/or synthetic, charged or not charged, zwitterionic or not. In some embodiments, the lipid molecules (e.g., phospholipid molecules) can together contribute a net charge of 1-3 (e.g., 1-3, 1-2, 2-3, 1, 2, or 3) per lipid binding protein molecule in the complex. In some embodiments, the net charge is negative. In other embodiments, the net charge is positive.

In some embodiments, the lipid comprises a phospholipid. Phospholipids can have two acyl chains that are the same or different (for example, chains having a different number of carbon atoms, a different degree of saturation between the acyl chains, different branching of the acyl chains, or a combination thereof). The lipid can also be modified to contain a fluorescent probe (e.g., as described at avantilipids.com/product-category/products/fluorescent-lipids/). Preferably, the lipid comprises at least one phospholipid.

Phospholipids can have unsaturated or saturated acyl chains ranging from about 6 to about 24 carbon atoms (e.g., 6-20, 6-16, 6-12, 12-24, 12-20, 12-16, 16-24, 16-20, or 20-24). In some embodiments, a phospholipid used in a complex of the disclosure has one or two acyl chains of 12, 14, 16, 18, 20, 22, or 24 carbons (e.g., two acyl chains of the same length or two acyl chains of different length).

Non-limiting examples of acyl chains present in commonly occurring fatty acids that can be included in phospholipids are provided in Table 1, below:

TABLE 1

| Length: Number of Unsaturations | Common Name |
| --- | --- |
| 14:0 | myristic acid |
| 16:0 | palmitic acid |
| 18:0 | stearic acid |
| 18:1 cis$\Delta^9$ | oleic acid |
| 18:2 cis$\Delta^{9, 12}$ | linoleic acid |
| 18:3 cis$\Delta^{9, 12, 15}$ | linonenic acid |
| 20:4 cis$\Delta^{5, 8, 11, 14}$ | arachidonic acid |
| 20:5 cis$\Delta^{5, 8, 11, 14, 17}$ | eicosapentaenoic acid (an omega-3 fatty acid) |

Lipids that can be present in the complexes of the disclosure include, but are not limited to, small alkyl chain phospholipids, egg phosphatidylcholine, soybean phosphatidylcholine, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, phosphatidylglycerols, diphosphatidylglycerols such as dimyristoylphosphatidylglycerol, dipalmitoylphosphatidylglycerol, distearoylphosphatidylglycerol, dioleoylphosphatidylglycerol, dimyristoylphosphatidic acid, dipalmitoylphosphatidic acid, dimyristoylphosphatidylethanolamine, dipalmitoylphosphatidylethanolamine, dimyristoylphosphatidylserine, dipalmitoylphosphatidylserine, brain phosphatidylserine, brain sphingomyelin, palmitoylsphingomyelin, dipalmitoylsphingomyelin, egg sphingomyelin, milk sphingomyelin, phytosphingomyelin, distearoylsphingomyelin, dipalmitoylphosphatidylglycerol salt, phosphatidic acid, galactocerebroside, gangliosides, cerebrosides, dilaurylphosphatidylcholine, (1,3)-D-mannosyl-(1,3) diglyceride, aminophenylglycoside, 3-cholesteryl-6'-(glycosylthio) hexyl ether glycolipids, and cholesterol and its derivatives. Synthetic lipids, such as synthetic palmitoylsphingomyelin or N-palmitoyl-4-hydroxysphinganine-1-phosphocholine (a form of phytosphingomyelin) can be used to minimize lipid oxidation.

In some embodiments, the complexes of the disclosure includes two types of phospholipids: a neutral lipid, e.g., lecithin and/or sphingomyelin (abbreviated SM), and a charged phospholipid (e.g., a negatively charged phospholipid). A "neutral" phospholipid has a net charge of about zero at physiological pH. In many embodiments, neutral phospholipids are zwitterions, although other types of net neutral phospholipids are known and can be used. In some embodiments, the molar ratio of the charged phospholipid (e.g., negatively charged phospholipid) to neutral phospholipid ranges from 1:1 to 1:3, for example, about 1:1, about 1:2, or about 1:3.

The neutral phospholipid can comprise, for example, one or both of the lecithin and/or SM, and can optionally include other neutral phospholipids. In some embodiments, the neutral phospholipid comprises lecithin, but not SM. In other embodiments, the neutral phospholipid comprises SM, but not lecithin. In still other embodiments, the neutral phospholipid comprises both lecithin and SM. All of these specific exemplary embodiments can include neutral phospholipids in addition to the lecithin and/or SM, but in many embodiments do not include such additional neutral phospholipids.

As used herein, the expression "SM" includes sphingomyelins derived or obtained from natural sources, as well as analogs and derivatives of naturally occurring SMs that are impervious to hydrolysis by LCAT, as is naturally occurring SM. SM is a phospholipid very similar in structure to lecithin, but, unlike lecithin, it does not have a glycerol backbone, and hence does not have ester linkages attaching the acyl chains. Rather, SM has a ceramide backbone, with amide linkages connecting the acyl chains. SM can be obtained, for example, from milk, egg or brain. SM analogues or derivatives can also be used. Non-limiting examples of useful SM analogues and derivatives include, but are not limited to, palmitoylsphingomyelin, N-palmitoyl-4-hydroxysphinganine-1-phosphocholine (a form of phytosphingomyelin), palmitoylsphingomyelin, stearoylsphingomyelin, D-erythro-N-16:0-sphingomyelin and its dihydro isomer, D-erythro-N-16:0-dihydro-sphingomyelin. Synthetic SM such as synthetic palmitoylsphingomyelin or N-palmitoyl-4-hydroxysphinganine-1-phosphocholine (phytosphingomyelin) can be used in order to produce more homogeneous complexes and with fewer contaminants and/or oxidation products than sphingolipids of animal origin. Methods for synthesizing SM are described in U.S. Publication No. 2016/0075634.

Sphingomyelins isolated from natural sources can be artificially enriched in one particular saturated or unsaturated acyl chain. For example, milk sphingomyelin (Avanti Phospholipid, Alabaster, Ala.) is characterized by long saturated acyl chains (i.e., acyl chains having 20 or more carbon atoms). In contrast, egg sphingomyelin is characterized by short saturated acyl chains (i.e., acyl chains having fewer than 20 carbon atoms). For example, whereas only about 20% of milk sphingomyelin comprises C16: 0 (16 carbon, saturated) acyl chains, about 80% of egg sphingomyelin comprises C16: 0 acyl chains. Using solvent extraction, the composition of milk sphingomyelin can be enriched to have an acyl chain composition comparable to that of egg sphingomyelin, or vice versa.

The SM can be semi-synthetic such that it has particular acyl chains. For example, milk sphingomyelin can be first purified from milk, then one particular acyl chain, e.g., the C16: 0 acyl chain, can be cleaved and replaced by another acyl chain. The SM can also be entirely synthesized, by e.g., large-scale synthesis. See, e.g., Dong et al., U.S. Pat. No. 5,220,043, entitled Synthesis of D-erythro-sphingomyelins, issued Jun. 15, 1993; Weis, 1999, Chem. Phys. Lipids 102 (1-2): 3-12. SM can be fully synthetic, e.g., as described in U.S. Publication No. 2014/0275590.

The lengths and saturation levels of the acyl chains comprising a semi-synthetic or a synthetic SM can be selectively varied. The acyl chains can be saturated or unsaturated, and can contain from about 6 to about 24 carbon atoms. Each chain can contain the same number of carbon atoms or, alternatively each chain can contain different numbers of carbon atoms. In some embodiments, the semi-synthetic or synthetic SM comprises mixed acyl chains such that one chain is saturated and one chain is unsaturated. In such mixed acyl chain SMs, the chain lengths can be the same or different. In other embodiments, the acyl chains of the semi-synthetic or synthetic SM are either both saturated or both unsaturated. Again, the chains can contain the same or different numbers of carbon atoms. In some embodiments, both acyl chains comprising the semi-synthetic or synthetic SM are identical. In a specific embodiment, the chains correspond to the acyl chains of a naturally-occurring fatty acid, such as for example oleic, palmitic or stearic acid. In another embodiment, SM with saturated or unsaturated functionalized chains is used. In another specific embodiment, both acyl chains are saturated and contain from 6 to 24 carbon atoms. Non-limiting examples of acyl chains present in commonly occurring fatty acids that can be included in semi-synthetic and synthetic SMs are provided in Table 1, above.

In some embodiments, the SM is palmitoyl SM, such as synthetic palmitoyl SM, which has C16: 0 acyl chains, or is egg SM, which includes as a principal component palmitoyl SM.

In a specific embodiment, functionalized SM, such as phytosphingomyelin, is used.

Lecithin can be derived or isolated from natural sources, or it can be obtained synthetically. Examples of suitable lecithins isolated from natural sources include, but are not limited to, egg phosphatidylcholine and soybean phosphatidylcholine. Additional non-limiting examples of suitable lecithins include, dipalmitoylphosphatidylcholine, dimyristoylphosphatidylcholine, distearoylphosphatidylcholine 1-myristoyl-2-palmitoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, 1-palmitoy 1-2-oleoylphosphatidylcholine, 1-oleoyl-2-palmitylphosphatidylcholine, dioleoylphosphatidylcholine and the ether derivatives or analogs thereof.

Lecithins derived or isolated from natural sources can be enriched to include specified acyl chains. In embodiments employing semi-synthetic or synthetic lecithins, the identity(ies) of the acyl chains can be selectively varied, as discussed above in connection with SM. In some embodiments of the complexes described herein, both acyl chains on the lecithin are identical. In some embodiments of complexes that include both SM and lecithin, the acyl chains of the SM and lecithin are all identical. In a specific embodiment, the acyl chains correspond to the acyl chains of myristitic, palmitic, oleic or stearic acid.

The complexes of the disclosure can include one or more negatively charged phospholipids (e.g., alone or in combination with one or more neutral phospholipids). As used herein, "negatively charged phospholipids" are phospholipids that have a net negative charge at physiological pH. The negatively charged phospholipid can comprise a single type of negatively charged phospholipid, or a mixture of two or more different, negatively charged, phospholipids. In some embodiments, the charged phospholipids are negatively charged glycerophospholipids. Specific examples of suitable negatively charged phospholipids include, but are not limited to, a 1,2-dipalmitoyl-sn-glycero-3-[phospho-rac-(1-glycerol)], a phosphatidylglycerol, a phospatidylinositol, a phosphatidylserine, a phosphatidic acid, and salts thereof (e.g., sodium salts or potassium salts). In some embodiments, the negatively charged phospholipid comprises one or more of phosphatidylinositol, phosphatidylserine, phosphatidylglycerol and/or phosphatidic acid. In a specific embodiment, the negatively charged phospholipid comprises or consists of a salt of a phosphatidylglycerol or a salt of a phosphatidylinositol. In another specific embodiment, the negatively charged phospholipid comprises or consists of 1,2-dipalmitoyl-sn-glycero-3-[phospho-rac-(1-glycerol)], or DPPG, or a salt thereof.

The negatively charged phospholipids can be obtained from natural sources or prepared by chemical synthesis. In embodiments employing synthetic negatively charged phospholipids, the identities of the acyl chains can be selectively varied, as discussed above in connection with SM. In some embodiments of the complexes of the disclosure, both acyl chains on the negatively charged phospholipids are identical. In some embodiments, the acyl chains all types of phospholipids included in a complex of the disclosure are all identical. In a specific embodiment, the complex comprises negatively charged phospholipid(s), and/or SM all having C16: 0 or C16: 1 acyl chains. In a specific embodiment the fatty acid moiety of the SM is predominantly C16: 1 palmitoyl. In one specific embodiment, the acyl chains of the charged phospholipid(s), lecithin and/or SM correspond to the acyl chain of palmitic acid. In yet another specific embodiment, the acyl chains of the charged phospholipid(s), lecithin and/or SM correspond to the acyl chain of oleic acid.

Examples of positively charged phospholipids that can be included in the complexes of the disclosure include N1-[2-((1S)-1-[(3-aminopropyl) amino]-4-[di (3-amino-propyl) amino]butylcarboxamido) ethyl]-3,4-di [oleyloxy]-benzamide, 1,2-di-O-octadecenyl-3-trimethylammonium propane, 1,2-dimyristoleoyl-sn-glycero-3-ethylphosphocholine, 1-palmitoyl-2-oleoyl-sn-glycero-3-ethylphosphocholine, 1,2-dioleoyl-sn-glycero-3-ethylphosphocholine, 1,2-distearoyl-sn-glycero-3-ethylphosphocholine, 1,2-dipalmitoyl-sn-glycero-3-ethylphosphocholine, 1,2-dimyristoyl-sn-glycero-3-ethylphosphocholine, 1,2-dilauroyl-sn-glycero-3-ethylphosphocholine, 1,2-dilauroyl-sn-glycero-3-ethylphosphocholine, 1,2-dioleoyl-3-dimethylammonium-propane1,2-dimyristoyl-3-dimethylammonium-propane, 1,2-dipalmitoyl-3-dimethylammonium-propane, N-(4-carboxybenzyl)-N, N-dimethyl-2,3-bis (oleoyloxy) propan-1-aminium, 1,2-dioleoyl-3-trimethylammonium-propane, 1,2-dioleoyl-3-trimethylammonium-propane, 1,2-stearoyl-3-trimethylammonium-propane, 1,2-dipalmitoyl-3-trimethylammonium-propane, 1,2-dimyristoyl-3-trimethylammonium-propane, N-[1-(2,3-dimyristyloxy)propyl]-N, N-dimethyl-N-(2-hydroxyethyl) ammonium bromide, N, N, N-trimethyl-2-bis [(1-oxo-9-octadecenyl) oxy]-(Z,Z)-1propanaminium methyl sulfate, and salts thereof (e.g., chloride or bromide salts).

The lipids used are preferably at least 95% pure, and/or have reduced levels of oxidative agents (such as but not limited to peroxides). Lipids obtained from natural sources preferably have fewer polyunsaturated fatty acid moieties and/or fatty acid moieties that are not susceptible to oxidation. The level of oxidation in a sample can be determined using an iodometric method, which provides a peroxide value, expressed in milli-equivalent number of isolated iodines per kg of sample, abbreviated meq O/kg. See, e.g., Gray, 1978, Measurement of Lipid Oxidation: A Review, Journal of the American Oil Chemists Society 55:539-545; Heaton, F. W. and Ur, Improved Iodometric Methods for the Determination of Lipid Peroxides, 1958, Journal of the Science of Food and Agriculture 9:781-786. Preferably, the level of oxidation, or peroxide level, is low, e.g., less than 5 meq O/kg, less than 4 meq O/kg, less than 3 meq O/kg, or less than 2 meq O/kg.

Complexes of the disclosure can in some embodiments include small quantities of additional lipids. Virtually any type of lipids can be used, including, but not limited to, lysophospholipids, galactocerebroside, gangliosides, cerebrosides, glycerides, triglycerides, and sterols and sterol derivatives (e.g., a plant sterol, an animal sterol, such as cholesterol, or a sterol derivative, such as a cholesterol derivative). For example, a complex of the disclosure can contain cholesterol or a cholesterol derivative, e.g., a cholesterol ester. The cholesterol derivative can also be a substituted cholesterol or a substituted cholesterol ester. The complexes of the disclosure can also contain an oxidized sterol such as, but not limited to, oxidized cholesterol or an oxidized sterol derivative (such as, but not limited to, an oxidized cholesterol ester). In some embodiments, the complexes do not include cholesterol and/or its derivatives (such as a cholesterol ester or an oxidized cholesterol ester).

6.1.4.2. Detergents

The complexes of the disclosure can contain one or more detergents. The detergent can be zwitterionic, nonionic, cationic, anionic, or a combination thereof. Exemplary zwitterionic detergents include 3-[(3-Cholamidopropyl) dimethylammonio]-1-propanesulfonate (CHAPS), 3-[(3-Cholamidopropyl) dimethylammonio]-2-hydroxy-1-propanesulfonate (CHAPSO), and N,N-dimethyldodecylamine N-oxide (LDAO). Exemplary nonionic detergents include D-(+)-trehalose 6-monooleate, N-octanoyl-N-methylglucamine, N-nonanoyl-N-methylglucamine, N-decanoyl-N-methylglucamine, 1-(7Z-hexadecenoyl)-rac-glycerol, 1-(8Z-hexadecenoyl)-rac-glycerol, 1-(8Z-heptadecenoyl)-rac-glycerol, 1-(9Z-hexadecenoyl)-rac-glycerol, 1-decanoyl-rac-glycerol. Exemplary cationic detergents include (S)—O-methyl-serine dodecylamide hydrochloride, dodecylammonium chloride, decyltrimethylammonium bromide, and cetyltrimethylammonium sulfate. Exemplary anionic detergents include cholesteryl hemisuccinate, cholate, alkyl sulfates, and alkyl sulfonates.

6.1.4.3. Fatty Acids

The complexes of the disclosure can contain one or more fatty acids. The one or more fatty acids can include short-chain fatty acids having aliphatic tails of five or fewer carbons (e.g. butyric acid, isobutyric acid, valeric acid, or isovaleric acid), medium-chain fatty acids having aliphatic tails of 6 to 12 carbons (e.g., caproic acid, caprylic acid, capric acid, or lauric acid), long-chain fatty acids having aliphatic tails of 13 to 21 carbons (e.g., myristic acid, palmitic acid, stearic acid, or arachidic acid), very long chain fatty acids having aliphatic tails of 22 or more carbons (e.g., behenic acid, lignoceric acid, or cerotic acid), or a combination thereof. The one or more fatty acids can be saturated (e.g., caprylic acid, capric acid, lauric acid, myristic acid, palmitic acid, stearic acid, arachidic acid, behenic acid, lignoceric acid, or cerotic acid), unsaturated (e.g., myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, or docosahexaenoic acid) or a combination thereof. Unsaturated fatty acids can be cis or trans fatty acids. In some embodiments, unsaturated fatty acids used in the complexes of the disclosure are cis fatty acids.

6.1.4.4. Apolar Molecules and Sterols Attached to a Sugar

The complexes can contain one or more amphipathic molecules that comprise an apolar molecule or moiety (e.g., a hydrocarbon chain, an acyl or diacyl chain) or a sterol (e.g., cholesterol) attached to a sugar (e.g., a monosaccharide such as glucose or galactose, or a disaccharide such as maltose or trehalose). The sugar can be a modified sugar or a substituted sugar. Exemplary amphipathic molecules comprising an apolar molecule attached to a sugar include dodecan-2-yloxy-β-D-maltoside, tridecan-3-yloxy-β-D-maltoside, tridecan-2-yloxy-β-D-maltoside, n-dodecyl-β-D-maltoside (DDM), n-octyl-β-D-glucoside, n-nonyl-β-D-glucoside, n-decyl-β-D-maltoside, n-dodecyl-β-D- maltopyranoside, 4-n-Dodecyl-α, α-trehalose, 6-n-dodecyl-α,α-trehalose, and 3-n-dodecyl-α,α-trehalose.

In some embodiments, the apolar moiety is an acyl or a diacyl chain.

In some embodiments, the sugar is a modified sugar or a substituted sugar.

6.1.5. CDN Binding Moieties

The complexes of the disclosure comprise one or more CDN binding moieties (e.g., one, two, or three CDN binding moieties per complex). In some embodiments, a complex (e.g., a Cargomer of the disclosure) has 1 to 25 CDN binding moieties (e.g., 1 to 5, 1 to 10, 1 to 15, 1 to 20, 5 to 10, 5 to 15, 5 to 20, 10 to 25, 10 to 20, 10 to 15, 15 to 25, 15 to 20, or 20 to 25 CDN binding moieties). A complex can have, for example, 1, 2, 3, 4, 5, 6, 7, 8, 9, 10, 11, 12, 13, 14, 15, 16, 17, 18, 19, 20, 21, 22, 23, 24, or 25 CDN binding moieties.

CDN binding moieties can be charged to partially or fully neutralize charges that can be present in CDNs, e.g., charged phosphate groups of a CDN. In some embodiments, the CDN binding moiety is positively charged at physiological pH. In some embodiments, the CDN binding moiety has a positive charge of +2 to +8 at physiological pH. For example, a CDN binding moiety can have a charge of +2 to +6, +2 to +4, +4 to +8, +4 to +6, or +6 to +8 at physiological pH. In specific embodiments, a CDN binding moiety has a charge of +1, +2, +3, +4, +5, +6, +7, or +8 at physiological pH.

In some embodiments, the net charge of a CDN and its CDN binding moiety taken together is 0, 1, or 2. Thus, for example, the net charge of CDN binding moiety and a bound CDN can range from −2 to +2, −2 to +1, −2 to 0, −2 to −1, −1 to +2, −1 to +1, −1 to 0, 0 to +2, 0 to +1, or +1 to +2 at physiological pH. In some embodiments, the net charge of a CDN and its CDN binding moiety is 0 at physiological pH. In other embodiments, the net charge of a CDN and its CDN binding moiety is +1 at physiological pH. In other embodiments, the net charge of a CDN and its CDN binding moiety is −1 at physiological pH. In other embodiments, the net charge of a CDN and its CDN binding moiety is +2 at physiological pH. In other embodiments, the net charge of a CDN and its CDN binding moiety is −2 at physiological pH.

CDN binding moieties can be coupled to other components of the complexes of the disclosure, for example a lipid binding protein molecule or an amphipathic molecule such as a lipid. CDN binding moieties can be coupled to other components directly or by a linker, for example a linker described in Section 6.1.7.

In some embodiments, at least one CDN binding moiety is coupled to one of the one or more lipid binding protein molecules in the complex. In some embodiments, the CDN binding moiety is coupled to the lipid binding protein molecule by a direct bond. In other embodiments, the CDN binding moiety is coupled to the lipid binding protein molecule by a linker, for example, a bifunctional linker, cleavable linker, dipeptide linker, or a non-cleavable linker.

6.1.5.1. Positively Charged Peptides

CDN binding moieties can comprise positively charged peptides. Positively charged peptides can contain one or more positively charged amino acid residues that give the CDN binding moiety a net positive charge at physiological pH. CDN binding moieties can contain a single type of positively charged amino acid or can contain more than one type of positively charged amino acid (e.g., 2, 3, or 4 types of positively charged amino acids). CDN binding moieties comprising a positively charged peptide preferably have a positive charge of +2 to +8 at physiological pH (e.g., +2 to +6, +2 to +4, +4 to +8, +4 to +6, or +6 to +8, +2, +3, +4, +5, +6, +7, or +8 at physiological pH).

In some embodiments, the positively charged peptide comprises lysine residues, arginine residues, ornithine residues, histidine residues, or a combination thereof. In some embodiments, the positively charged peptide comprises or consists of lysine residues. In some embodiments, the positively charged peptide comprises or consists of arginine residues. In some embodiments, the positively charged peptide comprises or consists of ornithine residues. In some embodiments, the positively charged peptide comprises or consists of histidine residues.

A CDN binding moiety comprising a charged peptide can comprise a peptide that is made up entirely of positively charged amino acids, or can comprise a combination of positively charged amino acids and amino acids that are not positively charged. Preferably, the amino acids that are not positively charged are uncharged at physiological pH (e.g., glycine).

In some embodiments, the positively charged peptide comprises positively charged amino acids and further comprises one or more uncharged amino acids, such as glycine. In some embodiments, the positively charged peptide can comprise an uncharged amino acid between charged amino acids (e.g., the peptide can comprise alternating charged and uncharged residues).

In some embodiments, the positively charged peptide comprises 2 to 8 lysine residues (e.g., 2 to 6, 2 to 4, 4 to 8, 4 to 6, or 6 to 8 lysine residues). In some embodiments, the positively charged peptide comprises 2 to 8 arginine residues (e.g., 2 to 6, 2 to 4, 4 to 8, 4 to 6, or 6 to 8 arginine residues). In some embodiments, the positively charged peptide comprises 2 to 8 ornithine residues (e.g., 2 to 6, 2 to 4, 4 to 8, 4 to 6, or 6 to 8 ornithine residues). In some embodiments, the positively charged peptide comprises 2 to 8 histidine residues (e.g., 2 to 6, 2 to 4, 4 to 8, 4 to 6, or 6 to 8 histidine residues). The 2 to 8 lysine residues, 2 to 8 arginine residues, 2 to 8 ornithine residues, or 2 to 8 histidine residues can be consecutive or can be separated by one or more other amino acid residues (e.g., glycine residues). In some embodiments, the 2 to 8 lysine residues, 2 to 8 arginine residues, 2 to 8 ornithine residues, or 2 to 8 histidine residues are consecutive.

6.1.5.2. Loop-forming Oligonucleotides

CDN binding moieties can comprise a loop-forming oligonucleotide (LFO). LFOs suitable for use as CDN binding moieties are oligonucleotides that form loops capable of binding a CDN. LFOs that can be used as CDN binding moieties include natural and engineered riboswitches and loop forming portions thereof. A riboswitch is a regulatory segment of a mRNA molecule capable of binding a small molecule, such as a CDN, and which modifies expression of the protein encoded by the mRNA. Complexes of the disclosure comprising a CDN binding moiety which is a riboswitch or a loop forming portion thereof take advantage of the natural ability of the riboswitch to bind CDNs, thereby enabling complexes of the disclosure to carry CDNs.

Riboswitches that can be adapted for use in the complexes of the disclosure are described in the art, for example, by Nelson et al., 2015, PNAS, 112 (17): 5389-5394, Ren et al., 2015, Cell Reports, 11:1-12, and Bose et al., 2016, Cell Chemical Biology, 23:11539-1549, the contents of each of which are incorporated herein by reference in their entireties. LFOs can also be identified using computational methods, for example as described in Chang et al., 2009, RNA, 15 (7): 1426-1430, Mukherjee and Sengupta, 2016, Bioinformatics, 32 (5): 776-8, and Singh et al., 2009, BMC Bioinformatics. 10:325, the contents of each of which are incorporated herein in their entireties. LFOs (e.g., a riboswitch as described in the publications identified in this paragraph or identified using a computational method) can be adapted for use in the complexes of the disclosure by coupling the LFO to an anchor such as a phospholipid or to a lipid binding protein. A CDN binding moiety can comprise a full length riboswitch sequence or can comprise the CDN binding portion of a riboswitch but less than the full riboswitch sequence.

A LFO used as a CDN binding moiety can comprise, for example, RNA, DNA, or peptide nucleic acids (PNAs). PNAs that can be incorporated in the CDN binding moieties of the disclosure are described in the art, for example, Nielsen et al., 1991, Science, 254 (5037): 1497-1500, and Pansuwan et al., 2017, Bioconjug Chem. 28 (9): 2284-2292, the contents of which are incorporated herein by reference in their entireties. In some embodiments, a LFO comprises RNA. In other embodiments, a LFO comprises DNA. In yet other embodiments, a LFO comprises PNAs. The RNA sequence of a riboswitch (e.g., as described in one of the publications described in the previous paragraph) can be converted to a DNA sequence for making a DNA-based LFO or converted to a PNA sequence for making a PNA-based LFO. DNA-based LFOs and PNA-based LFOs can have increased stability compared to RNA-based LFOs.

LFOs of the disclosure can include modifications that block or reduce the rate at which the LFO is degraded by nucleases in vivo (see, e.g. www.ididna.com/pages/education/decoded/article/modification-highlight-modifications-that-block-nuclease-degradation for a description of exemplary modifications that can be incorporated into LFOs of the disclosure). For example, a LFO can include one or more phosphorothioate (PS) bonds which substitute sulfur atoms for non-bridging oxygen atoms in the LFO's phosphate backbone. As another example, a LFO can contain one or more 2'-O-methyl (2'OMe) modifications. As yet another example, a LFO can contain one or more 2' fluoro bases. As yet another example, a LFO can contain an inverted dT nucleotide at its 3' end and/or an inverted ddT at its 5' end. As yet another example, a LFO can be phosphorylated at its 3' end. Combinations of these modifications can also be used, for example, a combination of PS bonds and one or more 2' fluoro bases.

The length of a LFO can be varied, and can contain one or more loops capable of binding one or more CDNs. For example, a LFO can comprise the full sequence of a riboswitch or can comprise less than the full sequence of the riboswitch, for example, only the CDN binding loop or the CDN binding loop and one or more additional nucleotides.

In some embodiments, the LFO is 20 to 150 nucleotides in length. In some embodiments, the LFO is 20 to 140 nucleotides in length. In some embodiments, the LFO is 20 to 130 nucleotides in length. In some embodiments, the LFO is 20 to 120 nucleotides in length. In some embodiments, the LFO is 20 to 110 nucleotides in length. In some embodiments, the LFO is 20 to 100 nucleotides in length. In some embodiments, the LFO is 20 to 90 nucleotides in length. In some embodiments, the LFO is 20 to 80 nucleotides in length. In some embodiments, the LFO is 20 to 70 nucleotides in length. In some embodiments, the LFO is 20 to 60 nucleotides in length. In some embodiments, the LFO is 20 to 50 nucleotides in length. In some embodiments, the LFO is 20 to 40 nucleotides in length. In some embodiments, the LFO is 20 to 30 nucleotides in length. In some embodiments, the LFO is 30 to 150 nucleotides in length. In some embodiments, the LFO is 30 to 140 nucleotides in length. In some embodiments, the LFO is 30 to 130 nucleotides in length. In some embodiments, the LFO is 30 to 120 nucleotides in length. In some embodiments, the LFO is 30 to 110 nucleotides in length. In some embodiments, the LFO is 30 to 100 nucleotides in length. In some embodiments, the LFO is 30 to 90 nucleotides in length. In some embodiments, the LFO is 30 to 80 nucleotides in length. In some embodiments, the LFO is 30 to 70 nucleotides in length. In some embodiments, the LFO is 30 to 60 nucleotides in length. In some embodiments, the LFO is 30 to 50 nucleotides in length. In some embodiments, the LFO is 30 to 40 nucleotides in length. In some embodiments, the LFO is 40 to 150 nucleotides in length. In some embodiments, the LFO is 40 to 140 nucleotides in length. In some embodiments, the LFO is 40 to 130 nucleotides in length. In some embodiments, the LFO is 40 to 120 nucleotides in length. In some embodiments, the LFO is 40 to 110 nucleotides in length. In some embodiments, the LFO is 40 to 100 nucleotides in length. In some embodiments, the LFO is 40 to 90 nucleotides in length. In some embodiments, the LFO is 40 to 80 nucleotides in length. In some embodiments, the LFO is 40 to 70 nucleotides in length. In some embodiments, the LFO is 40 to 60 nucleotides in length. In some embodiments, rein the LFO is 40 to 50 nucleotides in length. In some embodiments, the LFO is 50 to 150 nucleotides in length. In some embodiments, the LFO is 50 to 140 nucleotides in length. In some embodiments, the LFO is 50 to 130 nucleotides in length. In some embodiments, the LFO is 50 to 120 nucleotides in length. In some embodiments, the LFO is 50 to 110 nucleotides in length. In some embodiments, the LFO is 50 to 100 nucleotides in length. In some embodiments, the LFO is 50 to 90 nucleotides in length. In some embodiments, the LFO is 50 to 80 nucleotides in length. In some embodiments, the LFO is 50 to 70 nucleotides in length. In some embodiments, the LFO is 50 to 60 nucleotides in length. In some embodiments, the LFO is 60 to 150 nucleotides in length. In some embodiments, the LFO is 60 to 140 nucleotides in length. In some embodiments, the LFO is 60 to 130 nucleotides in length. In some embodiments, the LFO is 60 to 120 nucleotides in length. In some embodiments, the LFO is 60 to 110 nucleotides in length. In some embodiments, the LFO is 60 to 100 nucleotides in length. In some embodiments, the LFO is 60 to 90 nucleotides in length. In some embodiments, the LFO is 60 to 80 nucleotides in length. In some embodiments, the LFO is 60 to 70 nucleotides in length. In some embodiments, the LFO is 70 to 150 nucleotides in length. In some embodiments, the LFO is 70 to 140 nucleotides in length. In some embodiments, the LFO is 70 to 130 nucleotides in length. In some embodiments, the LFO is 70 to 120 nucleotides in length. In some embodiments, the LFO is 70 to 110 nucleotides in length. In some embodiments, the LFO is 70 to 100 nucleotides in length. In some embodiments, the LFO is 70 to 90 nucleotides in length. In some embodiments, the LFO is 70 to 80 nucleotides in length. In some embodiments, the LFO is 80 to 150 nucleotides in length. In some embodiments, the LFO is 80 to 140 nucleotides in length. In some embodiments, the LFO is 80 to 130 nucleotides in length. In some embodiments, the LFO is 80 to 120 nucleotides in length. In some embodiments, the LFO is 80 to 110 nucleotides in length. In some embodiments, the LFO is 80 to 100 nucleotides in length. In some embodiments, the LFO is 80 to 90 nucleotides in length. In some embodiments, the LFO is 90 to 150 nucleotides in length. In some embodiments, the LFO is 90 to 140 nucleotides in length. In some embodiments, the LFO is 90 to 130 nucleotides in length. In some embodiments, the LFO is 90 to 120 nucleotides in length. In some embodiments, the LFO is 90 to 110 nucleotides in length. In some embodiments, the LFO is 90 to 100 nucleotides in length. In some embodiments, the LFO is 100 to 150 nucleotides in length. In some embodiments, the LFO is 100 to 140 nucleotides in length. In some embodiments, the LFO is 100 to 130 nucleotides in length. In some embodiments, the LFO is 100 to 120 nucleotides in length. In some embodiments, the LFO is 100 to 110 nucleotides in length. In some embodiments, the LFO is 110 to 150 nucleotides in length. In some embodiments, the LFO is 110 to 140 nucleotides in length. In some embodiments, the LFO is 110 to 130 nucleotides in length. In some embodiments, the LFO is 110 to 120 nucleotides in length. In some embodiments, the LFO is 120 to 150 nucleotides in length. In some embodiments, the LFO is 120 to 140 nucleotides in length. In some embodiments, the LFO is 120 to 130 nucleotides in length. In some embodiments, the LFO is 130 to 150 nucleotides in length. In some embodiments, the LFO is 130 to 140 nucleotides in length. In some embodiments, the LFO is 140 to 150 nucleotides in length.

In some embodiments, the LFO comprises a nucleotide sequence selected from the sequences in Table 2 or a loop forming portion thereof.

TABLE 2

Riboswitch Sequences

| SEQ ID NO | Sequence (5'-3') | Length |
|---|---|---|
| 2 | GAUGUAACUGAAUGAAAUGGUGAAGGACGGGUCCAAAUAGGGAAGCAACGAAGCAUAGCCUUUAUAUGGAACACUUGGGUUAUGUGGAGCUACUAGUGUAACCAGCCCUUCCUUUUGUUGAGUAGAGUGUGAGCUCCGUAACUAGUUACAUC | 152 |
| 3 | UCCAAAUAGGGAAGCAACGAAGCAUAGCCUUUAUAUGGAACACUUGGGUUAUGUGGAGCUACUAGUGUAACCAGCCCUUCCUUUUGUUGA | 92 |
| 4 | AAUAGGGAAGCAACGAAGUGGAGCUACUAGUGUAACCAGCCCUUCCUU | 48 |
| 5 | UCCAAAUAGGGAAGCAACGAAGUGGAGCUACUAGUGUAACCAGCCCUUCCUUUUGUUGA | 59 |
| 6 | UCCAAAAGGGAAGCAACGAAGUGGAGCUACUAGUGUAACCAGCCCUUUUGGA | 52 |
| 7 | AAAGGGAAGCAACGAAGUGGAGCUACUAGUGUAACCAGCCCUUU | 44 |
| 8 | GGGUUGGUGGUAAGCGAUAAUACUAAACCAUUCGCGAGAAUGGGGCGGAAAGCCUAUAGGGUCUCCCUGAGACAGCGGGUUGCCGAAAUAUCACGCGAUAU | 101 |
| 9 | GGGUUGGUGGUAAGCGAUAAUGCUAAACCAUUCGCGAGAAUGGGGCGGAAAGCCUAUAGGGUCUCCCUGAGACAGCGGGUUGCCGAAAUAUCACGCGAUAU | 101 |
| 10 | CUCCGAUAUCGACAAUACUAAACCAUCCGCGAGGGUGGGACGGAAAGCUACCAGGGUCUCUCUGAGACAGCCGGGAUGCCGAAAUAUCACAAUUUUUUUUUUUUUGUCCCGGCAUUCUUUUU | 122 |
| 11 | UCAGAUACACGACAAUACUAAACCAUCCGCGAGGAUGGGGCGAAAGCCUAAGGGUCUCCCUGAGACAGCCGGGUGCCGUGUAUCUGA | 87 |
| 12 | GGUCAGAUACACGACAAUACUAAACCAUCCGCGAGGAUGGGGCGGAAAGCCUAAGGGUCUCCCUGAGACAGCCGGGUCGCCGAAAUAUCUGAACGAUAUCAGGCCCCGGCUUUUUGU | 117 |
| 13 | GGUACACGACAAUACUAAACCAUCCGCGAGGAUGGGGCGGAAAGCCUAAGGGUCUCCCUGAGACAGCCGGGCUGCCGAAAUAUC | 84 |
| 14 | GGUCACGCACAGAGCAACCAUUCGAAAGAGUGGGACGCAAAGCCUCCGGCCUAAACCAUUGCACUCCGGUAGGUAGCGGUUACCGAUGG | 89 |
| 15 | GAUAUCGACAAUACUAAACCAUCCGCGAGGGUGGGACGAAAGCCUACAGGGUCUCUCUGAGACAGCCGGGAUGCCGAAAUAUC | 84 |
| 16 | GAUGUAACUGAAUGAAAUGGUGAAGGACGGGUCCAAAUAGGGAAGCAACGAAGCAUAGCCUUUAUAUGGACACUUGGGUUAUGUGGAGCUACUAGUGUAACCGGCCCUCCUUUUGUUGAGUAGAGUGUGAGCUCCGUAACUAGUUACAUC | 150 |
| 17 | GGUCACGCACAGGGCAAACCAUUCGAAAGAGUGGGACGCAAAGCCUCCGGCCUAAACCAUUGCACUCCGGUAGGUAGCGGGGUUACCGAUGG | 92 |

TABLE 2-continued

Riboswitch Sequences

| SEQ ID NO | Sequence (5'-3') | Length |
|---|---|---|
| 18 | AAUAGGGAAG CAACGAAGCA UAGCCUUUAU AUGGACACUU GGGUUAUGUG GAGCUACUAG UGUAACCGGC CCUCCUU | 77 |

In some embodiments, the LFO comprises a nucleotide sequence selected from the sequences in Table 2.

In some embodiments, the LFO comprises a nucleotide sequence selected from the sequences in Table 2 when converted to DNA, or a loop forming portion thereof. In some embodiments, the LFO comprises a nucleotide sequence selected from the sequences in Table 2 when converted to PNAs, or a loop forming portion thereof.

In some embodiments, the LFO comprises a nucleotide sequence of SEQ ID NO:2 or a loop forming portion thereof. In some embodiments, the LFO comprises a DNA sequence corresponding to SEQ ID NO:2 or a loop forming portion thereof. As used herein, a DNA sequence "corresponding to" a RNA sequence is a DNA sequence having a thymine base where the RNA sequence has a uracil base, but which otherwise has the same sequence of bases as the RNA sequence. In some embodiments, the LFO comprises a PNA sequence corresponding to SEQ ID NO:2 or a loop forming portion thereof. As used herein, a PNA sequence "corresponding to" a RNA sequence is a PNA sequence having a thymine base or a uracil base where the RNA sequence has a uracil base, but which otherwise has the same sequence of bases as the RNA sequence.

In some embodiments, the LFO comprises a nucleotide sequence of SEQ ID NO:3 or a loop forming portion thereof. In some embodiments, the LFO comprises a DNA sequence corresponding to SEQ ID NO:3 or a loop forming portion thereof. In some embodiments, the LFO comprises a PNA sequence corresponding to SEQ ID NO:3 or a loop forming portion thereof.

In some embodiments, the LFO comprises a nucleotide sequence of SEQ ID NO:4 or a loop forming portion thereof. In some embodiments, the LFO comprises a DNA sequence corresponding to SEQ ID NO:4 or a loop forming portion thereof. In some embodiments, the LFO comprises a PNA sequence corresponding to SEQ ID NO:4 or a loop forming portion thereof.

In some embodiments, the LFO comprises a nucleotide sequence of SEQ ID NO:5 or a loop forming portion thereof. In some embodiments, the LFO comprises a DNA sequence corresponding to SEQ ID NO:5 or a loop forming portion thereof. In some embodiments, the LFO comprises a PNA sequence corresponding to SEQ ID NO:5 or a loop forming portion thereof.

In some embodiments, the LFO comprises a nucleotide sequence of SEQ ID NO:6 or a loop forming portion thereof. In some embodiments, the LFO comprises a DNA sequence corresponding to SEQ ID NO:6 or a loop forming portion thereof. In some embodiments, the LFO comprises a PNA sequence corresponding to SEQ ID NO:6 or a loop forming portion thereof.

In some embodiments, the LFO comprises a nucleotide sequence of SEQ ID NO:7 or a loop forming portion thereof. In some embodiments, the LFO comprises a DNA sequence corresponding to SEQ ID NO:7 or a loop forming portion thereof. In some embodiments, the LFO comprises a PNA sequence corresponding to SEQ ID NO:7 or a loop forming portion thereof.

In some embodiments, the LFO comprises a nucleotide sequence of SEQ ID NO:8 or a loop forming portion thereof. In some embodiments, the LFO comprises a DNA sequence corresponding to SEQ ID NO:8 or a loop forming portion thereof. In some embodiments, the LFO comprises a PNA sequence corresponding to SEQ ID NO:8 or a loop forming portion thereof.

In some embodiments, the LFO comprises a nucleotide sequence of SEQ ID NO:9 or a loop forming portion thereof. In some embodiments, the LFO comprises a DNA sequence corresponding to SEQ ID NO:9 or a loop forming portion thereof. In some embodiments, the LFO comprises a PNA sequence corresponding to SEQ ID NO:9 or a loop forming portion thereof.

In some embodiments, the LFO comprises a nucleotide sequence of SEQ ID NO:10 or a loop forming portion thereof. In some embodiments, the LFO comprises a DNA sequence corresponding to SEQ ID NO: 10 or a loop forming portion thereof. In some embodiments, the LFO comprises a PNA sequence corresponding to SEQ ID NO: 10 or a loop forming portion thereof.

In some embodiments, the LFO comprises a nucleotide sequence of SEQ ID NO:11 or a loop forming portion thereof. In some embodiments, the LFO comprises a DNA sequence corresponding to SEQ ID NO: 11 or a loop forming portion thereof. In some embodiments, the LFO comprises a PNA sequence corresponding to SEQ ID NO: 11 or a loop forming portion thereof.

In some embodiments, the LFO comprises a nucleotide sequence of SEQ ID NO: 12 or a loop forming portion thereof. In some embodiments, the LFO comprises a DNA sequence corresponding to SEQ ID NO: 12 or a loop forming portion thereof. In some embodiments, the LFO comprises a PNA sequence corresponding to SEQ ID NO: 12 or a loop forming portion thereof.

In some embodiments, the LFO comprises a nucleotide sequence of SEQ ID NO: 13 or a loop forming portion thereof. In some embodiments, the LFO comprises a DNA sequence corresponding to SEQ ID NO: 13 or a loop forming portion thereof. In some embodiments, the LFO comprises a PNA sequence corresponding to SEQ ID NO: 13 or a loop forming portion thereof.

In some embodiments, the LFO comprises a nucleotide sequence of SEQ ID NO: 14 or a loop forming portion thereof. In some embodiments, the LFO comprises a DNA sequence corresponding to SEQ ID NO: 14 or a loop forming portion thereof. In some embodiments, the LFO comprises a PNA sequence corresponding to SEQ ID NO: 14 or a loop forming portion thereof.

In some embodiments, the LFO comprises a nucleotide sequence of SEQ ID NO:15 or a loop forming portion thereof. In some embodiments, the LFO comprises a DNA sequence corresponding to SEQ ID NO: 15 or a loop forming portion thereof. In some embodiments, the LFO comprises a PNA sequence corresponding to SEQ ID NO: 15 or a loop forming portion thereof.

In some embodiments, the LFO comprises a nucleotide sequence of SEQ ID NO: 16 or a loop forming portion thereof. In some embodiments, the LFO comprises a DNA sequence corresponding to SEQ ID NO: 16 or a loop forming portion thereof. In some embodiments, the LFO comprises a PNA sequence corresponding to SEQ ID NO: 16 or a loop forming portion thereof.

In some embodiments, the LFO comprises a nucleotide sequence of SEQ ID NO:17 or a loop forming portion thereof. In some embodiments, the LFO comprises a DNA sequence corresponding to SEQ ID NO: 17 or a loop forming portion thereof. In some embodiments, the LFO comprises a PNA sequence corresponding to SEQ ID NO: 17 or a loop forming portion thereof.

In some embodiments, the LFO comprises a nucleotide sequence of SEQ ID NO:18 or a loop forming portion thereof. In some embodiments, the LFO comprises a DNA sequence corresponding to SEQ ID NO: 18 or a loop forming portion thereof. In some embodiments, the LFO comprises a PNA sequence corresponding to SEQ ID NO: 18 or a loop forming portion thereof.

6.1.6. Anchors

A CDN binding moiety or an additional cargo moiety can be covalently bound to an amphipathic or apolar moiety to facilitate coupling of the CDN binding moiety or additional cargo moiety to a complex of the disclosure. Amphipathic and apolar moieties can interact with apolar regions in complexes of the disclosure, thereby anchoring CDN binding moieties and additional cargo moieties attached to amphipathic and apolar moieties to the complexes.

Amphipathic moieties that can be used as anchors include lipids (e.g., as described in Section 6.1.4.1) and fatty acids (e.g., as described in Section 6.1.4.3). In some embodiments, the anchors comprise a sterol or a sterol derivative e.g., a plant sterol, an animal sterol, or a sterol derivative such as a vitamin). For example, sterols such as cholesterol can be covalently bound to a cargo moiety (e.g., via the hydroxyl group at the 3-position of the A-ring of the sterol) and used to anchor the CDN binding moiety or additional cargo moiety to a complex of the disclosure. Apolar moieties that can be used as anchors include alkyl chains, acyl chains, and diacyl chains. CDN binding moieties and additional cargo moieties can be covalently bound to anchor moieties directly or indirectly via a linker (e.g., via a difunctional peptide or other linker described in Section 6.1.7). Cargo moieties that are biologically active may retain their biological activity while covalently bound to the anchor (or linker attached to the anchor), while others may require cleavage of the covalent bond (e.g., by hydrolysis) attaching the cargo moiety to the anchor (or linker attached to the anchor) to regain biological activity.

In some embodiments, at least one CDN binding moiety is coupled to an anchor. In some embodiments, the anchor comprises an amphipathic and/or apolar moiety. In some embodiments, the anchor comprises an amphipathic moiety. In some embodiments, the amphipathic moiety comprises one of the amphipathic molecules in the complex. In some embodiments, the amphipathic moiety comprises a lipid, a detergent, a fatty acid, an apolar molecule attached to a sugar, or a sterol attached to a sugar.

In some embodiments, the amphipathic moiety comprises a sterol. In some embodiments, the sterol comprise an animal sterol or a plant sterol. In some embodiments, the sterol comprises cholesterol.

In other embodiments, the anchor comprises an apolar moiety. In some embodiments, the apolar moiety comprises an alkyl chain, an acyl chain, or a diacyl chain.

In some embodiments, the CDN binding moiety is coupled to the anchor by a direct bond.

In some embodiments, the CDN binding moiety is coupled to the anchor by a linker.

6.1.7. Linkers

Linkers comprise a chain of atoms that covalently attach CDN binding moiety or additional cargo moieties to other moieties in a complex of the disclosure, for example to apolipoprotein molecules, amphipathic molecules, and anchors. A number of linker molecules are commercially available, for example from ThermoFisher Scientific. Suitable linkers are well known to those of skill in the art and include, but are not limited to, straight or branched-chain carbon linkers, heterocyclic carbon linkers, and peptide linkers. A linker can be a bifunctional linker, which is either homobifunctional or heterobifunctional.

Suitable linkers include cleavable and non-cleavable linkers.

A linker may be a cleavable linker, facilitating release of a CDN binding moiety or additional cargo moiety in vivo. Cleavable linkers include acid-labile linkers (e.g., comprising hydrazine or cis-aconityl), protease-sensitive (e.g., peptidase-sensitive) linkers, photolabile linkers, or disulfide-containing linkers (Chari et al., 1992, Cancer Research 52:127-131; U.S. Pat. No. 5,208,020). A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker.

A cleavable linker can be pH-sensitive, i.e., sensitive to hydrolysis at certain pH values. Typically, a pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661). Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the cargo moiety via an acylhydrazone bond (see, e.g., U.S. Pat. No. 5,622,929).

In some embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio) propionate), SPDB (N-succinimidyl-3-(2-pyridyldithio) butyrate) and SMPT (N-succinimidyloxycarbonyl-alpha-methyl-alpha-(2-pyridyl-dithio) toluene), SPDB and SMPT (see, e.g., Thorpe et al., 1987, Cancer Res. 47:5924-5931; Wawrzynczak et al., In *Immunoconjugates: Antibody Conjugates in Radioimag-* ery and Therapy of Cancer (C. W. Vogel ed., Oxford U. Press, 1987. See also, U.S. Pat. No. 4,880,935).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). In some embodiments, the peptidyl linker cleavable by an intracellular protease is a Val-Cit linker or a Phe-Lys linker.

In some embodiments, the linker is a malonate linker (Johnson et al., 1995, Anticancer Res. 15:1387-93), a maleimidobenzoyl linker (Lau et al., 1995, *Bioorg-Med-Chem.* 3 (10): 1299-1304), or a 3'-N-amide analog (Lau et al., 1995, *Bioorg-Med-Chem.* 3 (10): 1305-12).

In other embodiments, the linker unit is not cleavable and the CDN binding moiety or additional cargo moiety is released, for example, by complex degradation. Exemplary non-cleavable linkers include maleimidocaproyl, N-succinimidyl 4-(maleimidomethyl) cyclohexanecarboxylate (SMCC) and N-succinimidyl-4-(iodoacetyl)-aminobenzoate (SIAB).

In some embodiments, a CDN binding moiety is coupled to an anchor (e.g., as described in Section 6.1.6) by a linker. In some embodiments, the linker coupling the CDN binding moiety to the anchor is a bifunctional linker. In some embodiments, the linker coupling the CDN binding moiety to the anchor is a cleavable linker. In some embodiments, the cleavable linker is a dipeptide linker such as a valine-citrulline (val-cit) or a phenylalanine-lysine (phe-lys) linker. In some embodiments, the linker coupling the CDN binding moiety to the anchor is a non-cleavable linker. Exemplary non-cleavable linkers include maleimidocaproyl, N-succinimidyl 4-(maleimidomethyl) cyclohexanecarboxylate (SMCC) and N-succinimidyl-4-(iodoacetyl)-aminobenzoate (SIAB).

6.1.8. Cyclic Dinucleotides (CDNs)

Complexes of the disclosure can carry one or more CDNs as cargo moieties. The CDNs can be non-covalently bound to one or more CDN binding moieties. CDNs can be naturally occurring or synthetic. CDNs can also be in the form of prodrugs (e.g., 2'-O substituted prodrug analogs). Exemplary CDNs are described in Corrales et al., 2015, Cell Reports, 11:1-13, Bose et al., 2016, Cell Chemical Biology, 23:11539-1549, Opoku-Temeng et al., 2016, Chem. Commun., 52:9327-9343, Nelson et al., 2015, PNAS, 112 (17): 5389-5394, Fu et al., 2015, Science Translational Medicine, 7 (283): ra52, WO 2014/093936, WO 2014/099824, WO 2014/189805, WO 2015/017652, WO 2015/185565, WO 2016/096174, WO 2016/120305, WO 2018/060323, U.S. Pat. Nos. 7,709,458, and 7,592,326, the contents of each of which are incorporated herein by reference in their entireties.

In some embodiments, a complex of the disclosure includes at least one CDN comprising two naturally occurring nucleobases. In some embodiments, the naturally occurring nucleobases are independently selected from adenine, guanine, cytosine, thymine, uracil, 5-methylcytosine, pseudouridine, dihydrouridine, inosine, 7-methylguanine, hypoxanthine, xanthine, 5,6-dihydrouracil, and 5-hydroxymethylcytosine. In some embodiments, the naturally occurring nucleobases are independently selected from adenine, guanine, cytosine, thymine, and uracil. In some embodiments, the naturally occurring nucleobases are independently selected from adenine and guanine.

In some embodiments, a complex of the disclosure includes at least one CDN comprising one or two non-naturally occurring nucleobases. In some embodiments, at least one CDN comprises one non-naturally occurring nucleobase and one naturally occurring nucleobase. In some embodiments, the naturally occurring nucleobase is selected from adenine, guanine, cytosine, thymine, uracil, 5-methylcytosine, pseudouridine, dihydrouridine, inosine, 7-methylguanine, hypoxanthine, xanthine, 5,6-dihydrouracil, and 5-hydroxymethylcytosine. In some embodiments, the naturally occurring nucleobase is selected from adenine, guanine, cytosine, thymine, and uracil. In some embodiments, the naturally occurring nucleobase is selected from adenine and guanine. In some embodiments, at least one CDN comprises two non-naturally occurring nucleobases.

In some embodiments, a complex of the disclosure includes at least one CDN comprising a stable isotope, such as deuterium.

In some embodiments, a complex of the disclosure includes at least one CDN comprising a radioisotope, such as Carbon-14 or tritium.

In some embodiments, a complex of the disclosure comprises at least one CDN of Formula I:

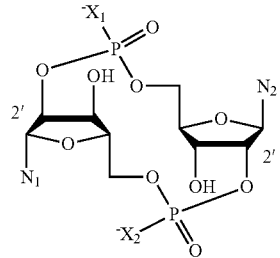

Formula I where $N_1$ and $N_2$ are each an individually selected nucleobase, and $X_1$ and $X_2$ are each individually O or S.

In some embodiments, a complex of the disclosure comprises at least one CDN of Formula II:

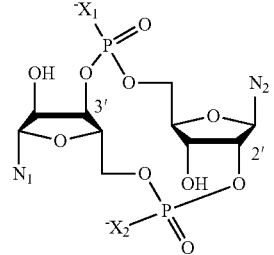

Formula II where $N_1$ and $N_2$ are each an individually selected nucleobase, and $X_1$ and $X_2$ are each individually O or S.

In some embodiments, a complex of the disclosure comprises at least one CDN of Formula III:

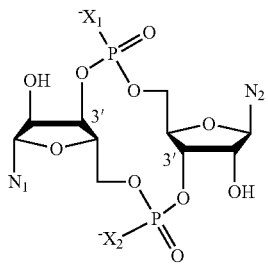

Formula III where $N_1$ and $N_2$ are each an individually selected nucleobase, and $X_1$ and $X_2$ are each individually O or S.

In some embodiments of Formula I, II, and III, $X_1$ is O.
In some embodiments of Formula I, II, and III, $X_1$ is S.
In some embodiments of Formula I, II, and III, $X_2$ is O.
In some embodiments of Formula I, II, and III, $X_2$ is S.
In some embodiments of Formula I, II, and III, $N_1$ and $N_2$ are each independently selected from adenine, guanine, cytosine, thymine, uracil, 5-methylcytosine, pseudouridine, dihydrouridine, inosine, 7-methylguanine, hypoxanthine, xanthine, 5,6-dihydrouracil, and 5-hydroxymethylcytosine.
In some embodiments of Formula I, II, and III, $N_1$ and $N_2$ are each independently selected from adenine, guanine, cytosine, thymine, and uracil.
In some embodiments of Formula I, II, and III, $N_1$ and $N_2$ are each individually selected from guanine and adenine.

In some embodiments of Formula I, II, and III, $N_1$ is guanine.
In some embodiments of Formula I, II, and III, $N_1$ is adenine.
In some embodiments of Formula I, II, and III, $N_2$ is guanine.
In some embodiments of Formula I, II, and III, $N_2$ is adenine.
In some embodiments, at least one CDN is a naturally occurring CDN.
In some embodiments, a complex of the disclosure includes at least one non-naturally occurring CDN.
In some embodiments, a complex of the disclosure includes at least one non-naturally occurring CDN comprising one or two thio substituted phosphate linkages.
In some embodiments, a complex of the disclosure comprises cGAMP, c-di-GMP, or c-di-AMP. In some embodiments, a complex of the disclosure comprises cGAMP. In some embodiments, a complex of the disclosure comprises c-di-GMP. In some embodiments, a complex of the disclosure comprises c-di-AMP.
In some embodiments a complex of the disclosure comprises at least one CDN as described in WO 2014/093936. For example, a complex can comprise at least one CDN selected from c-di-AMP thiophosphate, c-di-GMP thiophosphate, c-di-IMP thiophosphate, c-AMP-GMP thiophosphate, c-AMP-IMP thiophosphate, and c-GMP-IMP thiophosphate.
In some embodiments, a complex of the disclosure comprises at least one CDN selected from those shown in Table 3:

TABLE 3

| | CDN |
|---|---|
| 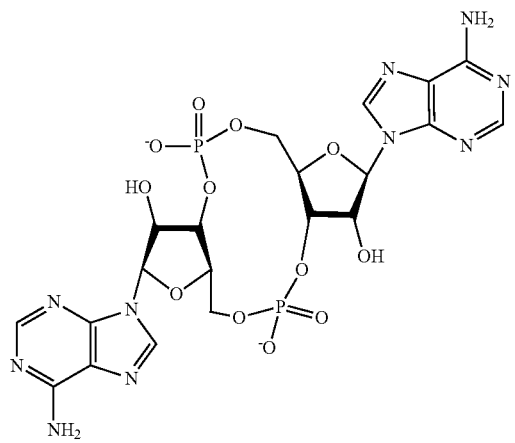 | 3-1 |
| 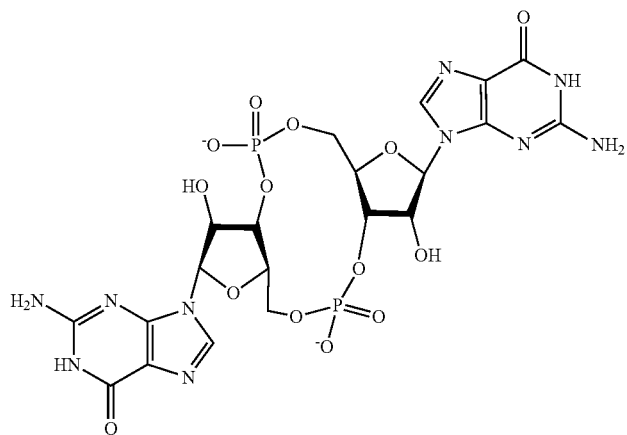 | 3-2 |

TABLE 3-continued
| | CDN |
|---|---|
| 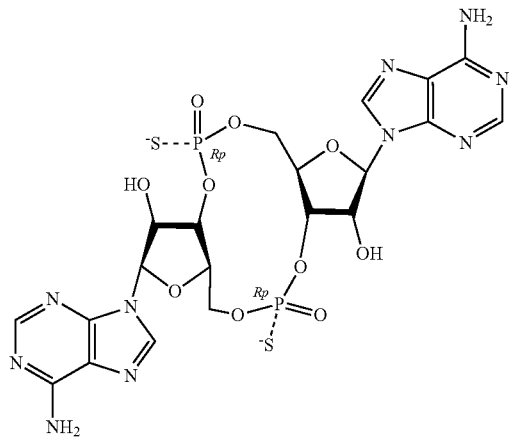 | 3-3 |
| 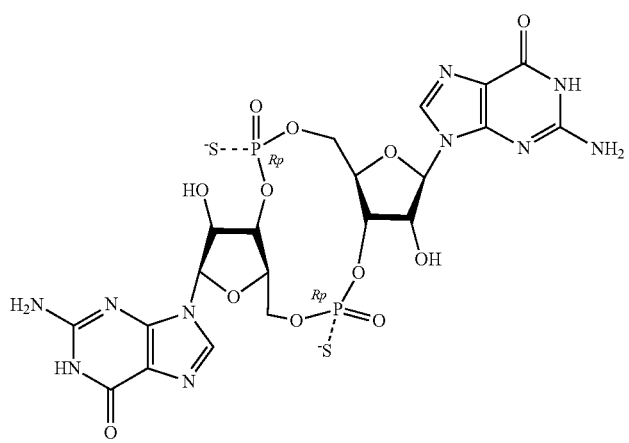 | 3-4 |
| 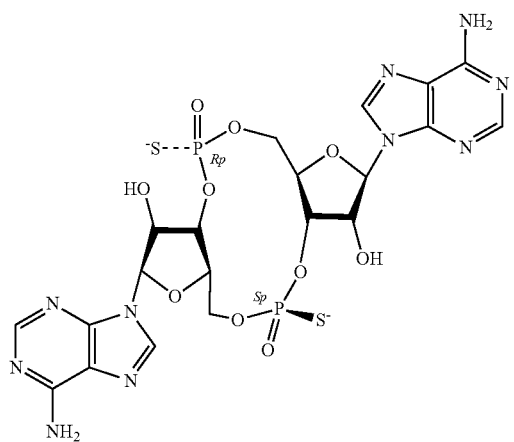 | 3-5 |

TABLE 3-continued
| | CDN |
|---|---|
| 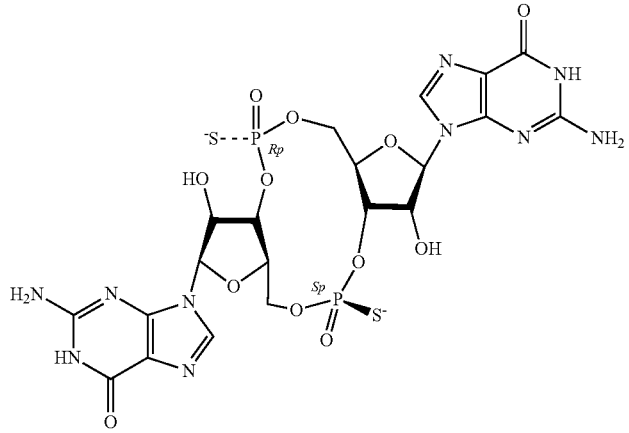 | 3-6 |
| 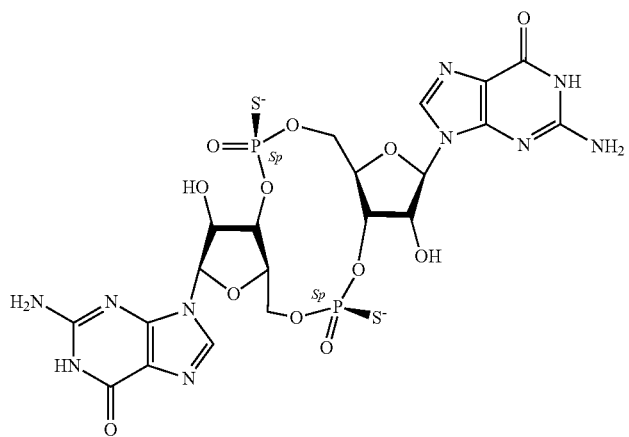 | 3-7 |
| 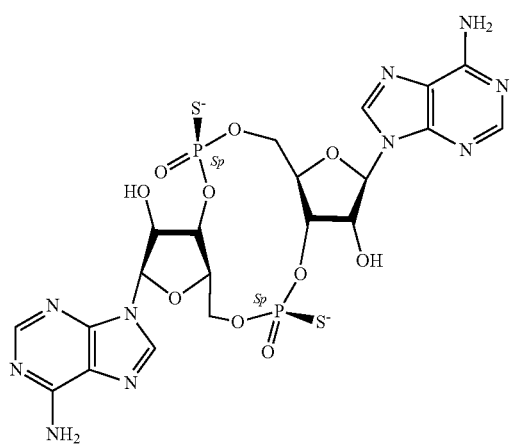 | 3-8 |

TABLE 3-continued

| | CDN |
|---|---|
| 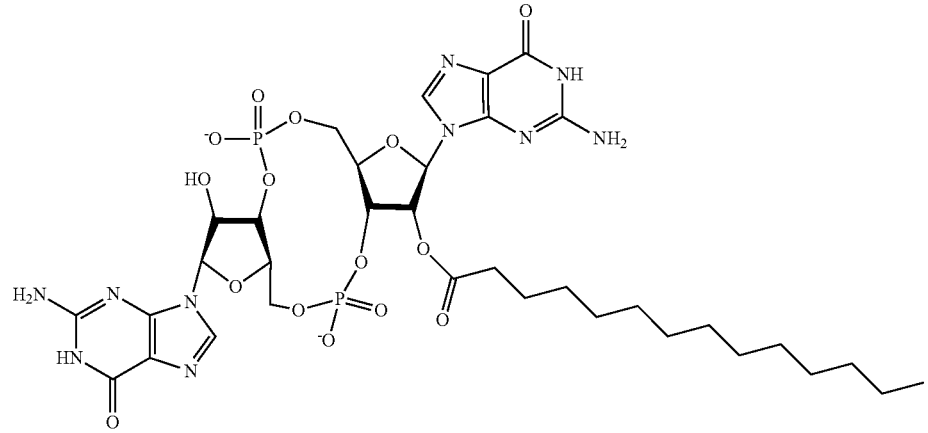 | 3-9 |
| 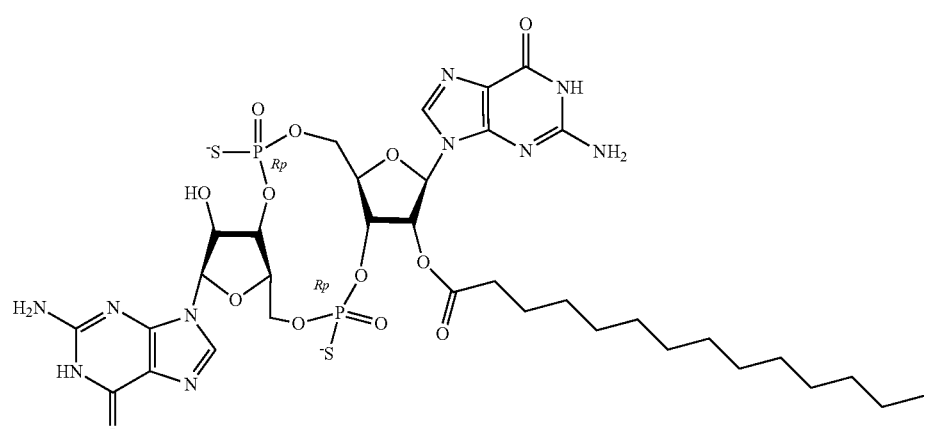 | 3-10 |

In some embodiments a complex of the disclosure comprises at least one CDN as described in WO 2014/099824. For example, a complex can comprise one or more cGAMPs selected from 2'3'-cGAMP, 2'2-cGAMP, 3'2'-cGAMP and 3'3-cGAMP.

In some embodiments a complex of the disclosure comprises at least one CDN as described in WO 2014/189805. For example, a complex of the disclosure can comprise at least one CDN having the following structure:

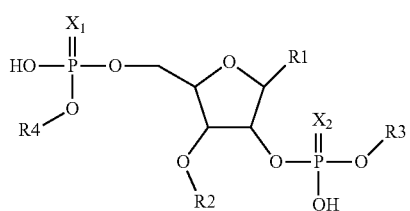

covalently linked to

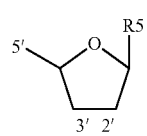

wherein $R^3$ is a covalent bond to the 5' carbon of (b),
R4 is a covalent bond to the 2' or 3' carbon of (b),
R1 is a purine linked through its $N_9$ nitrogen to the ribose ring of (a),
R5 is a purine linked through its $N_9$ nitrogen to the ribose ring of (b), each of $X_1$ and $X_2$ are independently O or S,
R2 is H or an optionally substituted straight chain alkyl of from 1 to 18 carbons and from 0 to 3 heteroatoms, an optionally substituted alkenyl of from 1-9 carbons, an optionally substituted alkynyl of from 1-9 carbons, or an optionally substituted aryl, wherein substitution(s), when present, may be independently selected from the group consisting of $C_{1-6}$ alkyl straight or branched chain, benzyl, halogen, trihalomethyl, $C_{1-6}$ alkoxy, —$NO_2$, —$NH_2$, —OH, =O, —COOR' where R' is H or lower alkyl, —$CH_2OH$, and —$CONH_2$, and the 2' or 3' carbon of (b) which is not in a covalent bond with (a) is —O—R6, wherein R6 is H or an optionally substituted straight chain alkyl of from 1 to 18 carbons and from 0 to 3 heteroatoms, an optionally substituted alkenyl of from 1-9 carbons, an optionally substituted alkynyl of from 1-9 carbons, or an optionally substituted aryl, wherein substitution(s), when present, may be independently selected from the group consisting of $C_{1-6}$ alkyl straight or branched chain, benzyl, halogen, trihalomethyl, $C_{1-6}$ alkoxy, —$NO_2$, —$NH_2$, —OH, =O, —COOR' where R' is H or lower alkyl, —$CH_2OH$, and —$CONH_2$, or a prodrug or a pharmaceutically acceptable salt thereof.

In some embodiments, a complex of the disclosure comprises at least one CDN selected from those shown in FIG. 4, FIG. 5, and FIG. 6 of WO 2014/189805.

In some embodiments a complex of the disclosure comprises at least one CDN as described in WO 2015/185565. For example, a complex of the disclosure can comprise a CDN having the following structure:

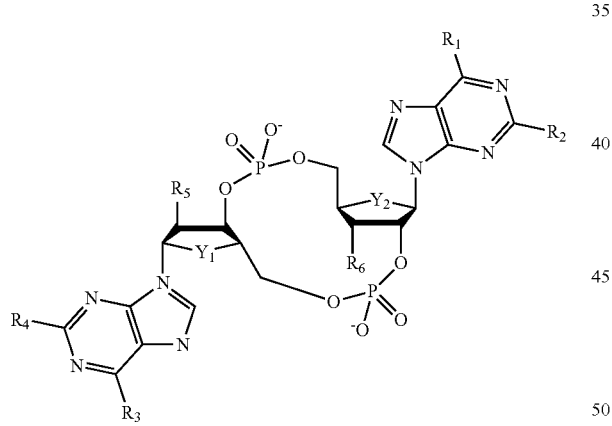

wherein:

$Y^1$ and $Y^2$ are independently $CH_2$ or O, $R_1$ is OH and $R_2$ is $NH_2$ or $R^1$ is $NH_2$ and $R^2$ is H;

$R_3$ is OH and Ra is $NH_2$ or $R_3$ is $NH_2$ and $R^4$ is H;

$R_5$ =OH or F;

$R_6$=OH or F;

and when both $R_5$ and $R_6$ are OH, at least one of $Y_1$ and $Y_2$ is $CH_2$.

In some embodiments, a complex of the disclosure comprises one or more CDNs selected from the compounds shown in Table 4:

TABLE 4

| | CDN |
|---|---|
| 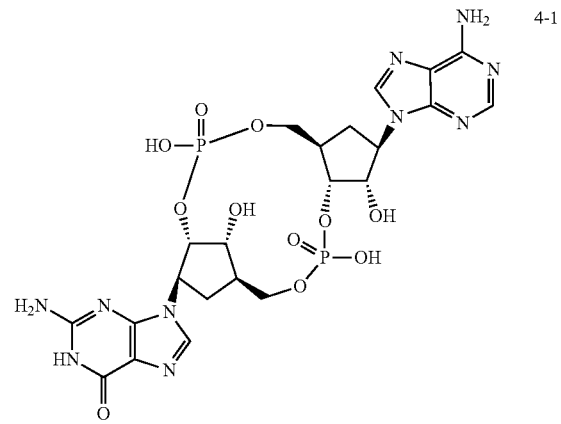 | 4-1 |
| 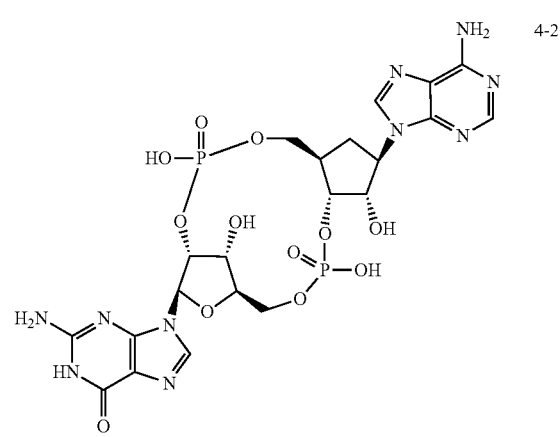 | 4-2 |
| 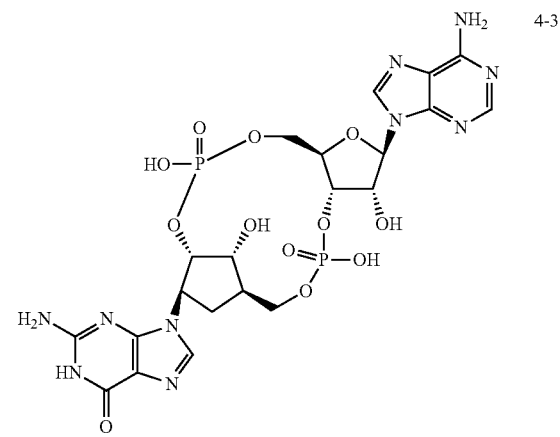 | 4-3 |

TABLE 4-continued

| | CDN |
|---|---|
| 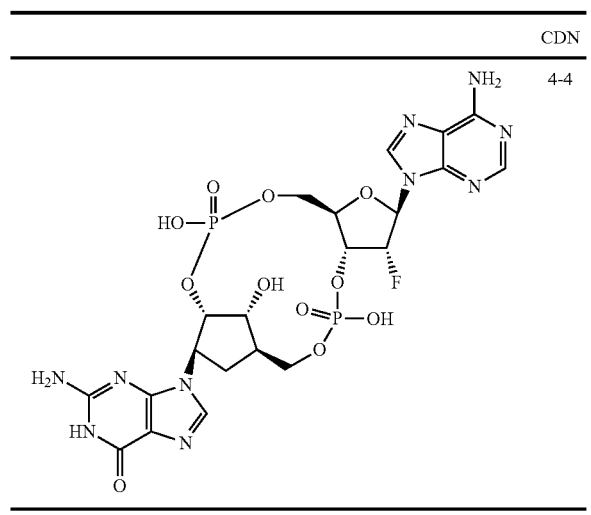 | 4-4 |

In some embodiments a complex of the disclosure comprises at least one CDN as described in WO 2016/096174. For example, a complex can comprise a CDN having the following structure:

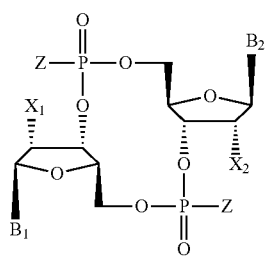

wherein:

$X_1$ is H or F;

$X_2$ is H or F;

at least one among $X_1$ and $X_2$ is a fluorine atom;

Z is OH, $OR_1$, SH or $SR_1$, wherein:
  i) $R_1$ is Na or $NH_4$, or
  ii) $R_1$ is an enzyme-labile group which provides OH or SH in vivo such as pivaloyloxymethyl;

$B_1$ and $B_2$ are bases chosen adenine, guanine and hypoxanthine, where $B_1$ is a different base than $B_2$, or a pharmaceutically acceptable salt thereof.

In some embodiments, a complex of the disclosure comprises one or more CDNs selected from the compounds shown in Table 5:

TABLE 5

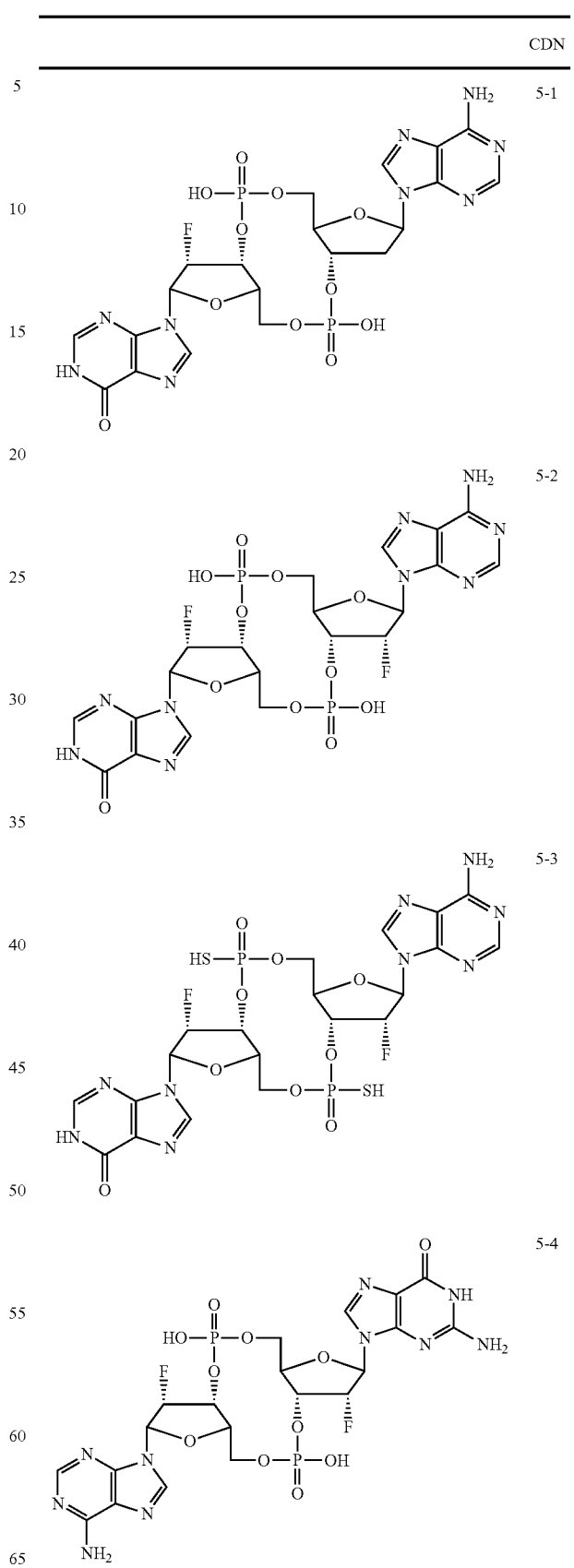

TABLE 5-continued

CDN

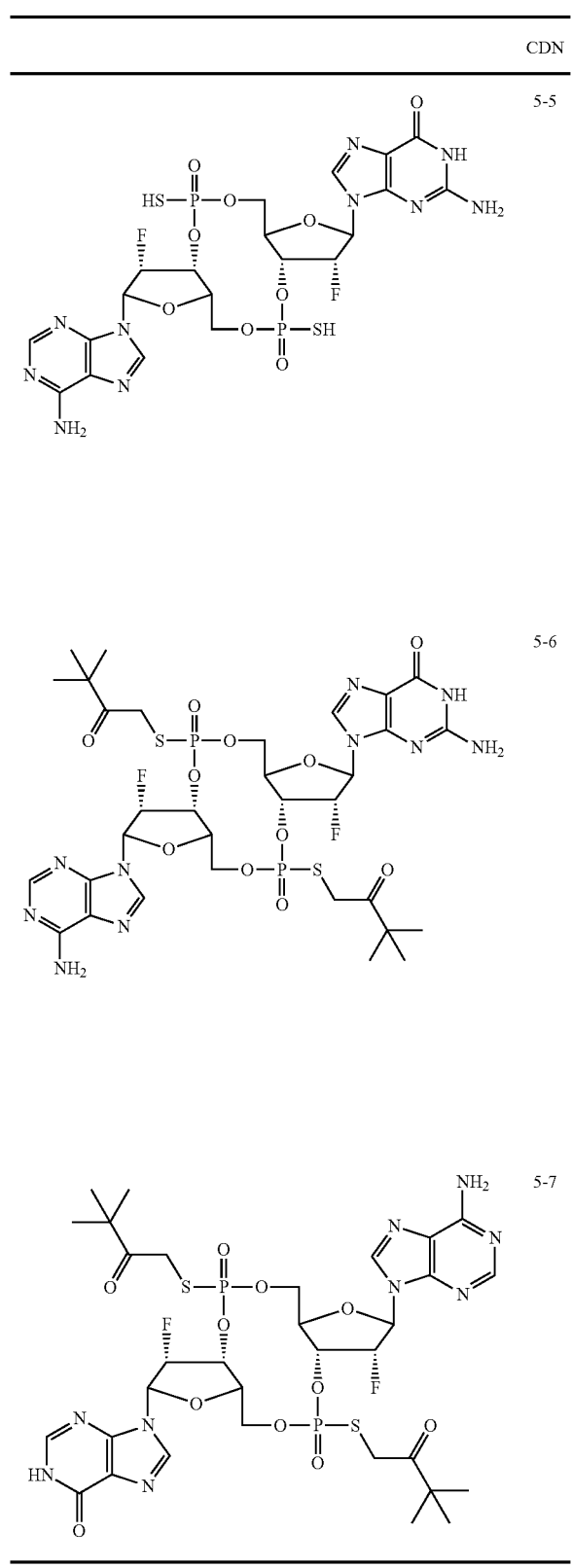

5-5

5-6

5-7

In some embodiments a complex of the disclosure comprises at least one CDN as described in WO 2016/120305. For example, a complex can comprise a CDN having the following structure:

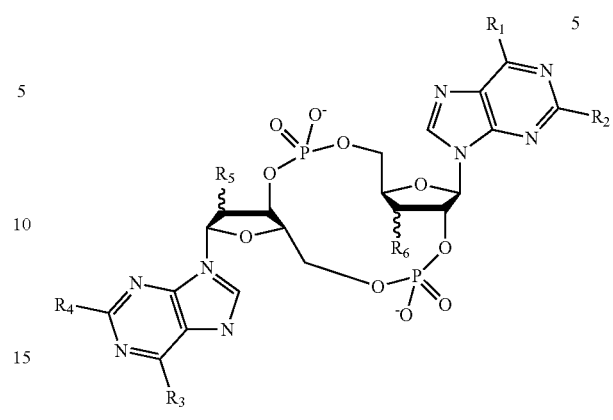

wherein

R₁ is OH and R₂ is NH₂ or R₂ is NH₂ and R₂ is H;
R₃ is OH and R₄ is NH₂ or R₃ is NH₂ and R₄ is H;
one of R₅ and R₆ is F or OH,
or a pharmaceutically acceptable salt thereof.

In some embodiments, a complex of the disclosure comprises one or more CDNs selected from the compounds shown in Table 6:

TABLE 6

CDN

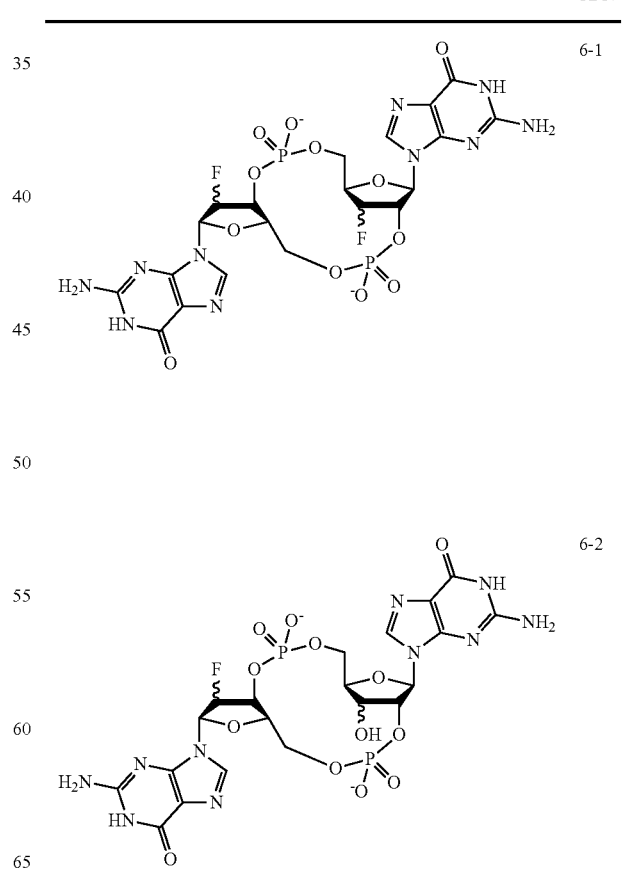

6-1

6-2

TABLE 6-continued
| | CDN |
|---|---|
| 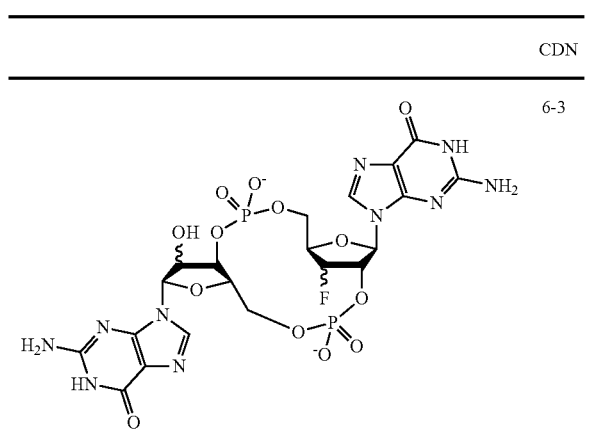 | 6-3 |
| 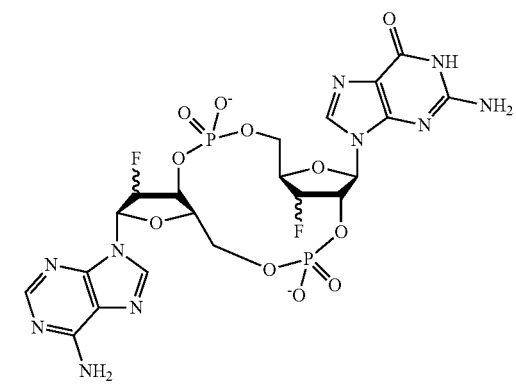 | 6-4 |
| 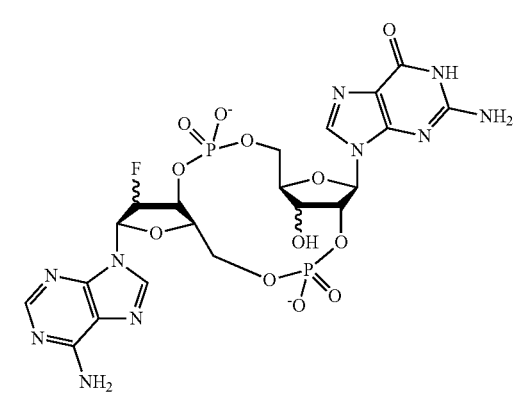 | 6-5 |
| 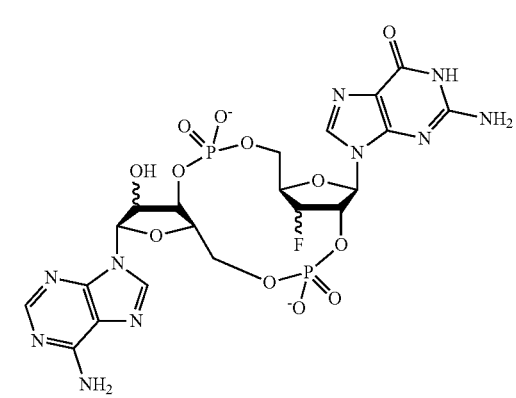 | 6-6 |
TABLE 6-continued
| | CDN |
|---|---|
| 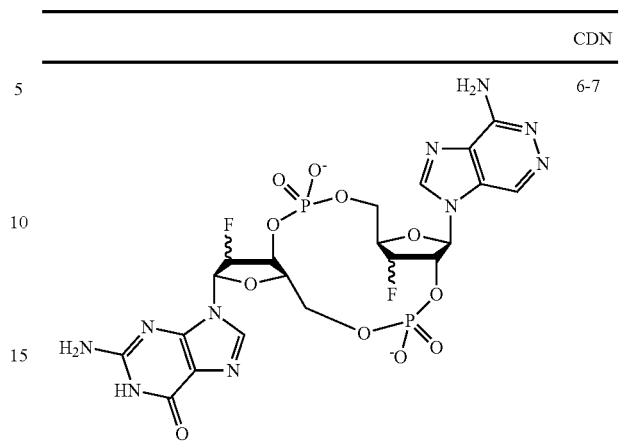 | 6-7 |
| 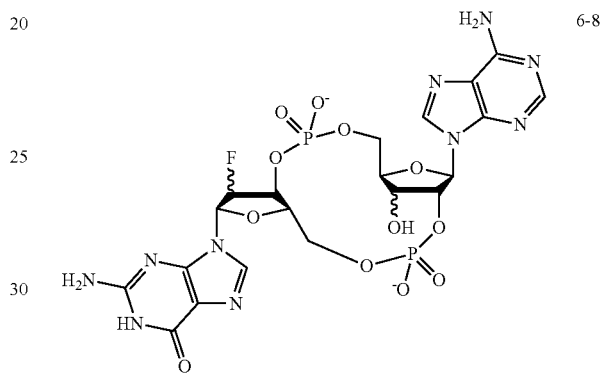 | 6-8 |
| 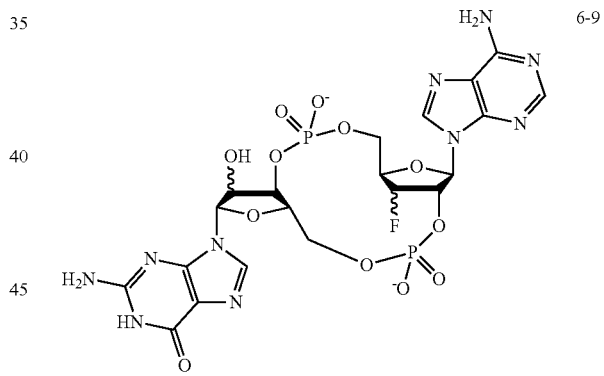 | 6-9 |
| 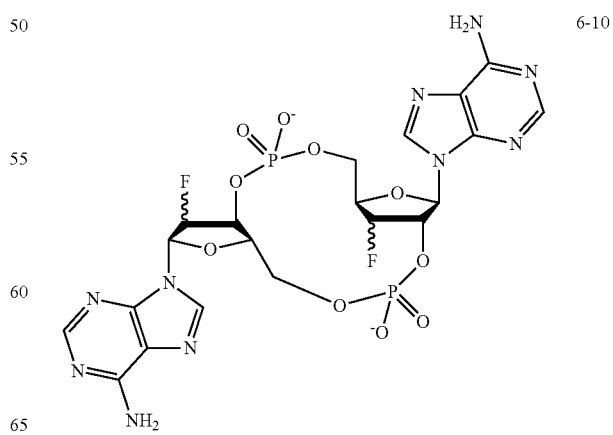 | 6-10 |

TABLE 6-continued

| CDN |
|---|
| 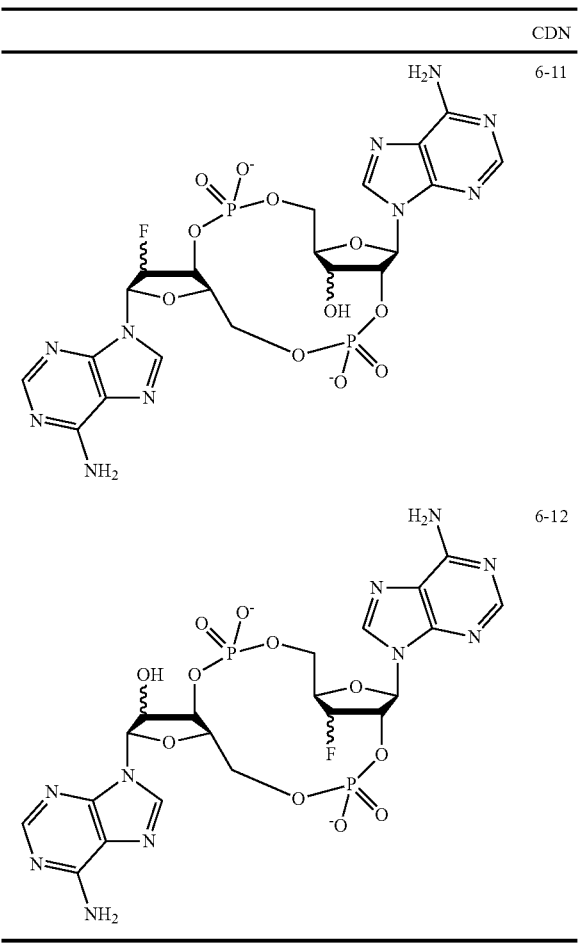 6-11 <br> 6-12 |

In some embodiments a complex of the disclosure comprises at least one CDN as described in WO 2018/060323. For example, a complex can comprise a CDN having the following structure:

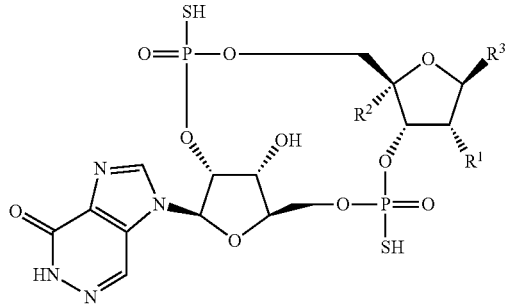

wherein

R$^1$ is selected from the group consisting of H, F, —O—C$_{1-3}$alkyl and OH, and R$^2$ is H, or R$^2$ is —CH$_2$— and R$^1$ is —O—, forming together a —CH$_2$—O— bridge, and R$^3$ is a purine nucleobase selected from the group consisting of purine, adenine, guanine, xanthine, hypoxanthine, connected through its N$^9$ nitrogen, or a salt thereof.

In some embodiments, a complex of the disclosure comprises one or more CDNs selected from the compounds shown in Table 7:

TABLE 7

| CDN |
|---|
| 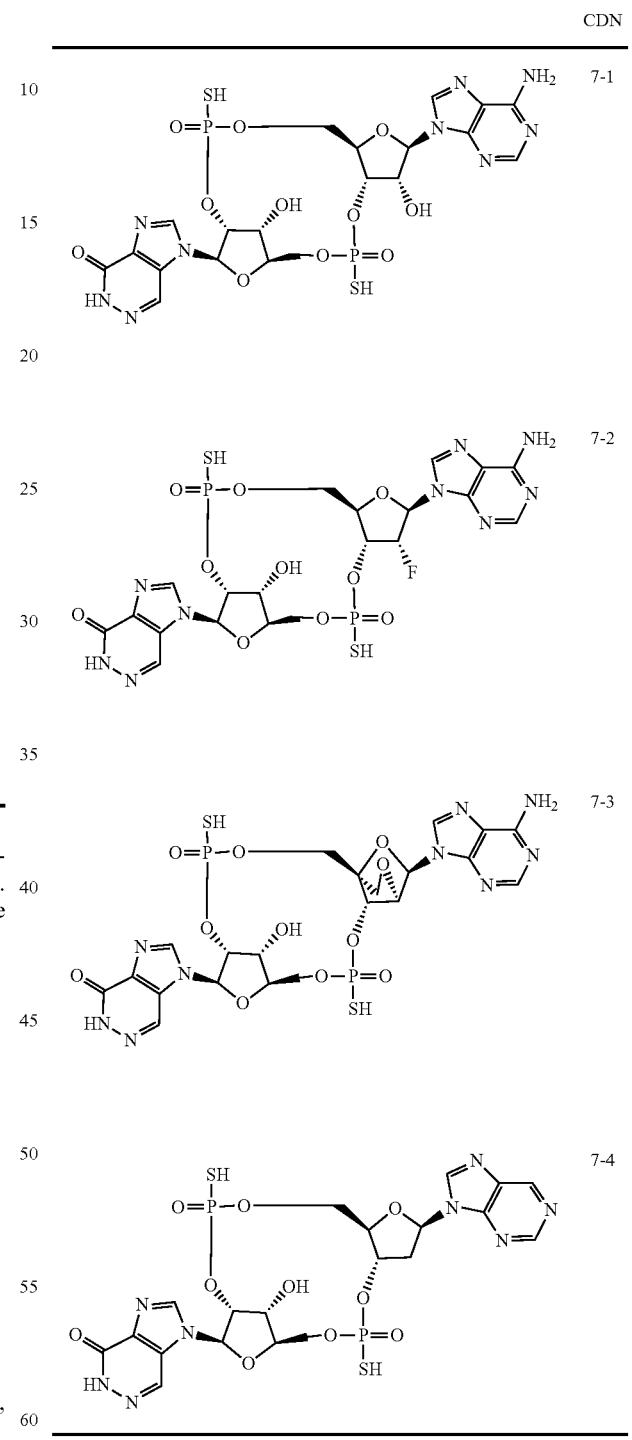 7-1 <br> 7-2 <br> 7-3 <br> 7-4 |

In some embodiments a complex of the disclosure comprises at least one CDN as described in U.S. Pat. No. 7,709,458.

In some embodiments, a complex can comprise one or more CDNs selected from the compounds shown in Table 8:

TABLE 8
| | CDN |
|---|---|
| 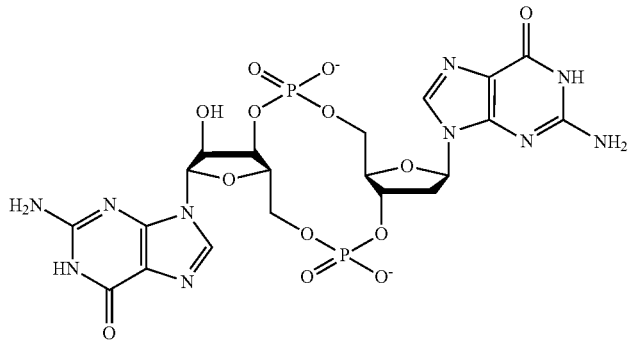 | 8-1 |
| 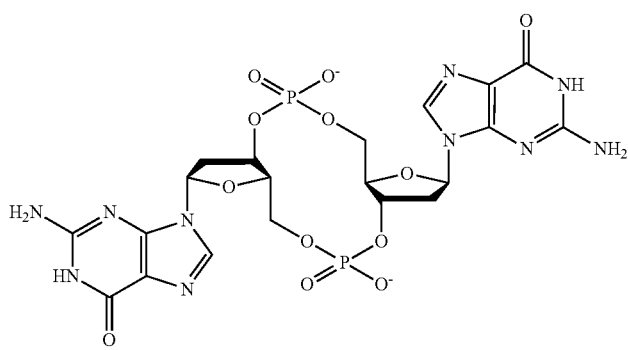 | 8-2 |
| 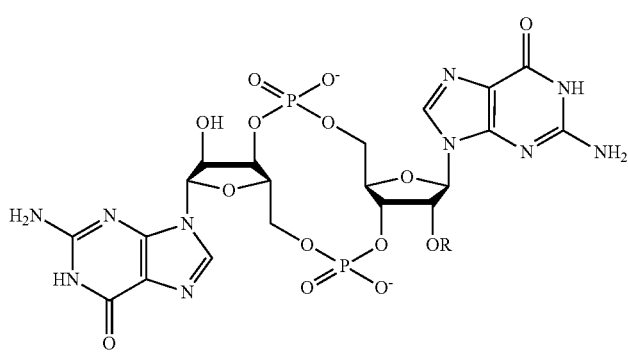 R = CH₃ or C₂H₅ | 8-3 |
| 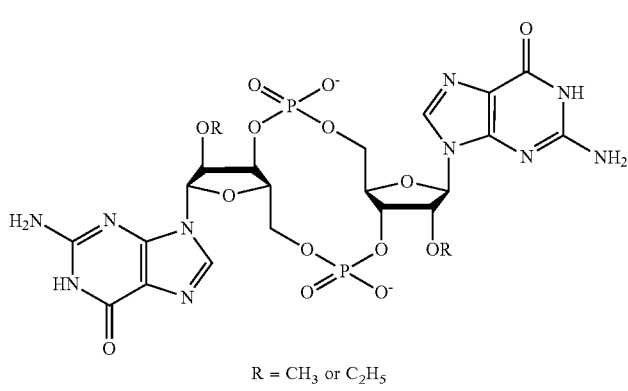 R = CH₃ or C₂H₅ | 8-4 |

TABLE 8-continued
| | CDN |
|---|---|
| 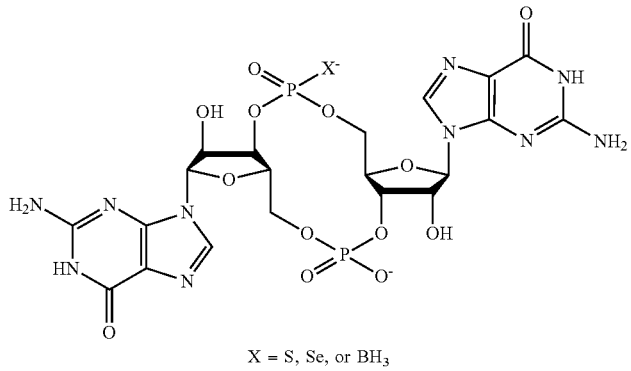<br>X = S, Se, or BH$_3$ | 8-5 |
| 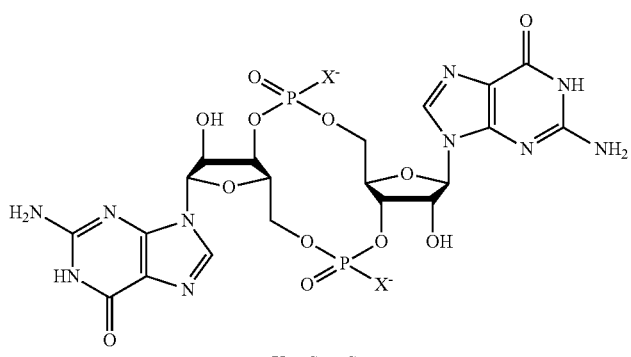<br>X = S or Se | 8-6 |
| 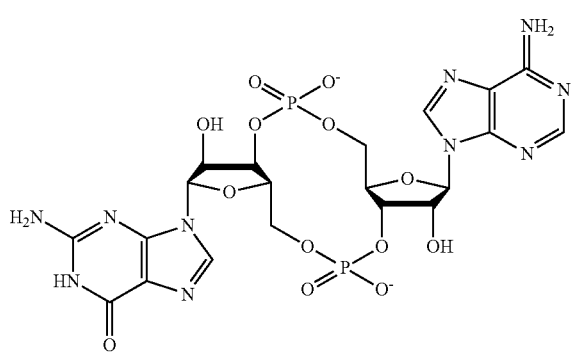 | 8-7 |
| 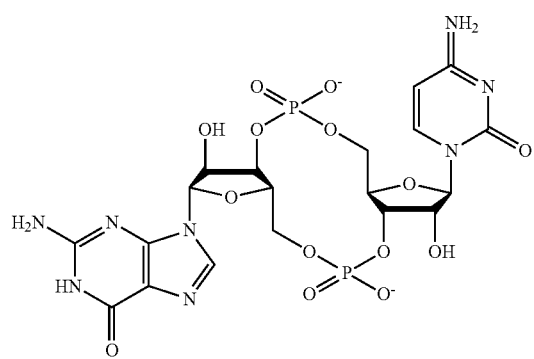 | 8-8 |

TABLE 8-continued
| | CDN |
|---|---|
| 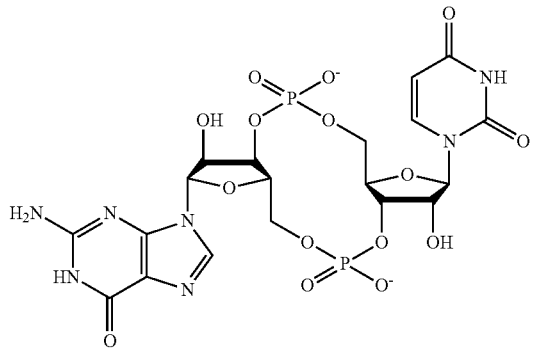 | 8-9 |
| 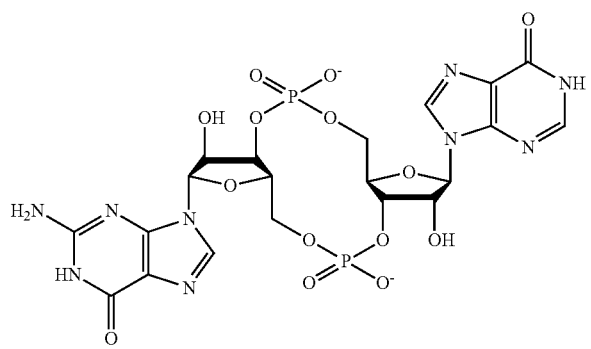 | 8-10 |
| 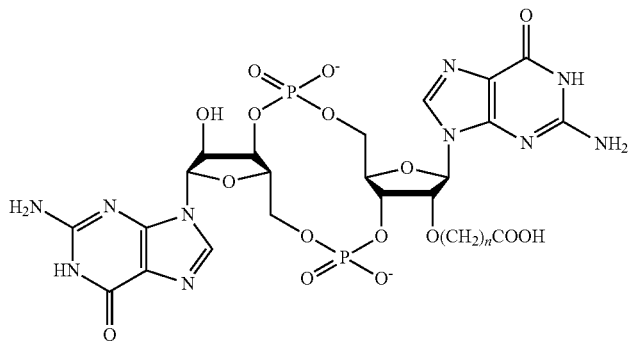 n = 1-5 | 8-11 |
| 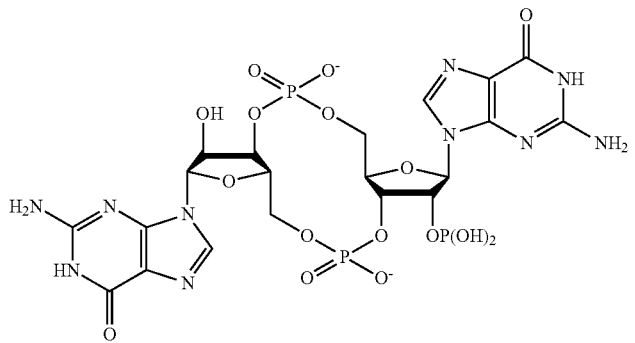 | 8-12 |

TABLE 8-continued
| | CDN |
|---|---|
| 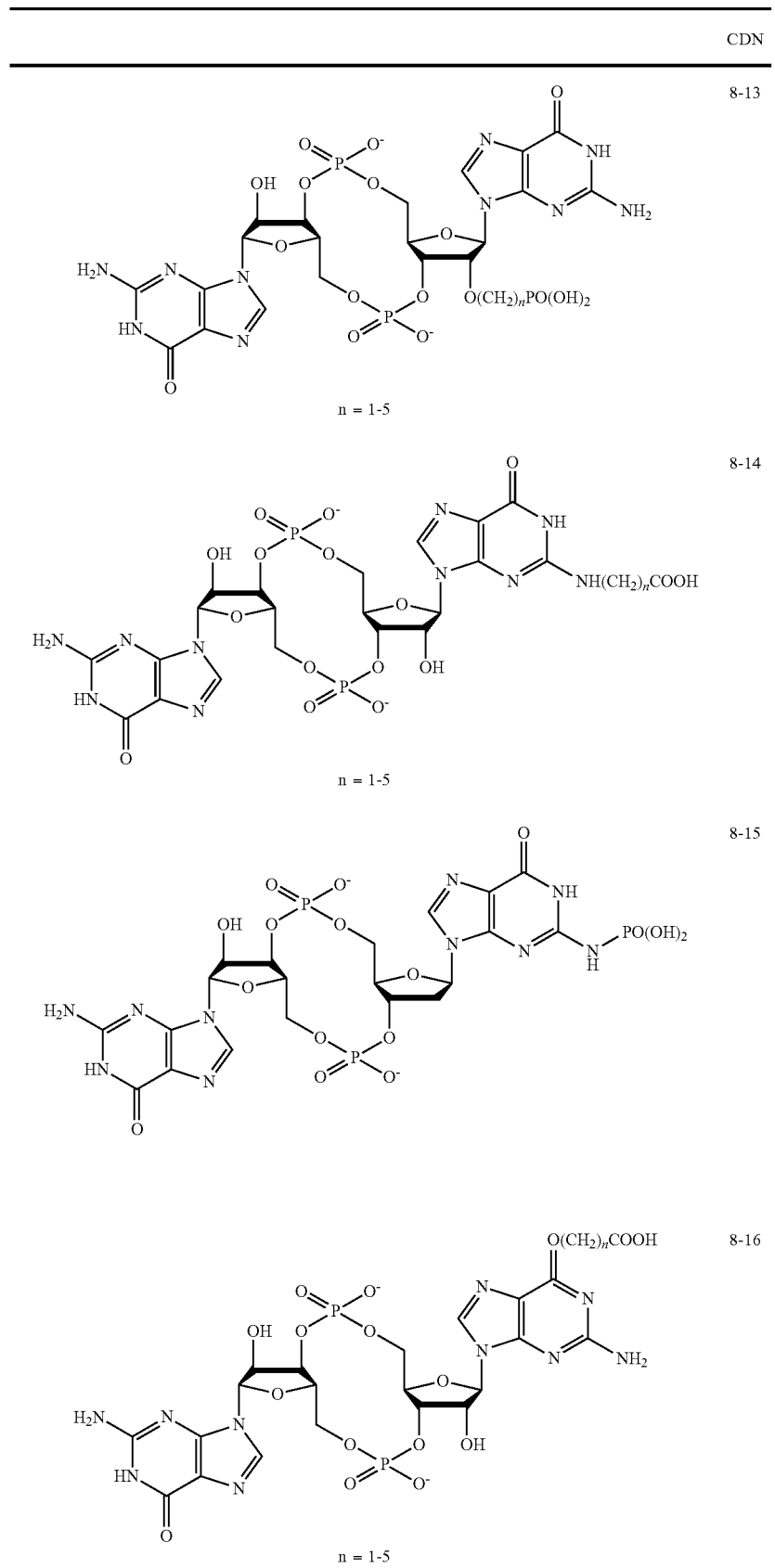 | 8-13 |
| | 8-14 |
| | 8-15 |
| | 8-16 |
n = 1-5
n = 1-5
n = 1-5

TABLE 8-continued

| | CDN |
|---|---|
| 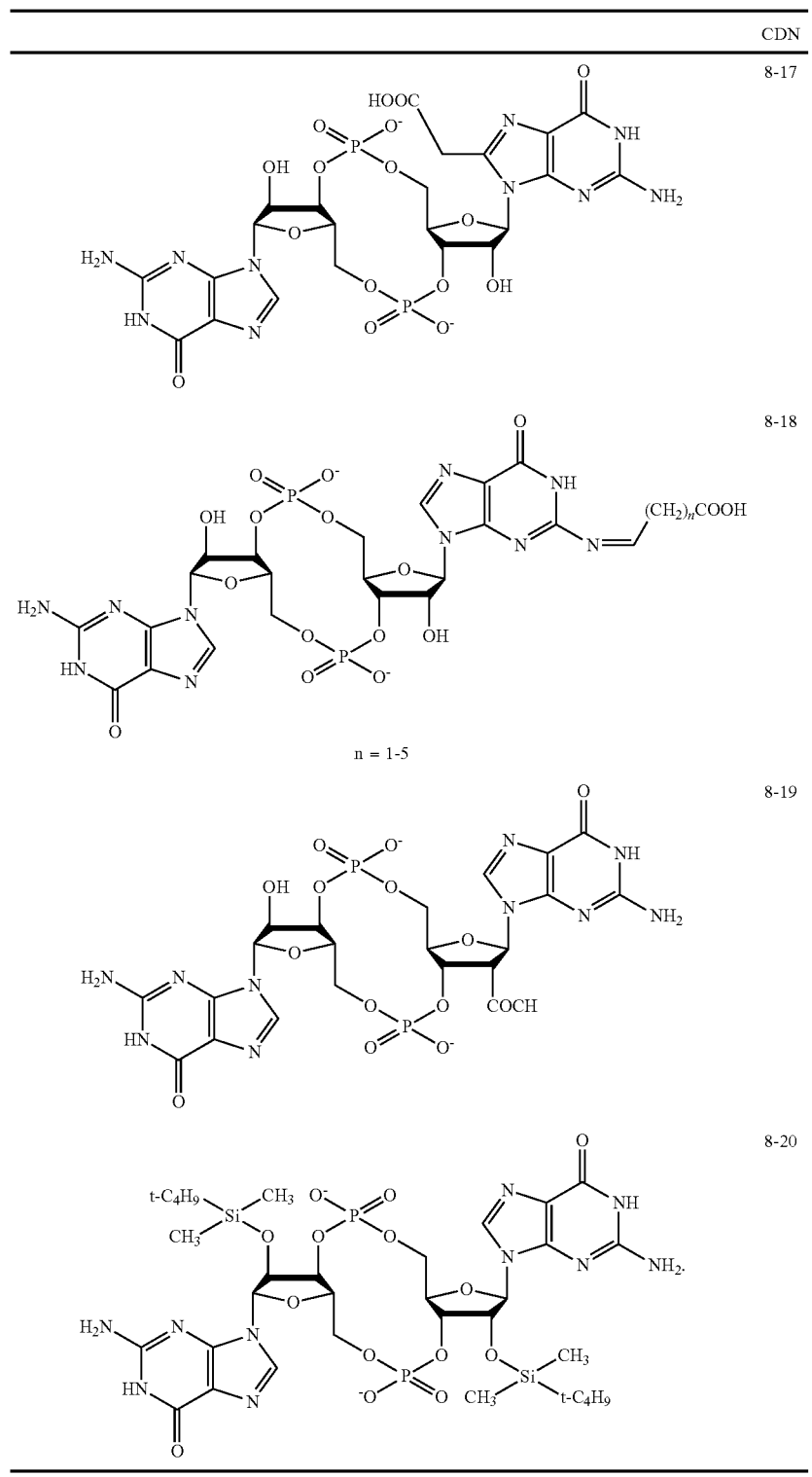 | 8-17 |
| | 8-18 |
| n = 1-5 | |
| | 8-19 |
| | 8-20 |

6.1.9. Additional Cargo Moieties

The complexes of the disclosure can include one or more cargo moieties in addition to the one or more CDN binding moieties. For example, a complex can include one or more CDN binding moieties and one, two, three, or more than three additional cargo moieties per complex.

Additional cargo moieties can be, for example, a molecule or molecular assembly that is biologically active or has diagnostic utility (e.g., as described in Sections 6.1.9.1 to 6.1.9.9).

The additional cargo moiety can be an amphipathic molecule, for example, a ganglioside. Where the additional cargo moiety is amphipathic, the complex need not include other amphipathic molecules, for example to solubilize the lipid binding peptides, although complexes that include amphipathic cargo moieties and additional amphipathic molecules are within the scope of the present disclosure.

The additional cargo moiety need not be amphipathic. In such instances, the additional cargo moiety can be non-covalently or covalently attached to another component in the complex. By way of example but not limitation, the additional cargo moiety can be (a) non-covalently bound to an apolar region of the complex (e.g., an apolar core of a complex formed by apolar regions of apolipoprotein molecules), (b) coupled to the complex by being grafted to an amphipathic or apolar anchor that can non-covalently bind to an apolar region of the complex (directly or via a linker) or (c) covalently coupled to an apolipoprotein molecule, for example, via a direct bond or via a linker.

The additional cargo moiety can be charged or uncharged. Charged cargo moieties can contribute a net charge (either positive or negative) of 1, 2, 3, or more than 3 per lipid binding protein molecule in the complex. In some embodiments the additional cargo moiety contributes a net charge of 1 (positive or negative) per lipid binding protein molecule in the complex. In some embodiments the cargo moiety contributes a net charge of 2 (positive or negative) per lipid binding protein molecule in the complex. In some embodiments, the additional cargo moiety contributes a net charge of 3 (positive or negative) per lipid binding protein molecule in the complex. In some embodiments, the additional cargo moiety contributes a net charge of more than 3 (positive or negative) per lipid binding protein molecule in the complex. In other embodiments, charged cargo moieties can contribute a net charge (either positive or negative) of 1, 2, 3, or more than 3 to the complex. In some embodiments, the additional cargo moiety contributes a net charge of 1 (positive or negative) to the complex. In some embodiments, the additional cargo moiety contributes a net charge of 2 (positive or negative) to the complex. In some embodiments, the additional cargo moiety contributes a net charge of 3 (positive or negative) to the complex. In some embodiments, the additional cargo moiety contributes a net charge of more than 3 (positive or negative) to the complex.

Suitable cargo moieties include therapeutic agents, diagnostic agents and immunogens (e.g., any of the therapeutic agents, diagnostic agents, and immunogens described in WO 2016/154544, incorporated herein by reference in its entirety). Exemplary types of cargo moieties include nucleic acids, peptides, and lipids (e.g., glycolipids).

Diagnostic agents that can be included are labeled agents such as gold labeled agents, labeled agent with stable isotopes, labeled agents with radioactive isotopes and labeled agent with fluorescent probes. Therapeutic agents that can be included in the complex include immunoinhibitory agents, immunostimulatory agents, anti-cancer agents, anti-infective agents, nucleic acid drugs, anti-inflammatory agents, agents for treating cardiovascular disorders, caspase inhibitors and bioactive molecules. Unless required otherwise by context, identification of a specific agent encompasses salts thereof. Thus, for example, recitation of "warfarin" encompasses "warfarin sodium," recitation of "clopidogrel" encompasses "clopidogrel bisulfate," etc.

Complexes of the disclosure can further comprise a cargo moiety which targets the complex to a desired body region (e.g., a target organ). Such cargo moieties can assist in delivery of the complexes to desired body regions (e.g., bodily regions affected by a cancer). Examples of targeting agents which can be included in a complex include an antibody or antibody fragment (e.g. an antibody composed of two heavy chains and two light chains, an Fab fragment, a heavy chain antibody, or a single domain antibody), receptor ligand, hormone, vitamin, and antigen. In some embodiments, the antibody or antibody fragment is specific for a disease-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid. In some embodiments, an apolipoprotein moiety is the ligand to a receptor.

6.1.9.1. Immunoinhibitory and Immunostimulatory Agents

Complexes of the disclosure can include one or more immunoinhibitory agents as cargo moieties in addition to the CDN cargo moieties. Immunoinhibitory agents that can be included in the complexes include steroids, retinoic acid, dexamethasone, cyclophosphamide, and combinations thereof.

A complex of the disclosure can include one or more immunostimulatory agents. Immunostimulatory agents that can be included in the complexes include immunostimmulatory glycolipids such as alpha-galactosylceramide (aGC) and CpG oligonucleotides (ODNs). Complexes comprising immunostimulatory glycolipids such as aCG can be used to induce a Natural Killer T cell-mediated immune response in a cell (e.g., in vitro or in vivo). CpG ODNs are species-specific synthetic single stranded DNA incorporating unmethylated CpG dinucleotides. The optimal motif CpG motif in humans is GTCGTT and GACGTT in mouse. CpG ODNs mimic the immune stimulatory effects of unmethylated bacterial or viral sequences and activate pattern recognition transmembrane receptors, promote cytokine secretion and mount rapid responses to microbial pathogens. CpG ODNs mimic the natural Toll-like receptor (TLR) 9 ligand for the production of signaling factors and trigger a cascade of immune responses against cancer cells. These molecules can have a partially or completely phosphorothioated (PS) backbone as opposed to the phosphodiester (PO) backbone found in genomic bacterial DNA. There are three major classes (A, B, C) of stimulatory CpG ODNs based on structural characteristics and activity on human peripheral blood mononuclear cells (PBMCs) such as B cells and plasmacytoid dendritic cells (pDCs).

Class A CpG ODNs contain a central palindromic CpG-containing phosphodiester (PO) sequence and a PS-modified 3' poly-G string. The poly G tails form intermolecular tetrads to enhance stability and increase endosomal uptake which can then promote the maturation of pDCs and therefore production of large amounts of IFN-$\alpha$. This class strongly activate Natural Killer (NK) cells through indirect cytokine signaling while weakly stimulating NF-$\kappa$B signaling and pro-inflammatory cytokine (e.g. IL-6) production. Class B molecules are structurally linear and contain a fully PS backbone with one or more 6mer CpG motifs. CpG-B ODNs strongly stimulate B cell proliferation and activation along with NK cell activation through NF-$\kappa$B signaling to display anti-tumor activity. These molecules are potent Type 1 T-helper cell (Th1) vaccine adjuvants, but are weak activators of IFN-$\alpha$ secretion. CpG-C ODNs are an amalgam of classes A and B with a complete PS backbone and a palindromic CpG-containing motif. These molecules are strong stimulators of B cells, type I IFN secretion and Th1-inducing adjuvants. All the CpG ODNs contain one or more unmethylated CpG dinucleotides in specific sequence contexts, which are readily recognized by mammalian cells as an indication of microbial invasion, due to the rarity of this structure in mammalian genomes.

In some embodiments, a complex of the disclosure comprises a CpG oligonucleotide which is a class A CpG oligonucleotide, for example, a CpG oligonucleotide having a nucleotide sequence comprising or consisting of the nucleotide sequence of SEQ ID NO:19 or SEQ ID NO:20. In some embodiments, the complex comprises a CpG oligonucleotide which is a class B CpG oligonucleotide, for example, a CpG oligonucleotide having a nucleotide sequence comprising or consisting of the nucleotide sequence of SEQ ID NO:21, SEQ ID NO:22 or SEQ ID NO:23. In yet other embodiments, the complex comprises a CpG oligonucleotide which is a class C CpG oligonucleotide, for example, a CpG oligonucleotide having a nucleotide sequence comprising or consisting of the nucleotide sequence of SEQ ID NO: 24, SEQ ID NO:25, or SEQ ID NO:26.

A lipid moiety (e.g., having characteristics like that of cholesterol or other sterols) can be conjugated to a terminus of a CpG ODN to be used as an anchor to couple the CpG ODN to the complex. A cholesterol tag can be added at the 3' or 5' of an ODN using a C4- to C8-linker or a polyethylene glycol linker to improve transduction of the molecule and improve nuclease resistance with greater target anti-viral activity. Another method of conjugating a CpG ODN to a lipid consists of conjugation of ODNs with alkyl chains (greater than 12 carbons), fatty acids, or lipid substituted crown ethers. Lipophilic dendrimers can be conjugated to either the 5' or 3' ends of ODNs to increase their cellular uptake, but increasing the size of the dendrimer can be a detriment to binding activity for their target inside the cell. Phosphatidyl groups are amenable to conjugation to ODNs and provide a high similarity in molecular structure to many lipid constituents of cell membranes. 1,2-Ditetra, 1,2-dihexa- and 1,2-dioctadecanoylglycerol having the S' configuration at the stereogenic carbon can be used. The resulting phosphoramidites have the same stereochemistry at the chiral center as in naturally occurring phospholipids (R) to allow passage into cells. In addition, 5'—O-phosphatidyloligodeoxynucleotides with varying phosphatidyl tails and/or the sequence and length of the ODN moiety can be used.

6.1.9.2. Anti-Cancer Agents

Complexes of the disclosure can include one or more anti-cancer agents as cargo moieties in addition to the CDN cargo moieties. Anti-cancer agents that can be included in the complexes include topoisomerase inhibitors, DNA alkylating agents, DNA strand break inducing agents, anti-microtubule agents, an anti-metabolic agents, anthracyclines, vinca alkaloids, epipodophyllotoxins, tyrosine kinase inhibitors, CDK inhibitors, MAP kinase inhibitors, EGFR inhibitors, and VEGFR inhibitors.

In certain aspects, the anti-cancer agent is a chemotherapeutic agent, e.g., a cytotoxic or cytostatic agent. Examples of chemotherapeutic agents include alkylating agents such as thiotepa and CYTOXAN® cyclosphosphamide; alkyl sulfonates such as busulfan, improsulfan, piposulfan and treosulfan; decarbazine; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e.g., calicheamicin, especially calicheamicin gamma11 and calicheamicin omega11 (see, e.g., Agnew, Chem. Intl. Ed. Engl. 33:183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins (e.g., bleomycin A2, bleomycin B2 and peplomycin), cactinomycin, carabicin, carminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, tiazofurin, ribavarin, EICAR, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate and trimetrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEXRM, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; deferoxamine; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; cytosine arabinoside ("Ara-C"); cyclophosphamide; thiotepa; taxoids and taxanes, e.g., TAXOL.® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); epipodophyllins such as etoposide (VP-16), teniposide, tepotecan, 9-aminocamptothecin, camptothecin and crisnatol; ifosfamide; mitoxantrone; *vinca* alkaloids such as vincristine (ONCOVIN®), vindesine, *vinca* alkaloid, and vinorelbine (NAVELBINE®); novantrone; edatrexate; daunomycin; aminopterin; xeloda; ibandronate; topoisomerase inhibitor RFS 2000; difluorometlhylornithine (DMFO); retinoids such as retinoic acid; pharmaceutically acceptable salts, acids or derivatives of any of the above.

In some embodiments, the anti-cancer agent is methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, or docetaxel.

In some embodiments, the anti-cancer agent is an antibody. In certain embodiments, the anti-cancer antibody is an anti-CD20 antibody, e.g., rituximab or tositumomab (which are useful for treating, inter alia, B-cell non-Hodgkin's lymphoma), an anti-CD52 antibody, e.g., alemtuzumab (which is useful for treating B-cell chronic lymphocytic leukemia), an-anti EGF receptor antibody, e.g., cetuximab or panitumumab (which are useful for treating head and neck cancer and colorectal cancer), an anti-VEGF antibody, e.g., bevacizumab (which is useful for treating, inter alia, colorectal cancer), or an anti-HER2 antibody, e.g., trastuzumab (which is useful for treating HER2-positive metastatic breast cancer).

In some embodiments, the anti-cancer agent is in the form of an antibody-drug conjugate (ADC). Exemplary ADCs include gemtuzumab ozogamicin (approved to treat acute myeloid leukemia), brentuximab vedotin (approved to treat Hodgkin lymphoma), trastuzumab emtansine (approved to treat HER2-positive metastatic breast cancer), and Inotuzumab ozogamicin (approved to treat acute lymphoblastic leukemia).

Exemplary topoisomerase inhibitors include type I inhibitors such as irinotecan, topotecan, camptothecin and lamellarin D and type II inhibitor such as etoposide, teniposide, doxorubicin, daunorubicin, mitoxantrone, amsacrine, ellipticines, aurintricarboxylic acid, and HU-331. Exemplary DNA alkylating agents include classical DNA alkylating agents such as nitrogen mustards (e.g., cyclophosphamide, mechlorethamine, uramustine, melphalan, chlorambucil, ifosfamide, and bendamustine) nitrosoureas (e.g., carmustine, lomustine, and streptozocin) and alkyl sulfonates (e.g., busulfan), alkylating-like agents such as cisplatin, carboplatin, nedaplatin, oxaliplatin, satraplatin, and triplatin tetranitrate, and non-classical alkylating agents such as procarbazine and altretamine. Exemplary DNA strand break inducing agents include calicheamicin, etoposide, doxorubicin, ginsenoside Rg3, Bleomycin A5, Raltitrexed, and SCH-900776. Exemplary anti-microtubule agents include paclitaxel, docetaxel, and cabazitaxel. Exemplary anti-metabolic agents include 5-fluorouracil (5-FU), 6-mercaptopurine (6-MP), capecitabine, cytarabine, floxuridine, fludarabine, gemcitabine, hydroxycarbamide, methotrexate, and pemetrexed. Exemplary anthracyclines include daunorubicin and doxorubicin. Exemplary *vinca* alkaloids include vinblastine, vincristine, vindesine, vinorelbine, vincaminol, vineridine, and vinburnine. Exemplary epipodophyllotoxins include etoposide and teniposide. Exemplary tyrosine kinase inhibitors include imatinib, gefitinib, and erlotinib. Exemplary CDK inhibitors include palbociclib, abemaciclib, and ribociclib. Exemplary EGFR inhibitors include gefitinib, erlotinib, afatinib, brigatinib, icotinib, and cetuximab. Exemplary VEGFR inhibitors include pazopanib, vatalanib, sunitinib, and sorafenib.

In certain embodiments, a complex of the disclosure comprises an anti-cancer agent that is useful in the treatment of melanoma. It has been demonstrated that melanomas that express high levels of SR-B1 are associated with poorer outcomes than melanomas that express low levels of SR-B1 (Mikula et al., 2017, Mol. Cancer Res., doi: 10.1158/1541-7786). Without being bound by theory, it is expected that complexes carrying anti-melanoma agents are able to target melanoma cells that are more resistant to therapy. Accordingly, in certain aspects, the disclosure provides complexes comprising an anti-melanoma agent, such as, but not limited to, aldesleukin, cobimetinib, dabrafenib, dacarbazine, talimogene laherparepvec, ipilimumab, pembrolizumab, trametinib, nivolumab, or orvemurafenib). Such complexes can be administered to subjects with melanoma as monotherapy or as part of combination therapy regimens, for example with chemotherapeutic agents or interferon-based therapies (e.g., recombinant interferon alfa-2b, peginterferon alfa-2a, or peginterferon alfa-2b).

6.1.9.3. Anti-infective agents

Complexes of the disclosure can include one or more anti-infective agents as cargo moieties in addition to the CDN cargo moieties. Anti-infective agents that can be included in the complexes of the disclosure include anti-bacterial agents, anti-viral agents, anti-parasitic agents, anti-fungal agents, and anti-mycobacterial agents.

Exemplary anti-bacterial agents include β-lactam antibiotics, penicillins (e.g., penicillin, methicillin, ampicillin, amoxicillin), cephalosporins (e.g., avibactam, cephalexin, cefepime, ceftaroline), β-lactamase inhibitors (e.g., tebipenem, clavulanate, sulbactam and tazobactam), vancomycin, aminoglycosides (e.g., gentamycin, neomycin B, neomycin C, neomycin E, streptomycin), tetracyclines (e.g., tetracycline, lymecycline, methacycline, and doxycycline), chloramphenicol, erythromycin, lincomycin, clindamycin, rifampin, metronidazole, polymyxins (e.g., polymyxin B and polymyxin E), sulfonamides (e.g., sulfisoxazole and sulfaisodimidine), and quinolones (e.g., cinoxacin, ciprofloxacin, balofloxacin, and gatifloxacin).

Exemplary anti-viral agents include amantadine, rimantadine, ribivarin, acyclovir, vidarabine, trifluorothymidine, ganciclovir, zidovudine, retinovir, and interferons.

Exemplary anti-fungal agents include imidazoles (e.g., bifonazole, sertaconazole), triazoles (e.g., albaconazole, isavuconazole), polyene macrolide antibiotics (e.g., amphotericin B, nystatin, and natamycin), griseofulvin, amphotericin B, and flucytosine.

Anti-parasitic agents include anthelmintics and antiprotozoal agents.

6.1.9.4. Nucleic acid drugs

Complexes of the disclosure can include one or more nucleic acid drugs as cargo moieties in addition to the CDN cargo moieties. Nucleic acid drugs that can be included in the complex of the disclosure include naturally or non-naturally occurring DNA, a naturally or non-naturally occurring RNA, an oligonucleotide, a triple-helix forming molecule, an immunostimulatory nucleic acid, a small interfering RNA (siRNA), a microRNAs (miRNA), an antisense oligonucleotide, an aptamer, a ribozyme, a gene or gene fragment, a regulatory sequence. The nucleic acid can be complexed to a moiety to facilitate binding to or uptake by a target cell. The nucleic acid can be covalently bound to a molecule interacting with the complex. For example, a nucleic acid can be covalently linked to a sterol, a fatty acid or a phospholipid such as those described in Section 6.1.4.1.

In some embodiments, the nucleic acid drug is a siRNA or antisense oligonucleotide. The antisense oligonucleotide can be, for example, a double-stranded oligonucleotide (e.g., as described in US 2017/0137816). Such embodiments are not limited to a particular size or type of molecule. The length of the region of the siRNA or antisense oligonucleotide complementary to the target, for example, can be from 15 to 100 nucleotides, 18 to 25 nucleotides, 20 to 23 nucleotides, or more than 15, 16, 17 or 18 nucleotides. Where there are mismatches to the corresponding target region, the length of the complementary region is generally required to be somewhat longer.

In certain embodiments, it is contemplated that delivering siRNA or antisense oligonucleotides using complexes as described herein can be used to inhibit any gene of interest (e.g., in a target cell in vitro or in vivo).

Loading of a nucleic acid drug into a complex of the disclosure can be facilitated through cholesterol modification of the nucleic acid drug. For example, the siRNA can be modified with cholesterol at the 3' sense strand and an intermediate level of chemical modification can be used to stabilize siRNA in the serum without significantly compromising its silencing effect.

Nucleic acid drugs can be labeled with an imaging agent (e.g., fluorescent dye Cy3) to permit visualization of the biodistribution of the nucleic acid drug at the organ level and also the intracellular delivery profile. In some embodiments, RT-PCR and western blot are used to analyze the target protein at the mRNA level and protein level, respectively.

In some embodiments, the complexes of the disclosure comprise one or more siRNAs specific for proprotein convertase subtilisin/kexin 9 (PCSK9). In some embodiments, the PCSK9 siRNA sequence is cross-reactive to murine, rat, nonhuman primate and human PCSK9 mRNA (see, e.g., Frank-Kamenetsky, et al., 2008, Proceedings of the National Academy of Sciences of the United States of America 105 (33): 11915-11920).

In some embodiments, the complexes of the disclosure comprise one or more siRNAs specific for the gene coding for apolipoprotein B, the apolipoprotein of LDL lipoproteins.

In some embodiments, the complexes of the disclosure comprise one or more targeted gene silencing molecules (e.g., siRNAs) to block production of the dysfunctional huntingtin (Htt) protein, the cause of Huntington's disease, a fatal, inherited neurodegenerative disorder (see, e.g., www.scbt.com/scbt/product/huntingtin-sirna-h-shrna-and-lentiviral-particle-gene-silencers).

In some embodiments, the complexes of the disclosure comprise one or more targeted gene silencing molecules (e.g., siRNAs) to block production of the amyloid precursor protein (APP) products, which cause Alzheimer's disease.

In some embodiments, the complexes of the disclosure comprise one or more targeted gene silencing molecules, such as those described in WO 2014076195 A1, to block production of proteins involved in pathologic processes.

In some embodiments, the complexes of the disclosure comprise one or more targeted gene silencing molecules (e.g., antisense oligonucleotides or siRNAs) to block production of STAT3, which can be used, for example, for treating pancreatic cancer.

In some embodiments, the complexes of the disclosure comprise one or more targeted gene silencing molecules (e.g., antisense oligonucleotides or siRNAs) to block production of KRAS, which can be used, for example, for treating pancreatic cancer.

In some embodiments, the complexes of the disclosure comprise one or more targeted gene silencing molecules (e.g., antisense oligonucleotides or siRNAs) to block production of EGFR, which can be used, for example, for treating pancreatic cancer.

6.1.9.5. Anti-Inflammatory Agents

Complexes of the disclosure can include one or more anti-inflammatory agents as cargo moieties in addition to the CDN cargo moieties. Anti-inflammatory agents that can be included in the complexes of the disclosure include one or more of Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Aspirin; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Gemcabene, Bempedoic acid and Zomepirac Sodium.

6.1.9.6. Caspase Inhibitors

Complexes of the disclosure can include one or more caspase inhibitors (e.g., a caspase-1 inhibitor, a caspase-3 inhibitor, or a caspase-8 inhibitor) as cargo moieties in addition to the CDN cargo moieties. Caspase inhibitors may be useful for treating non-alcoholic fatty liver disease, epilepsy, ischemic disorders, Huntington's disease, amyotrophic lateral sclerosis (ALS), autoimmune diseases such as rheumatoid arthritis, osteoarthritis, inflammatory bowel disease, viral infections (e.g., hepatitis C) and sepsis. Exemplary caspase inhibitors that have been studied clinically and which can be included in complexes of the disclosure include emricasan, pralnacasan, and VX-765. Other caspase inhibitors that can be included in complexes of the disclosure are described in US 2010/0041661, WO/2001/021600, and U.S. Pat. No. 9,365,612.

6.1.9.7. Bioactive Agents

The complexes of the disclosure can include one or more bioactive agents or one or more deuterated bioactive agents as cargo moieties in addition to the CDN cargo moieties. Highly deuterated bioactive agents can be useful for inhibiting biological processes. Exemplary bioactive agents include polyphenols, such as flavonoids (e.g., anthoxanthins such as luteolin, apigenin, tangeritin, quercetin, kaempferol, myricetin, fisetin, galangin, isorhamnetin, pachypodol, rhamnazin, pyranoflavonols, and furanoflavonols; flavanones such as hesperetin, naringenin, eriodictyol, and homoeriodictyol; flavanonols such as dihydroquercetin and dihydrokaempferol, flavans such as catechin, gallocatechin, catechin 3-gallate, gallocatechin 3-gallate, epicatechins, epigallocatechin, epicatechin 3-gallate, epigallocatechin 3-gallate, theaflavin, and leucoanthocyanidin), carotenoids (e.g., beta-carotene, alpha-carotene, beta-cryptoxanthin and gamma-carotene, lutein, lycopene, astaxanthin, zeaxanthin) and phytosterols.

6.1.9.8. Diagnostic Agents

The complexes of the disclosure can include one or more imaging agents such as a fluorescent moiety, a phosphorescent moiety, gold, a radioactive moiety, a beta emitter, or a combination thereof as cargo moieties in addition to the CDN cargo moieties. Suitable imaging agents include, but are not limited to, fluorescent molecules such as those described by Molecular Probes (Handbook of fluorescent probes and research products), such as Rhodamine, fluorescein, Texas red, Acridine Orange, Alexa Fluor (various), Allophycocyanin, 7-aminoactinomycin D, BOBO-1, BODIPY (various), Calcien, Calcium Crimson, Calcium green, Calcium Orange, 6-carboxyrhodamine 6G, Cascade blue, Cascade yellow, DAPI, DIA, DID, Di1, DIO, DIR, ELF 97, Eosin, ER Tracker Blue-White, EthD-1, Ethidium bromide, Fluo-3, Fluo4, FM1-43, FM4-64, Fura-2, Fura Red, Hoechst 33258, Hoechst 33342, 7-hydroxy-4-methylcoumarin, Indo-1, JC-1, JC-9, JOE dye, Lissamine rhodamine B, Lucifer Yellow CH, LysoSensor Blue DND-167, LysoSensor Green, LysoSensor Yellow/Blu, Lysotracker Green FM, Magnesium Green, Marina Blue, Mitotracker Green FM, Mitotracker Orange CMTMRos, MitoTracker Red CMXRos, Monobromobimane, NBD amines, NeruoTrace 500/525 green, Nile red, Oregon Green, Pacific Blue. POP-1, Propidium iodide, Rhodamine 110, Rhodamine Red, R-Phycoerythrin, Resorfin, RH414, Rhod-2, Rhodamine Green, Rhodamine 123, ROX dye, Sodium Green, SYTO blue (various), SYTO green (Various), SYTO orange (various), SYTOX blue, SYTOX green, SYTOX orange, Tetramethylrhodamine B, TOT-1, TOT-3, X-rhod-1, YOYO-1, YOYO-3. In some embodiments, ceramides are provided as imaging agents. In some embodiments, S1P agonists are provided as imaging agents. Additionally, radionuclides can be used as imaging agents and included in complexes of the disclosure (e.g., by being bound by a chelator that is directly or indirectly bound to a component of a complex, for example as described in Zheng et al., 2016, Atherosclerosis 251:381-388)). Suitable radionuclides include, but are not limited to radioactive species of Fe (III), Fe (II), Cu (II), Mg (II), Ca (II), and Zn (11) Indium, Gallium and Technetium. Other suitable contrast agents include metal ions generally used for chelation in paramagnetic T1-type MIR contrast agents, and include di- and tri-valent cations such as copper, chromium, iron, gadolinium, manganese, erbium, europium, dysprosium and holmium. Metal ions that can be chelated and used for radionuclide imaging, include, but are not limited to metals such as gallium, germanium, cobalt, calcium, indium, iridium, rubidium, yttrium, ruthenium, yttrium, technetium, rhenium, platinum, thallium, samarium, and zirconium (e.g., $^{89}$Zr). Additional metal ions known to be useful in neutron-capture radiation therapy include boron and other metals with large nuclear cross-sections. Also suitable are metal ions useful in ultrasound contrast, and X-ray contrast compositions. Examples of other suitable contrast agents include gases or gas emitting compounds, which are radioopaque.

6.1.9.9. Immunogens

The complexes of the disclosure can include one or more immunogens such as antigens or antigen-encoding nucleic acids as cargo moieties in addition to the CDN cargo moieties. Suitable antigens can include an antigen associated with an allergic reaction, for example, a pollen, a venom, animal dander, a fungal spore, a drug allergen or a food allergen. Other suitable antigens can be autoantigens, for example, a lupus antigen, a multiple sclerosis antigen, a rheumatoid arthritis antigen, a diabetes mellitus type I antigen, an inflammatory bowel disease antigen, a thyroiditis antigen, or a celiac disease antigen.

The antigen can be, for example, a peptide based antigen, a protein based antigen, a polysaccharide based antigen, a saccharide based antigen, a lipid based antigen, a glycolipid based antigen, a nucleic acid based antigen, an inactivated organism based antigen, an attenuated organism based antigen, a viral antigen, a bacterial antigen, a parasite antigen, an antigen derived from an allergen, or a tumor antigen.

A peptide based antigen can be, for example, a retro-inverso peptide (e.g., as described in van Regenmortel et al., 1998, Dev Biol Stand. 92:139-43).

In some embodiments, the antigen is a self antigen, which is an immunogenic antigen or epitope native to a mammal and which may be involved in the pathogenesis of an autoimmune disease.

In some embodiments, the antigen is a viral antigen. Viral antigens can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

In some embodiments, the antigen is a bacterial antigen. Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.*

In some embodiments, the antigen is a parasite antigen. Parasite antigens can be obtained from parasites such *Cryptococcus neoformans, Histoplasma capsulatum, Candida albicans, Candida tropicalis, Nocardia asteroides, Rickettsia rickettsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

In some embodiments, the antigen is an allergen and environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.e. grasses of the genera *Lolium, Phleum, Poa, Cynodon, Dactylis, Holcus, Phalaris, Secale*, and *Sorghum*, the orders of Asterales and Urticales including i.a. herbs of the genera *Ambrosia, Artemisia*, and *Parietaria*. Other allergen antigens that may be used include allergens from house dust mites of the genus *Dermatophagoides* and *Euroglyphus*, storage mite e.g *Lepidoglyphys, Glycyphagus* and *Tyrophagus*, those from cockroaches, midges and fleas e.g. *Blatella, Periplaneta, Chironomus* and *Ctenocepphalides*, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

In some embodiments, the antigen is a tumor antigen. The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARa fusion protein, PTPRK, K-ras, N-ras, Triose-phosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15 (58), CEA, RAGE, NY-ESO (LAGS), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS.

In some embodiments, the antigen is against PCSK9.

In some embodiments, the antigen is against gp100 melanoma.

In some embodiments, the antigen is a neo-antigen. The term neo-antigen is used herein to define any newly expressed antigenic determinant. Neo-antigens may arise upon conformational change in a protein, as newly expressed determinants (especially on the surfaces of transformed or infected cells), as the result of complex formation of one or more molecules or as the result of cleavage of a molecule with a resultant display of new antigenic determinants. Thus, as used herein, the term neo-antigen covers antigens expressed upon infection (e.g. viral infection, protozoal infection or bacterial infection), in prion-mediated diseases, and on cell transformation (cancer), in which latter case the neo-antigen may be termed a tumor-associated antigen.

Identification of neo-antigens can involve identifying all, or nearly all, mutations in the neoplasia/tumor at the DNA level using whole genome sequencing, whole exome (e.g., only captured exons) sequencing, or RNA sequencing of tumor versus matched germline samples from each patient. In some embodiments, identification of neo-antigens involves analyzing the identified mutations with one or more peptide-MHC binding prediction algorithms to generate a plurality of candidate neo-antigen T cell epitopes that are expressed within the neoplasia/tumor and may bind patient HLA alleles. In some embodiments, identification of neo-antigens involves synthesizing the plurality of candidate neo-antigen peptides selected from the sets of all neo open reading frame peptides and predicted binding peptides for use in a cancer vaccine.

In certain embodiments the size of the at least one neo-antigenic peptide molecule can be, for example, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, about 120 or greater amino molecule residues, and any range derivable therein. In specific embodiments the neo-antigenic peptide molecules are equal to or less than 50 amino acids. In a preferred embodiment, the neo-antigenic peptide molecules are equal to about 20 to about 30 amino acids.

Complexes of the disclosure can include one or more neo-antigenic peptides. In some embodiments, a complex of the disclosure comprises one neo-antigenic peptide. In some embodiments, a complex comprises two neo-antigenic peptides. In some embodiments, a complex comprises at least 5 or more neo-antigenic peptides. In some embodiments, a complex comprises at least about 6, about 8, about 10, about 12, about 14, about 16, about 18, or about 20 distinct peptides. In some embodiments, a complex comprises at least 20 distinct peptides.

Neo-antigenic peptides, polypeptides, and analogs can be further modified to contain additional chemical moieties not normally part of the protein. Those derivatized moieties can improve the solubility, the biological half-life, absorption of the protein, or binding affinity. The moieties can also reduce or eliminate any desirable side effects of the proteins and the like. An overview for those moieties can be found in Allen et al., eds., 2012, Remington: The Science and Practice of Pharmacy, $22^{nd}$ Edition, Pharmaceutical Press, London, UK. For example, neo-antigenic peptides and polypeptides having the desired activity may be modified as necessary to provide certain desired attributes, e.g. improved pharmacological characteristics, while increasing or at least retaining substantially all of the biological activity of the unmodified peptide to bind the desired MHC molecule and activate the appropriate T cell. For instance, the neo-antigenic peptide and polypeptides may be subject to various changes, such as substitutions, either conservative or non-conservative, where such changes might provide for certain advantages in their use, such as improved MHC binding. Such conservative substitutions may encompass replacing an amino acid residue with another amino acid residue that is biologically and/or chemically similar, e.g., one hydrophobic residue for another, or one polar residue for another. The effect of single amino acid substitutions may also be probed using D-amino acids. Such modifications may be made using well known peptide synthesis procedures.

In some embodiments, the neo-antigenic peptides and polypeptides may be modified with linking agents for purposes of facilitating complexing with the complexes of the disclosure. The disclosure is not limited to a particular type or kind of linking agent. In some embodiments, the linking agent is a cysteine-serine-serine (CSS) molecule.

In some embodiments wherein the neo-antigenic peptide or polypeptide is modified with CSS, the complex is further modified with dioleoyl-sn-glycero-3-phosphoethanolamine-N-[3-(2-pyridyldithio) propionate] (DOPE-PDP) wherein upon mixing, the DOPE-PDP and CSS engage thereby resulting in a complexing (linking) of the CSS-Ag with the complex.

The neo-antigenic peptide and polypeptides may also be modified by extending or decreasing the compound's amino acid sequence, e.g., by the addition or deletion of amino acids. The neo-antigenic peptides, polypeptides, or analogs can also be modified by altering the order or composition of certain residues. It will be appreciated by the skilled artisan that certain amino acid residues essential for biological activity, e.g., those at critical contact sites or conserved residues, may generally not be altered without an adverse effect on biological activity. The non-critical amino acids need not be limited to those naturally occurring in proteins, such as L-a-amino acids, or their D-isomers, but may include non-natural amino acids as well, such as β-γ-δ-amino acids, as well as many derivatives of L-a-amino acids.

Typically, a neo-antigen polypeptide or peptide may be optimized by using a series of peptides with single amino acid substitutions to determine the effect of electrostatic charge, hydrophobicity, etc. on MHC binding. For instance, a series of positively charged (e.g., Lys or Arg) or negatively charged (e.g., Glu) amino acid substitutions may be made along the length of the peptide revealing different patterns of sensitivity towards various MHC molecules and T cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding. Amino acid substitutions are typically of single residues. Substitutions, deletions, insertions or any combination thereof may be combined to arrive at a final peptide.

One of skill in the art will appreciate that there are a variety of ways in which to produce such tumor specific neo-antigens. In general, such tumor specific neo-antigens may be produced either in vitro or in vivo. Tumor specific neo-antigens may be produced in vitro as peptides or polypeptides, which may then be formulated into a personalized neoplasia vaccine and administered to a subject. Such in vitro production may occur by a variety of methods known to one of skill in the art such as, for example, peptide synthesis or expression of a peptide/polypeptide from a DNA or RNA molecule in any of a variety of bacterial, eukaryotic, or viral recombinant expression systems, followed by purification of the expressed peptide/polypeptide.

Alternatively, tumor specific neo-antigens may be produced in vivo by introducing molecules (e.g., DNA, RNA, viral expression systems, and the like) that encode tumor specific neo-antigens into a subject, whereupon the encoded tumor specific neo-antigens are expressed.

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

Antigens can be provided in a complex of the disclosure as single antigens or can be provided in combination in a single complex. Antigens can also be provided as complex mixtures of polypeptides or nucleic acids.

6.2. Compositions Comprising Complexes of the Disclosure

The disclosure provides compositions comprising complexes of the disclosure. Compositions of the disclosure include compositions comprising complexes having one or more bound CDNs and compositions comprising "empty" complexes that do not have bound CDNs. Compositions comprising empty complexes can be used, for example, in the preparation of pharmaceutical compositions or vaccine compositions having different types of CDNs. Thus, a single composition of empty complexes (e.g., complexes lacking cargo moieties) can be used to make a variety of pharmaceutical compositions, for example to treat different conditions or to make a variety of vaccine compositions.

Pharmaceutical compositions can include one or more than one type of complex of the disclosure (e.g., a complex having a first bound CDN and a second complex having a second bound CDN) and one or more pharmaceutically acceptable carriers, excipients, diluents, or a combination thereof. The complexes of the disclosure can also be included in a vaccine composition comprising complexes and one or more pharmaceutically acceptable carriers, diluents, excipients, adjuvants, or a combination thereof. The complexes of the disclosure can also be included in a diagnostic composition comprising complexes and one or more carriers, diluents, excipients, or a combination thereof which are suitable for diagnostic use.

Exemplary carriers include solvents or dispersion media containing, for example, water, ethanol, a polyol (for example, glycerol, propylene glycol, and liquid polyethylene glycol, and the like), suitable mixtures thereof, and vegetable oils. Exemplary diluents include water for injection, saline solution, buffered solutions such as phosphate buffered saline solution, and sugar solutions such as sucrose or dextran solutions. Exemplary excipients include fillers, binders, disintegrants, solvents, solubilizing agents, and coloring agents.

Exemplary adjuvants include CPG, polyIC, poly-ICLC, 1018 ISS, aluminum salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel.RTM, vector system, PLGA microparticles, imiquimod, resiquimod, gardiquimod, 3M-052, SRL172, Virosomes and other Virus-like particles, YF-17D, VEGF trap, beta-glucan, Pam3Cys, Aquila's QS21 stimulon, vadimezan, and AsA404 (DMXAA).

The compositions of the disclosure can be formulated according to techniques known in the art (e.g., as described in Allen et al., eds., 2012, *Remington: The Science and Practice of Pharmacy*, 22$^{nd}$ Edition, Pharmaceutical Press, London, UK). For example, the compositions can be formulated for subcutaneous, intradermal, intravenous, or intraperitoneal injection (e.g., as a solution), inhalation (intranasal or intrapulmonary inhalation), implantation (e.g., as a suppository), ocular or intraocular administration (e.g., via eye drops).

In some embodiments, the compositions are packaged in unit dosage amounts suitable for administration. For example, in some embodiments, the compositions comprise unit dosage amounts of dried (for example lyophilized) complexes packaged in sealed vials. Such compositions are suitable for reconstitution with water, physiological solution (such as saline) or buffer, and administration via injection. Such compositions may optionally include one or more anti-caking and/or anti-agglomerating agents to facilitate reconstitution of the complex, or one or more buffering agents, isotonicity agents (e.g., sucrose and/or mannitol), sugars or salts (e.g., sodium chloride) designed to adjust the pH, osmolality and/or salinity of the reconstituted suspension. The compositions described above can be manufactured under conditions that minimize oxidation, thereby reducing the risk of side effects, such as liver damage, caused by oxidized products. For example, the compositions can be manufactured under an inert gas, such as nitrogen, helium, or argon.

Complexes of the disclosure may also be formulated in pharmaceutical compositions for controlled release. As used herein, "controlled release" refers to release of a CDN or additional cargo moiety from a formulation at a rate that the blood concentration of the CDN or additional cargo moiety in an individual is maintained within the therapeutic range for an extended duration, over a time period on the order of hours, days, weeks, or longer. Complexes may be formulated in a bioerodible or nonbioerodible controlled matrix, a number of which are well known in the art. A controlled release matrix may include a synthetic polymer or copolymer, for example in the form of a hydrogel. Examples of such polymers include polyesters, polyorthoesters, polyanhydrides, polysaccharides, poly (phosphoesters), polyamides, polyurethanes, poly (imidocarbonates) and poly (phosphazenes), and poly-lactide-co-glycolide (PLGA), a copolymer of poly (lactic acid) and poly (glycolic acid). Collagen, albumin, and fibrinogen containing materials may also be used.

Preferably, the compositions of the disclosure contain only a small amount of uncomplexed amphipathic molecules (when present), lipid binding proteins, CDN binding moieties, and additional cargo moieties (when present). In some embodiments, no more than 20% of the amphipathic molecules in the composition are in uncomplexed form. In other embodiments, no more than 10% of the amphipathic molecules are in uncomplexed form. In yet other embodiments, no more than 5% of the amphipathic molecules are uncomplexed form. In yet other embodiments, no more than 2% of the amphipathic molecules are in uncomplexed form.

The homogeneity of the complexes and compositions of the disclosures can be measured by gel permeation chromatography. A highly homogeneous composition will generally have a main peak corresponding to the complex and, possibly, one or more secondary peaks corresponding to one or more of free protein, free amphipathic molecules, free CDN binding moieties, free CDNs, and free additional cargo moieties (if present in the composition). Secondary peaks corresponding to complexes having a different size from the complexes in the main peak may also be seen. The area of the main peak on a gel permeation chromatogram relative to the total area of the main and secondary peaks determines the percent homogeneity of a composition. In some embodiments, the compositions of the disclosure are at least 75% homogeneous. In other embodiments, the compositions of the disclosure are at least 85% homogeneous. In other embodiments, the compositions of the disclosure are at least 95% homogeneous. In yet other embodiments, the compositions of the disclosure are at least 98% homogeneous.

In some embodiments, the homogeneity of the complexes in the compositions of the disclosure (i.e., the area of the main peak relative to the total area of the main and secondary peaks for complexes having all components) is at least 75%. In other embodiments, the complexes in the compositions of the disclosure are at least 85% homogeneous. In other embodiments, the complexes in the compositions of the disclosure are at least 95% homogeneous. In other embodiments, the complexes in the compositions of the disclosure are at least 98% homogeneous.

In some embodiments of the compositions of the disclosure comprising Cargomers, lipoprotein complexes that (a) have Stokes radii of greater than 2 nm or 3.4 nm (e.g., as determined by gel permeation chromatography) and/or (b) are discoidal and/or (c) have an apolipoprotein: amphipathic molecule molar ratio of 1:8 or greater, if present, preferably represent no more than 10% of the apolipoprotein in the composition on a weight basis. In some embodiments, such complexes represent no more than 5% of the apolipoprotein in the composition on a weight basis. In some embodiments, such complexes represent no more than 2% of the apolipoprotein in the composition on a weight basis. In some embodiments, the compositions are free of detectable lipoprotein complexes that (a) have Stokes radii of greater than 3.4 nm and/or (b) are discoidal and/or (c) have an apolipoprotein: amphipathic molecule molar ratio of 1:8 or greater when the compositions are subjected to gel permeation chromatography under conditions capable of resolving such complexes. Preferably, Cargomer-based compositions of the disclosure are free of lipoprotein complexes having a Stokes radius of greater than 3.25 nm.

The identity and amount of lipoprotein molecules in a composition of the disclosure can be determined, for example, by mass spectrometry (see, e.g., Zhang et al., 2010, Methods Mol Biol. 673:211-222) and in particular FT-MS or by NMR. The identity and amount of amphipathic molecules in a composition of the disclosure can be determined, for example, by thin layer chromatography (see, e.g., Clogston and Patri, 2011, Methods Mol Biol. 697:109-17). The presence of discoidal particles in a composition of the disclosure can be determined, for example, using NMR spectroscopy.

6.3. Processes for Producing Complexes for Carrying CDNs

The disclosure provides methods of producing the complexes of the disclosure.

In one aspect, a method of producing a complex of the disclosure comprises combining (i) a CDN-free complex (also referred to herein as an "empty" complex) comprising lipid binding protein molecules, CDN binding moieties, amphipathic molecules if present and, if present, anchors and/or linkers with (ii) one or more CDNs.

In some embodiments, the method further comprises a step of making the CDN-free complex.

In some embodiments, the method further comprises a mixing step after combining the CDN-free complex and the CDNs.

In another aspect, the disclosure provides a method of producing a complex of the disclosure comprising pre-complexing the CDN with the CDN binding moiety and, subsequently, combining (i) the pre-complexed CDN and CDN binding moiety with (ii) lipid binding protein molecules and, if present, amphipathic molecules and anchors and/or linkers.

Cargomer-based complexes can be prepared, for example, by mixing two organic solutions, one containing an apolipoprotein and the other one containing a charged amphipathic molecule, then removing the solvent by methods such as evaporation, freeze-drying (lyophilization), heating or any other method known in the art. Cargomers can also be prepared by mixing two aqueous solutions, one containing an apolipoprotein and the other one containing a charged amphipathic molecule, until an homogeneous solution is obtained. Cargomers can also be prepared by hydrating an apolipoprotein with an aqueous solution of charged amphipathic molecules, then mixing until an homogeneous solution is obtained. The solutions used to make Cargomers, e.g., aqueous solutions, can be at room temperature, at a higher temperature than room temperature, or at a lower temperature than room temperature during formation of the Cargomers. Alternatively, the solutions can be thermal cycled between a higher and lower temperature, e.g., as described in Example 1 or WO 2012/109162, preferably until Cargomers of at least 85%, at least 90%, at least 95% or at least 98% homogeneity are obtained. If the solution comprising the amphipathic molecules does not contain the CDN binding moieties, a solution comprising the CDN binding moieties (and anchors and/or linkers, if present) can be combined and mixed with the solution containing the apolipoprotein and amphipathic molecules prior to complex formation (e.g., before thermal cycling).

Without being bound by theory, it is believed that the process of making Cargomers results in the formation of multiple species of Cargomers having different numbers of apolipoprotein molecules in equilibrium. It is known in the art that the self-association of lipid-free ApoA-I is influenced by conditions such as pH, concentration, ionic strength, and temperature (see, e.g., Gianazza et al., 1997, Biochemistry, 36:7898-7905; Jayaraman et al., Journal of Biological Chemistry, 286 (41): 35610-35623; Schonfeld et al., 2016 J. Phys. Chem. B, 120:1228-1235) and it is believed that the equilibrium between different Cargomer species is similarly influenced by pH, concentration, ionic strength, and temperature. For example, acidic pH promotes formation of monomeric ApoA-I whereas alkaline pH encourages formation of multimeric forms, low concentrations of ApoA-I favor monomeric ApoA-I whereas high concentrations favor multimeric forms, and monomeric forms of ApoA-I are favored as temperature increases or decreases from ApoA-I's self-association maximum of 22° C.

Cargomers having a defined number of apolipoprotein molecules can be prepared in an aqueous solution by defining the appropriate pH, the concentration of apolipoprotein monomers and amphipathic molecules, the ionic strength and the temperature to make a solution of "empty" Cargomers. Cargo moieties (such as CDN binding moieties) can be added to the solution of empty Cargomers as a solution or as a powder in order to make loaded Cargomers having a defined molar ratio of apolipoprotein to cargo moieties. The loaded Cargomers can be used directly after being formed or can be purified in order to separate loaded Cargomers from unbound molecules (e.g., unbound cargo moieties).

When cargo molecules are not easily soluble in aqueous solutions, the apolipoprotein, amphipathic molecules and the cargo moieties to be included in a Cargomer can be solubilized in an organic solvent solution in order to make a homogeneous solution and avoid any aggregates or precipitates. Then the solvent can be removed by any suitable technique known in the art for removing a solvent from a solution, such as but not limited to evaporation, freeze-drying, spray-drying, etc. in order to make a solid powder or film in which the apolipoprotein, amphipathic molecules, and cargo moieties have been intimately mixed. An aqueous solution with the appropriate pH and ionic strength can be added to the powder or film to solubilize the molecules to spontaneously form loaded Cargomers at the appropriate concentrations. Addition of the aqueous solution can be done at a fixed temperature or, right after the addition, the mixture can be heated at a temperature up to 80 degrees Celsius. The mixture can also be thermal cycled (e.g., between 2 and 10 cycles) between a low temperature (e.g., no lower than 10 degrees Celsius) and a higher temperature (e.g., not exceeding 80 degrees Celsius) to form the Cargomers. Among organic solvents, para-xylene, ortho-xylene or acetic acid solutions are preferred for freeze drying. In some embodiments, acetic acid solutions from 70 to 100% are used. Other solvents or mixtures of solvents can be used and be later eliminated by different techniques for removing solvents that are well-known in the art. Solvents can be selected in order to solubilize each component of the Cargomers. In the case of a mixture of solvents, they should be miscible together. After hydration (addition of the aqueous solution) the Cargomers can be purified by any appropriate technique known in the art such as but not limited to chromatography, filtration, electrophoresis, etc. in order to eliminate unbound material or used without further separation/purification. After hydration (addition of the aqueous solution), pH can be adjusted and/or ionic strength can be adjusted, and/or osmolality can be adjusted.

HDL and HDL mimetic-based complexes can be made according to methods for making HDL and HDL mimetic complexes known in the art, for example as described in WO 2012/109162 and U.S. Pat. No. 8,821,939. Such methods include thermal cycling, homogenization, sonication, and lyophilization. CDN binding moieties, optionally attached to anchors and/or linkers, can be can be combined with the lipid binding protein component and/or lipid component of an HDL or HDL mimetic complex prior to complex formation. CDNs can be pre-complexed with the CDN binding moieties prior to complex formation, or can be added to a pre-formed composition comprising empty complexes to make complexes having bound CDNs.

6.4. Uses of CDN Carrying Complexes

The CDN containing complexes and pharmaceutical compositions of the disclosure can be used to treat a subject for a disease or condition treatable with a CDN, for example the diseases and conditions identified in Sections 6.4.1 to 6.4.3.

In one aspect, the disclosure provides a method of treating a subject, comprising administering to a subject in need thereof a therapeutically effective amount of a complex of the disclosure or a pharmaceutical composition of the disclosure.

In another aspect, the disclosure provides a method of administering a CDN to a subject comprising administering an amount of a CDN containing complex of the disclosure or a pharmaceutical composition of the disclosure to the subject.

In one aspect, the disclosure provides a method of treating a subject afflicted with a disease or condition associated with or modulated by STING comprising administering an amount of a CDN containing complex of the disclosure or a pharmaceutical composition of the disclosure to the subject. Diseases and conditions associated with or modulated by STING include inflammation, allergic and autoimmune diseases, infectious diseases and cancer.

CDN containing complexes of the disclosure and pharmaceutical compositions of the disclosure can be administered to a subject according to any suitable administration regimen, for example, weekly, twice a week, or daily. The complexes and pharmaceutical compositions can be administered for a set number of doses, (e.g., 1 to 24 doses, 1 to 12 doses, or 12 to 24 doses), such as when the complexes contain an anti-infective agent, or can be administered until a disease or condition that the subject is afflicted with subsides. In some embodiments, administration of a complex or pharmaceutical composition can be repeated after verification that a biological marker of a disease or condition has regressed.

The CDN containing complexes and compositions can be administered in the methods of the disclosure to a subject (which is preferably a mammal and most preferably a human) by any suitable route. For example, administration can be via injection (e.g., subcutaneous, intradermal, intravenous, or intraperitoneal injection), inhalation (e.g., intranasal or intrapulmonary inhalation), implantation, optionally (e.g., via a suppository), or ocular or intraocular routes (e.g., via eye drops). In some embodiments, the solution is administered as a depot injection. In some embodiments, a composition of the disclosure is administered as a perfusion over 15 to 24 hours (e.g., 15 minutes to 1 hour, 1 hour to 3 hours, 3 hours to 6 hours, 6 hours to 12 hours, or 12 hours to 24 hours).

6.4.1. Inducing an Immune Response

The CDN containing complexes of the disclosure, pharmaceutical compositions of the disclosure, and vaccine compositions of the disclosure can be used to induce an immune response in a subject in need thereof.

In one aspect, the disclosure provides a method of inducing an immune response in a subject, comprising administering to a subject in need thereof a therapeutically effective amount of a complex of the disclosure or a pharmaceutical composition of the disclosure.

Complexes comprising an immunogen and vaccine compositions of the disclosure can be used to immunize a subject by administering an effective amount of such a complex or vaccine composition to the subject. The methods of immunizing a subject can comprise administering an effective amount of the complex or vaccine composition alone or in combination with an effective amount of a second complex or composition comprising the second complex. Preferably, the complex and second complex comprise different cargo moieties. The complex and the second complex (or compositions thereof) can be administered sequentially or simultaneously. When administered simultaneously, complexes having different cargo moieties can be formulated into a single composition or be formulated in two separate compositions.

Complexes configured to activate an immune response and vaccine compositions containing such complexes are useful for treating a subject having or being predisposed to any disease or disorder to which the subject's immune system mounts an immune response. The compositions are useful as prophylactic vaccines, which confer resistance in a subject to subsequent exposure to infectious agents. The compositions are also useful as therapeutic vaccines, which can be used to initiate or enhance a subject's immune response to a pre-existing antigen, such as a tumor antigen in a subject with cancer, or a viral antigen in a subject infected with a virus. The compositions are also useful as desensitizing vaccines, which function to make an individual tolerant to an environmental antigen, such as an allergen.

Subjects with or at risk for immunosuppressed conditions can be treated therapeutically or prophylactically with complexes configured to activate an immune response as disclosed herein. The complexes disclosed herein can be used for treatment of disease conditions characterized by immunosuppression, including, but not limited to, AIDS or AIDS-related complex, idiopathic immuno suppression, drug induced immunosuppression, other virally or environmentally-induced conditions, and certain congenital immune deficiencies. Such complexes can also be employed to increase immune function that has been impaired by the use of radiotherapy of immunosuppressive drugs (e.g., certain chemotherapeutic agents), and therefore can be particularly useful when used in conjunction with such drugs or radiotherapy.

Subjects with or at risk for coronary heart disease and/or elevated LDL-C levels can be treated therapeutically or prophylactically with complexes configured to activate an immune response as disclosed herein. Embodiments of the disclosure wherein complexes include a PCSK9-antigen and a CpG-adjuvant address such needs. Indeed, vaccination against PCSK9 with such complexes can be used to inhibit interaction between PCSK9 and LDLR, while avoiding the need for repeated injections of expensive mAb.

6.4.2. Cancer Treatment

The CDN containing complexes of the disclosure, pharmaceutical compositions of the disclosure, and vaccine compositions of the disclosure can be used to treat subjects having cancer.

In one aspect, the disclosure provides a method of treating a subject afflicted with cancer (e.g., subjects with tumors resistant to PD-1 blockade), comprising administering a therapeutically effective amount of a complex of the disclosure or a pharmaceutical composition of the disclosure to the subject.

The methods of treatment can comprise administering a therapeutically effective amount of a complex or a pharmaceutical composition containing the complex to the subject alone or in combination with a therapeutically effective amount of a second complex or composition comprising the second complex (e.g., a second pharmaceutical composition). Preferably, the complex and second complex comprise different cargo moieties. The complex and the second complex (or compositions thereof) can be administered sequentially or simultaneously. When administered simultaneously, complexes having different cargo moieties can be formulated into a single composition or be formulated in two separate compositions.

Complexes comprising a neo-antigenic peptide can be used to induce a neoplasia/tumor specific immune response in a subject, vaccinate against a neoplasia/tumor, treat and/or alleviate a symptom of cancer in a subject by administering to the subject a therapeutically effective amount of such a complex or a vaccine composition comprising the complex. Such complexes and vaccine compositions may be used for a subject that has been diagnosed as having cancer, or at risk of developing cancer. In some embodiments, the subject has a solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas. The complex or vaccine composition can be administered in an amount sufficient to induce a CTL response, alone or in combination with other therapeutic agents (e.g., a chemotherapeutic or biotherapeutic agent, radiation, immunotherapy, or an anti-immunosuppressive or immunostimulatory agent). For example, a subject having melanoma can be administered a complex or vaccine composition of the disclosure in combination with another therapeutic agent used to treat melanoma (e.g., aldesleukin, cobimetinib, dabrafenib, dacarbazine, talimogene laherparepvec, recombinant interferon alfa-2b, ipilimumab, pembrolizumab, trametinib, nivolumab, peginterferon alfa-2a, peginterferon alfa-2b, or orvemurafenib).

In some embodiments, a complex or vaccine composition of the disclosure is administered to a subject diagnosed as having cancer or at risk of developing cancer in combination with an immunotherapy agent. Exemplary immunotherapy agents include alemtuzumab, atezolizumab, ipilimumab, ofatumumab, nivolumab, pembrolizumab, rituximab, and rurvalumab.

In some embodiments, a complex or vaccine composition of the disclosure is administered to a subject diagnosed as having cancer or at risk of developing cancer in combination with an immunotherapy agent which is a checkpoint inhibitor. Exemplary checkpoint inhibitors include atezolizumab, ipilimumab, pembrolizumab, and nivolumab.

In some embodiments, a complex or vaccine composition of the disclosure is administered to a subject diagnosed as having cancer or at risk of developing cancer in combination with an antibody-drug conjugate (ADC) comprising an anti-cancer agent (e.g., as described in Section 6.1.9.2). Exemplary ADCs include gemtuzumab ozogamicin (approved to treat acute myeloid leukemia), brentuximab vedotin (approved to treat Hodgkin lymphoma), trastuzumab emtansine (approved to treat HER2-positive metastatic breast cancer), and Inotuzumab ozogamicin (approved to treat acute lymphoblastic leukemia).

In some embodiments, the subject treated according to the methods of the disclosure has a tumor. In some embodiments, the tumor is stage T1 or higher according to according to the TNM classification system. In some embodiments, the tumor is stage T1 according to according to the TNM classification system. In some embodiments, the tumor is stage T2 or higher according to according to the TNM classification system. In some embodiments, the tumor is stage T2 according to according to the TNM classification system. In some embodiments, the tumor is stage T3 or higher according to according to the TNM classification system. In some embodiments, the tumor is stage T3 according to according to the TNM classification system. In some embodiments, the tumor is stage T4 according to according to the TNM classification system. In some embodiments, the tumor is a primary tumor. In some embodiments, the tumor is a secondary tumor.

In some embodiments, cells in the tumor overexpress or are suspected of overexpressing scavenger receptor B1 (SR-B1). In some embodiments, cells in the tumor overexpress SR-B1. In some embodiments, the cells in the tumor that overexpress SR-B1 comprise tumor associated macrophages (TAMs). In some embodiments, the cells in the tumor that overexpress SR-B1 comprise cancer cells.

In some embodiments, cells in the tumor express or overexpress KRAS. In some embodiments, the KRAS has one or more mutations.

In some embodiments, cells in the tumor express or overexpress nerve growth factor (NGF). In some embodiments, the NGF has one or more mutations.

In some embodiments, cells in the tumor express or overexpress signal transducer and activator of transcription 3 (STAT3). In some embodiments, the STAT3 has one or more mutations.

In some embodiments, cells in the tumor express or overexpress Hungtintin. In some embodiments, the Huntingtin has one or more mutations.

In some embodiments, the tumor is an esophageal tumor, a breast tumor, an ovarian tumor, a prostate tumor, a lung tumor, a kidney tumor, a gastric tumor, a colon tumor, a testicular tumor, a head and neck tumor, a pancreas tumor, a bladder tumor, a thyroid tumor or a brain tumor.

In some embodiments, the tumor is an esophageal tumor. In some embodiments, the tumor is a breast tumor. In some embodiments, the tumor is an ovarian tumor. In some embodiments, the tumor is a prostate tumor. In some embodiments, the tumor is a lung tumor. In some embodiments, the tumor is a kidney tumor. In some embodiments, the tumor is a gastric tumor. In some embodiments, the tumor is a colon tumor. In some embodiments, the tumor is a testicular tumor. In some embodiments, the tumor is a head and neck tumor. In some embodiments, the tumor is a pancreas tumor. In some embodiments, the tumor is a bladder tumor. In some embodiments, the tumor is a thyroid tumor. In some embodiments, the tumor is a brain tumor.

In some embodiments, the subject is afflicted with acute myeloid leukemia, adrenal cancer, anal cancer, basal cell skin cancer, squamous cell skin cancer bile duct cancer, bladder cancer, bone cancer, brain cancer, breast cancer, castleman disease, cervical cancer, chronic lymphocytic leukemia, chronic myeloid leukemia, chronic myelomonocytic leukemia, colorectal cancer, endometrial cancer, esophageal cancer, ewing sarcoma, eye cancer, gallbladder cancer, gastrointestinal cancer, hodgkin lymphoma, kaposi sarcoma, kidney cancer, laryngeal cancer, hypopharyngeal cancer, leukemia, liver cancer, lung cancer, lymphoma, malignant mesothelioma, melanoma skin cancer, merkel cell skin cancer, multiple myeloma, myelodysplastic syndromes, nasal cavity cancer, paranasal sinuses cancer, nasopharyngeal cancer, neuroblastoma, non-hodgkin lymphoma, non-small cell lung cancer, oral cavity cancer, oropharyngeal cancer, osteosarcoma, ovarian cancer, pancreatic cancer, penile cancer, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer, uterine sarcoma, vaginal cancer, vulvar cancer, or waldenstrom macroglobulinemia.

In some embodiments, the subject is afflicted with acute myeloid leukemia. In some embodiments, the subject is afflicted with adrenal cancer. In some embodiments, the subject is afflicted with anal cancer. In some embodiments, the subject is afflicted with basal cell skin cancer. In some embodiments, the subject is afflicted with squamous cell skin cancer. In some embodiments, the subject is afflicted with bile duct cancer. In some embodiments, the subject is afflicted with bladder cancer. In some embodiments, the subject is afflicted with bone cancer. In some embodiments, the subject is afflicted with brain cancer. In some embodiments, the subject is afflicted with breast cancer. In some embodiments, the subject is afflicted with castleman disease. In some embodiments, the subject is afflicted with cervical cancer. In some embodiments, the subject is afflicted with chronic lymphocytic leukemia. In some embodiments, the subject is afflicted with chronic myeloid leukemia. In some embodiments, the subject is afflicted with chronic myelomonocytic leukemia. In some embodiments, the subject is afflicted with colorectal cancer. In some embodiments, the subject is afflicted with endometrial cancer. In some embodiments, the subject is afflicted with esophageal cancer. In some embodiments, the subject is afflicted with ewing sarcoma. In some embodiments, the subject is afflicted with eye cancer. In some embodiments, the subject is afflicted with gallbladder cancer. In some embodiments, the subject is afflicted with gastrointestinal cancer. In some embodiments, the subject is afflicted with hodgkin lymphoma. In some embodiments, the subject is afflicted with kaposi sarcoma. In some embodiments, the subject is afflicted with kidney cancer. In some embodiments, the subject is afflicted with laryngeal cancer. In some embodiments, the subject is afflicted with hypopharyngeal cancer. In some embodiments, the subject is afflicted with leukemia. In some embodiments, the subject is afflicted with liver cancer. In some embodiments, the subject is afflicted with lung cancer. In some embodiments, the subject is afflicted with lymphoma. In some embodiments, the subject is afflicted with malignant mesothelioma. In some embodiments, the subject is afflicted with melanoma skin cancer. In some embodiments, the subject is afflicted with merkel cell skin cancer. In some embodiments, the subject is afflicted with multiple myeloma. In some embodiments, the subject is afflicted with myelodysplastic syndromes. In some embodiments, the subject is afflicted with nasal cavity cancer. In some embodiments, the subject is afflicted with paranasal sinuses cancer. In some embodiments, the subject is afflicted with nasopharyngeal cancer. In some embodiments, the subject is afflicted with neuroblastoma. In some embodiments, the subject is afflicted with non-hodgkin lymphoma. In some embodiments, the subject is afflicted with non-small cell lung cancer. In some embodiments, the subject is afflicted with oral cavity cancer. In some embodiments, the subject is afflicted with oropharyngeal cancer. In some embodiments, the subject is afflicted with osteosarcoma. In some embodiments, the subject is afflicted with ovarian cancer. In some embodiments, the subject is afflicted with pancreatic cancer. In some embodiments, the subject is afflicted with penile cancer. In some embodiments, the subject is afflicted with prostate cancer. In some embodiments, the subject is afflicted with retinoblastoma. In some embodiments, the subject is afflicted with rhabdomyosarcoma. In some embodiments, the subject is afflicted with salivary gland cancer. In some embodiments, the subject is afflicted with skin cancer. In some embodiments, the subject is afflicted with small cell lung cancer. In some embodiments, the subject is afflicted with small intestine cancer. In some embodiments, the subject is afflicted with soft tissue sarcoma. In some embodiments, the subject is afflicted with stomach cancer. In some embodiments, the subject is afflicted with testicular cancer. In some embodiments, the subject is afflicted with thymus cancer. In some embodiments, the subject is afflicted with thyroid cancer. In some embodiments, the subject is afflicted with uterine sarcoma. In some embodiments, the subject is afflicted with vaginal cancer. In some embodiments, the subject is afflicted with vulvar cancer. In some embodiments, the subject is afflicted with waldenstrom macroglobulinemia.

In some embodiments, administration of the complex is before and/or after surgery to remove a tumor from the subject.

In some embodiments, the method further comprises administering an anti-cancer therapy to the subject. In some embodiments, the anti-cancer therapy comprises radiation. In some embodiments, wherein the anti-cancer therapy comprises an anti-cancer agent.

In some embodiments, the anti-cancer agent comprises an antibody, a topoisomerase inhibitor, a DNA alkylating agent, a DNA strand break inducing agent, an anti-microtubule agent, an anti-metabolic agent, an anthracycline, a *vinca* alkaloid, or an epipodophyllotoxin, a tyrosine kinase inhibitor, a CDK inhibitor, a MAP kinase inhibitor, an EGFR inhibitor, a VEGF inhibitor, an immunotherapy agent, a checkpoint inhibitor, a neo-antigen, a siRNA, an antisense oligonucleotide, or a combination thereof.

In some embodiments, the anti-cancer agent comprises an antibody. In some embodiments, the anti-cancer agent comprises a topoisomerase inhibitor. In some embodiments, the anti-cancer agent comprises a DNA alkylating agent. In some embodiments, the anti-cancer agent comprises a DNA strand break inducing agent. In some embodiments, the anti-cancer agent comprises an anti-microtubule agent. In some embodiments, the anti-cancer agent comprises an anti-metabolic agent. In some embodiments, the anti-cancer agent comprises an anthracycline. In some embodiments, the anti-cancer agent comprises a *vinca* alkaloid. In some embodiments, the anti-cancer agent comprises an epipodophyllotoxin. In some embodiments, the anti-cancer agent comprises a tyrosine kinase inhibitor. In some embodiments, the anti-cancer agent comprises a CDK inhibitor. In some embodiments, the anti-cancer agent comprises a MAP kinase inhibitor. In some embodiments, the anti-cancer agent comprises an EGFR inhibitor. In some embodiments, the anti-cancer agent comprises a VEGF inhibitor. In some embodiments, the anti-cancer agent comprises an immunotherapy agent. In some embodiments, the anti-cancer agent comprises a checkpoint inhibitor. In some embodiments, the anti-cancer agent comprises a neo-antigen. In some embodiments, the anti-cancer agent comprises a siRNA. In some embodiments, the anti-cancer agent comprises an antisense oligonucleotide. In some embodiments, the anti-cancer agent is in the form of an antibody-drug conjugate (ADC).

In some embodiments, the anti-cancer agent is in the form of a lipoprotein complex comprising the anti-cancer agent. In some embodiments, the lipoprotein complex comprising the anti-cancer agent comprises CER-001, CSL-111, CSL-112, or ETC-216. In some embodiments, the lipoprotein complex comprising an anti-cancer agent comprises CER-001. In some embodiments, the lipoprotein complex comprising an anti-cancer agent comprises CSL-111. In some embodiments, the lipoprotein complex comprising an anti-cancer agent comprises CSL-112. In some embodiments, the lipoprotein complex comprising an anti-cancer agent comprises ETC-216.

6.4.3. Infection and Infectious Disease Treatment

The CDN containing complexes of the disclosure and pharmaceutical compositions of the disclosure can be used to treat subjects having an infection or infectious disease.

In one aspect, the disclosure provides a method of treating an infection or infectious disease in a subject, comprising administering to a subject in need thereof a therapeutically effective amount of a complex of the disclosure or the pharmaceutical composition of the disclosure.

In some embodiments, the method further comprises administering an anti-infective agent so the subject. In some embodiments, the anti-infective agent comprises an anti-bacterial agent, an anti-viral agent, an anti-parasitic agent, an anti-fungal agent, or an anti-mycobacterial agent. In some embodiments, the anti-infective agent comprises an anti-bacterial agent, optionally wherein the anti-bacterial agent is a β-lactam antibiotic, a penicillin, a cephalosporin, a β-lactamase inhibitor, vancomycin, an aminoglycoside, a tetracycline, chloramphenicol, erythromycin, lincomycin, clindamycin, rifampin, metronidazole, a polymyxin, a sulfonamide, or a quinoline. In some embodiments, the anti-infective agent comprises an anti-viral agent, optionally wherein the anti-viral agent is amantadine, rimantadine, ribivarin, acyclovir, vidarabine, trifluorothymidine, ganciclovir, zidovudine, retinovir, or an interferon. In some embodiments, the anti-infective agent comprises an anti-fungal agent, optionally wherein the anti-fungal agent is an imidazole, a triazoles, a polyene macrolide antibiotic, griseofulvin, amphotericin B, or flucytosine. In some embodiments, the anti-infective agent comprises an anti-parasitic agent.

7. SEQUENCE LISTING

| SEQ ID NO | Sequence | Description |
|---|---|---|
| 1 | DEPPQSPWDR VKDLATVYVD VLKDSGRDYV SQFEGSALGK QLNLKLLDNW DSVTSTESKL REQLGPVTQE FWDNLEKETE GLRQEMSKDL EEVKAKVQPY LDDFQKKWQE EMELYRQKVE PLRAELQEGA RQKLHELQEK LSPLGEEMRD RARAHVDALR THLAPYSDEL RQRLAARLEA LKENGGARLA EYHAKATEHL STLSEKAKPA LEDLRQGLLP VLESEKVSFL SALEEYTKKL NTQ | ApoA-I amino acid sequence (mature) |
| 2 | GAUGUAACUGAAUGAAAUGGUGAAGGACGGGUCCAAAUAGGGAAGCAA CGAAGCAUAGCCUUUAUAUGGAACACUUGGGUUAUGUGGAGCUACUAG UGUAACCAGCCCUUCCUUUUGUUGAGUAGAGUGUGAGCUCCGUAACUA GUUACAUC | Exemplary LFO |
| 3 | UCCAAAUAGGGAAGCAACGAAGCAUAGCCUUUAUAUGGAACACUUGGG UUAUGUGGAGCUACUAGUGUAACCAGCCCUUCCUUUUGUUGA | Exemplary LFO |
| 4 | AAUAGGGAAGCAACGAAGUGGAGCUACUAGUGUAACCAGCCCUUCCUU | Exemplary LFO |
| 5 | UCCAAAUAGGGAAGCAACGAAGUGGAGCUACUAGUGUAACCAGCCCUU CCUUUUGUUGA | Exemplary LFO |
| 6 | UCCAAAAGGGAAGCAACGAAGUGGAGCUACUAGUGUAACCAGCCCUUU UGGA | Exemplary LFO |
| 7 | AAAGGGAAGCAACGAAGUGGAGCUACUAGUGUAACCAGCCCUUU | Exemplary LFO |

-continued

| SEQ ID NO | Sequence | Description |
|---|---|---|
| 8 | GGGUUGGUGGUAAGCGAUAAUACUAAACCAUUCGCGAGAAUGGGGCGG AAAGCCUAUAGGGUCUCCCUGAGACAGCGGGUUGCCGAAAUAUCACGC GAUAU | Exemplary LFO |
| 9 | GGGUUGGUGGUAAGCGAUAAUGCUAAACCAUUCGCGAGAAUGGGGCGG AAAGCCUAUAGGGUCUCCCUGAGACAGCGGGUUGCCGAAAUAUCACGC GAUAU | Exemplary LFO |
| 10 | CUCCGAUAUCGACAAUACUAAACCAUCCGCGAGGGUGGGACGGAAAGC UACCAGGGUCUCUCUGAGACAGCCGGGAUGCCGAAAUAUCACAAUUUU UUUUUUUUUGUCCCGGCAUUCUUUUU | Exemplary LFO |
| 11 | UCAGAUACACGACAAUACUAAACCAUCCGCGAGGAUGGGGCGAAAGCC UAAGGGUCUCCCUGAGACAGCCGGGUGCCGUGUAUCUGA | Exemplary LFO |
| 12 | GGUCAGAUACACGACAAUACUAAACCAUCCGCGAGGAUGGGGCGGAAA GCCUAAGGGUCUCCCUGAGACAGCCGGGUCGCCGAAAUAUCUGAACGA UAUCAGGCCCCGGCUUUUUGU | Exemplary LFO |
| 13 | GGUACACGACAAUACUAAACCAUCCGCGAGGAUGGGGCGGAAAGCCUA AGGGUCUCCCUGAGACAGCCGGGCUGCCGAAAUAUC | Exemplary LFO |
| 14 | GGUCACGCACAGAGCAACCAUUCGAAAGAGUGGGACGCAAAGCCUCCG GCCUAAACCAUUGCACUCCGGUAGGUAGCGGUUACCGAUGG | Exemplary LFO |
| 15 | GAUAUCGACAAUACUAAACCAUCCGCGAGGGUGGGACGGAAAGCCUAC AGGGUCUCUCUGAGACAGCCGGGAUGCCGAAAUAUC | Exemplary LFO |
| 16 | GAUGUAACUGAAUGAAAUGGUGAAGGACGGGUCCAAAUAGGGAAGCAA CGAAGCAUAGCCUUUAUAUGGACACUUGGGUUAUGUGGAGCUACUAGU GUAACCGGCCCUCCUUUUGUUGAGUAGAGUGUGAGCUCCGUAACUAGU UACAUC | Exemplary LFO |
| 17 | GGUCACGCACAGGGCAAACCAUUCGAAAGAGUGGGACGCAAAGCCUCC GGCCUAAACCAUUGCACUCCGGUAGGUAGCGGGGUUACCGAUGG | Exemplary LFO |
| 18 | AAUAGGGAAG CAACGAAGCA UAGCCUUUAU AUGGACACUU GGGUUAUGUG GAGCUACUAG UGUAACCGGC CCUCCUU | Exemplary LFO |
| 19 | 5'-GGGGGACGA:TCGTCGGGGGG-3' (20 mer) | Class A CpG |
| 20 | 5'- GGGGACGAC:GTCGTGGGGGGG-3' (21 mer) | Class A CpG |
| 21 | 5'-TCGTCGTTTTGTCGTTTTGTCGTT-3' (24 mer) | Class B CpG |
| 22 | 5'-TCGACGTTCGTCGTTCGTCGTTC-3' (23 mer) | Class B CpG |
| 23 | 5'-TCGCGACGTTCGCCCGACGTTCGGTA-3' (26 mer) | Class B CpG |
| 24 | 5'-TCGTCGTTTTCGGCGC:GCGCCG-3' (22 mer) | Class C CpG |
| 25 | 5'-TCGTCGTCGTTC:GAACGACGTTGAT-3' (25 mer) | Class C CpG |
| 26 | 5'-TCGCGAACGTTCGCCGCGTTCGAACGCGG-3' (29 mer) | Class C CpG |

8. SPECIFIC EMBODIMENTS

The present disclosure is exemplified by the specific embodiments below.

1. A complex for carrying one or more cyclic dinucleotides (CDNs), comprising:
   (a) one or more lipid binding protein molecules;
   (b) one or more CDNs;
   (c) one or more CDN binding moieties that (i) non-covalently bind the one or more CDNs and (ii) indirectly couple the one or more CDNs to the one or more lipid binding protein molecules;
   (d) optionally, an amount of amphipathic molecules sufficient to solubilize the lipid binding protein molecules;
   (e) optionally, one or more anchors non-covalently coupling one or more CDN binding moieties to the lipid binding protein molecules; and
   (f) optionally, one or more linkers covalently coupling one or more CDN binding moieties to one or more lipid binding protein molecules, one or more amphipathic molecules or one or more anchors.

2. The complex of embodiment 1, which comprises amphipathic molecules.

3. The complex of embodiment 1 or embodiment 2, wherein the CDN binding moiety is positively charged at physiological pH.

4. The complex of any one of embodiments 1 to 3, wherein the CDN binding moiety comprises a positively charged peptide.

5. The complex of embodiment 4, wherein the positively charged peptide comprises lysine residues, arginine residues, ornithine residues, histidine residues, or a combination thereof.

6. The complex of embodiment 5, wherein the positively charged peptide further comprises one or more uncharged amino acids, such as glycine.

7. The complex of embodiment 6, wherein the positively charged peptide comprises an uncharged amino acid between charged amino acids.

8. The complex of any one of embodiments 5 to 7, wherein the positively charged peptide comprises 2 to 8 lysine residues.

9. The complex of any one of embodiments 5 to 7, wherein the positively charged peptide comprises 2 to 8 arginine residues.

10. The complex any one of embodiments 5 to 7, wherein the positively charged peptide comprises 2 to 8 ornithine residues.

11. The complex any one of embodiments 5 to 7, wherein the positively charged peptide comprises 2 to 8 histidine residues.

12. The complex of any one of embodiments 1 to 11, wherein the CDN binding moiety has a positive charge of +2 to +8 at physiological pH.

13. The complex of any one of embodiments 4 to 12, wherein the net charge of the CDN and the CDN binding moiety taken together is 0, 1, or 2.

14. The complex of embodiment 1 or embodiment 2, wherein the CDN binding moiety comprises a loop forming oligonucleotide (LFO).

15. The complex of embodiment 14, wherein the LFO is 20 to 150 nucleotides in length.

16. The complex of embodiment 15, wherein the LFO is 20 to 140 nucleotides in length.

17. The complex of embodiment 15, wherein the LFO is 20 to 130 nucleotides in length.

18. The complex of embodiment 15, wherein the LFO is 20 to 120 nucleotides in length.

19. The complex of embodiment 15, wherein the LFO is 20 to 110 nucleotides in length.

20. The complex of embodiment 15, wherein the LFO is 20 to 100 nucleotides in length.

21. The complex of embodiment 15, wherein the LFO is 20 to 90 nucleotides in length.

22. The complex of embodiment 15, wherein the LFO is 20 to 80 nucleotides in length.

23. The complex of embodiment 15, wherein the LFO is 20 to 70 nucleotides in length.

24. The complex of embodiment 15, wherein the LFO is 20 to 60 nucleotides in length.

25. The complex of embodiment 15, wherein the LFO is 20 to 50 nucleotides in length.

26. The complex of embodiment 15, wherein the LFO is 20 to 40 nucleotides in length.

27. The complex of embodiment 15, wherein the LFO is 20 to 30 nucleotides in length.

28. The complex of embodiment 15, wherein the LFO is 30 to 150 nucleotides in length.

29. The complex of embodiment 15, wherein the LFO is 30 to 140 nucleotides in length.

30. The complex of embodiment 15, wherein the LFO is 30 to 130 nucleotides in length.

31. The complex of embodiment 15, wherein the LFO is 30 to 120 nucleotides in length.

32. The complex of embodiment 15, wherein the LFO is 30 to 110 nucleotides in length.

33. The complex of embodiment 15, wherein the LFO is 30 to 100 nucleotides in length.

34. The complex of embodiment 15, wherein the LFO is 30 to 90 nucleotides in length.

35. The complex of embodiment 15, wherein the LFO is 30 to 80 nucleotides in length.

36. The complex of embodiment 15, wherein the LFO is 30 to 70 nucleotides in length.

37. The complex of embodiment 15, wherein the LFO is 30 to 60 nucleotides in length.

38. The complex of embodiment 15, wherein the LFO is 30 to 50 nucleotides in length.

39. The complex of embodiment 15, wherein the LFO is 30 to 40 nucleotides in length.

40. The complex of embodiment 15, wherein the LFO is 40 to 150 nucleotides in length.

41. The complex of embodiment 15, wherein the LFO is 40 to 140 nucleotides in length.

42. The complex of embodiment 15, wherein the LFO is 40 to 130 nucleotides in length.

43. The complex of embodiment 15, wherein the LFO is 40 to 120 nucleotides in length.

44. The complex of embodiment 15, wherein the LFO is 40 to 110 nucleotides in length.

45. The complex of embodiment 15, wherein the LFO is 40 to 100 nucleotides in length.

46. The complex of embodiment 15, wherein the LFO is 40 to 90 nucleotides in length.

47. The complex of embodiment 15, wherein the LFO is 40 to 80 nucleotides in length.

48. The complex of embodiment 15, wherein the LFO is 40 to 70 nucleotides in length.

49. The complex of embodiment 15, wherein the LFO is 40 to 60 nucleotides in length.

50. The complex of embodiment 15, wherein the LFO is 40 to 50 nucleotides in length.

51. The complex of embodiment 15, wherein the LFO is 50 to 150 nucleotides in length.

52. The complex of embodiment 15, wherein the LFO is 50 to 140 nucleotides in length.

53. The complex of embodiment 15, wherein the LFO is 50 to 130 nucleotides in length.

54. The complex of embodiment 15, wherein the LFO is 50 to 120 nucleotides in length.

55. The complex of embodiment 15, wherein the LFO is 50 to 110 nucleotides in length.

56. The complex of embodiment 15, wherein the LFO is 50 to 100 nucleotides in length.

57. The complex of embodiment 15, wherein the LFO is 50 to 90 nucleotides in length.

58. The complex of embodiment 15, wherein the LFO is 50 to 80 nucleotides in length.

59. The complex of embodiment 15, wherein the LFO is 50 to 70 nucleotides in length.

60. The complex of embodiment 15, wherein the LFO is 50 to 60 nucleotides in length.

61. The complex of embodiment 15, wherein the LFO is 60 to 150 nucleotides in length.

62. The complex of embodiment 15, wherein the LFO is 60 to 140 nucleotides in length.

63. The complex of embodiment 15, wherein the LFO is 60 to 130 nucleotides in length.

64. The complex of embodiment 15, wherein the LFO is 60 to 120 nucleotides in length.

65. The complex of embodiment 15, wherein the LFO is 60 to 110 nucleotides in length.

66. The complex of embodiment 15, wherein the LFO is 60 to 100 nucleotides in length.

67. The complex of embodiment 15, wherein the LFO is 60 to 90 nucleotides in length.

68. The complex of embodiment 15, wherein the LFO is 60 to 80 nucleotides in length.

69. The complex of embodiment 15, wherein the LFO is 60 to 70 nucleotides in length.

70. The complex of embodiment 15, wherein the LFO is 70 to 150 nucleotides in length.

71. The complex of embodiment 15, wherein the LFO is 70 to 140 nucleotides in length.

72. The complex of embodiment 15, wherein the LFO is 70 to 130 nucleotides in length.

73. The complex of embodiment 15, wherein the LFO is 70 to 120 nucleotides in length.

74. The complex of embodiment 15, wherein the LFO is 70 to 110 nucleotides in length.

75. The complex of embodiment 15, wherein the LFO is 70 to 100 nucleotides in length.

76. The complex of embodiment 15, wherein the LFO is 70 to 90 nucleotides in length.

77. The complex of embodiment 15, wherein the LFO is 70 to 80 nucleotides in length.

78. The complex of embodiment 15, wherein the LFO is 80 to 150 nucleotides in length.

79. The complex of embodiment 15, wherein the LFO is 80 to 140 nucleotides in length.

80. The complex of embodiment 15, wherein the LFO is 80 to 130 nucleotides in length.

81. The complex of embodiment 15, wherein the LFO is 80 to 120 nucleotides in length.

82. The complex of embodiment 15, wherein the LFO is 80 to 110 nucleotides in length.

83. The complex of embodiment 15, wherein the LFO is 80 to 100 nucleotides in length.

84. The complex of embodiment 15, wherein the LFO is 80 to 90 nucleotides in length.

85. The complex of embodiment 15, wherein the LFO is 90 to 150 nucleotides in length.

86. The complex of embodiment 15, wherein the LFO is 90 to 140 nucleotides in length.

87. The complex of embodiment 15, wherein the LFO is 90 to 130 nucleotides in length.

88. The complex of embodiment 15, wherein the LFO is 90 to 120 nucleotides in length.

89. The complex of embodiment 15, wherein the LFO is 90 to 110 nucleotides in length.

90. The complex of embodiment 15, wherein the LFO is 90 to 100 nucleotides in length.

91. The complex of embodiment 15, wherein the LFO is 100 to 150 nucleotides in length.

92. The complex of embodiment 15, wherein the LFO is 100 to 140 nucleotides in length.

93. The complex of embodiment 15, wherein the LFO is 100 to 130 nucleotides in length.

94. The complex of embodiment 15, wherein the LFO is 100 to 120 nucleotides in length.

95. The complex of embodiment 15, wherein the LFO is 100 to 110 nucleotides in length.

96. The complex of embodiment 15, wherein the LFO is 110 to 150 nucleotides in length.

97. The complex of embodiment 15, wherein the LFO is 110 to 140 nucleotides in length.

98. The complex of embodiment 15, wherein the LFO is 110 to 130 nucleotides in length.

99. The complex of embodiment 15, wherein the LFO is 110 to 120 nucleotides in length.

100. The complex of embodiment 15, wherein the LFO is 120 to 150 nucleotides in length.

101. The complex of embodiment 15, wherein the LFO is 120 to 140 nucleotides in length. 102. The complex of embodiment 15, wherein the LFO is 120 to 130 nucleotides in length.

103. The complex of embodiment 15, wherein the LFO is 130 to 150 nucleotides in length.

104. The complex of embodiment 15, wherein the LFO is 130 to 140 nucleotides in length.

105. The complex of embodiment 15, wherein the LFO is 140 to 150 nucleotides in length.

106. The complex of any one of embodiments 14 to 105, wherein the LFO was identified using a computational method, for example as described in Chang et al., 2009, RNA, 15 (7): 1426-1430, Mukherjee and Sengupta, 2016, Bioinformatics, 32 (5): 776-8, or Singh et al., 2009, BMC Bioinformatics, 10:325, the contents of each of which are incorporated herein in their entireties.

107. The complex of any one of embodiments 14 to 106, wherein the LFO comprises RNA.

108. The complex of embodiment 107, wherein the LFO comprises a riboswitch or a loop forming portion thereof.

109. The complex of embodiment 108, wherein the LFO comprises a nucleotide sequence selected from the sequences in Table 2 or a loop forming portion thereof.

110. The complex of any one of embodiments 14 to 105, wherein the LFO comprises a nucleotide sequence selected from the sequences in Table 2.

111. The complex of any one of embodiments 14 to 105, wherein the LFO comprises DNA.

112. The complex of embodiment 111, wherein the LFO comprises a nucleotide sequence selected from the sequences in Table 2 when converted to DNA or a loop forming portion thereof.

113. The complex of any one of embodiments 14 to 105, wherein the LFO is a peptide nucleic acid (PNA).

114. The complex of any one of embodiments 14 to 113, wherein the LFO comprises one or more modifications that block or reduce the rate at which the LFO is degraded by nucleases in vivo.

115. The complex of embodiment 114 wherein, the one or more modifications comprises one or more phosphorothioate (PS) bonds in the LFO.

116. The complex of embodiment 114 or embodiment 115, wherein the one or more modifications comprises one or more 2'—O-methyl modifications in the LFO.

117. The complex of any one of embodiments 114 to 116, wherein the one or more modifications comprises one or more 2' fluoro bases in the LFO.

118. The complex of any one of embodiments 114 to 117, wherein the one or more modifications comprises an inverted ddT at the 5' end of the LFO.

119. The complex of any one of embodiments 114 to 118, wherein the one or more modifications comprises an inverted dT nucleotide at the 3' end of the LFO.

120. The complex of any one of embodiments 114 to 118, wherein the one or more modifications comprises a phosphorylation at the 3' end of the LFO.

121. The complex of any one of embodiments 1 to 120, wherein at least one CDN binding moiety is coupled to an anchor.

122. The complex of embodiment 121, wherein the anchor comprises an amphipathic and/or apolar moiety.

123. The complex of embodiment 122, wherein the anchor comprises an amphipathic moiety.

124. The complex of embodiment 123, wherein the amphipathic moiety comprises one of the amphipathic molecules of (d).

125. The complex of embodiment 123 or embodiment 124, wherein the amphipathic moiety comprises a lipid, a detergent, a fatty acid, an apolar molecule attached to a sugar, or a sterol attached to a sugar.

126. The complex of embodiment 125, wherein the amphipathic moiety comprise a lipid.

127. The complex of embodiment 126, wherein the lipid comprises a phospholipid.

128. The complex of embodiment 124, wherein the amphipathic moiety comprises a sterol.

129. The complex of embodiment 128, wherein the sterol comprise an animal sterol or a plant sterol.

130. The complex of embodiment 128, wherein the sterol comprises cholesterol.

131. The complex of embodiment 122, wherein the anchor comprises an apolar moiety.

132. The complex of embodiment 131, wherein the apolar moiety comprises an alkyl chain, an acyl chain, or a diacyl chain.

133. The complex of any one of embodiments 121 to 132, wherein the CDN binding moiety is coupled to the anchor by a direct bond.

134. The complex of any one of embodiments 121 to 132, wherein the CDN binding moiety is coupled to the anchor by a linker.

135. The complex of embodiment 134, wherein the linker coupling the CDN binding moiety to the anchor is a bifunctional linker.

136. The complex of embodiment 134 or 135, wherein the linker coupling the CDN binding moiety to the anchor is a cleavable linker.

137. The complex of embodiment 136, wherein the cleavable linker is a dipeptide linker.

138. The complex of embodiment 134 or 135, wherein the linker coupling the CDN binding moiety to the anchor is a non-cleavable linker.

139. The complex of any one of embodiments 1 to 138, wherein at least one CDN binding moiety is coupled to one of the one or more lipid binding protein molecules.

140. The complex of embodiment 139, wherein the CDN binding moiety is coupled to the lipid binding protein molecule by a direct bond.

141. The complex of embodiment 139, wherein the CDN binding moiety is coupled to the lipid binding protein molecule by a linker.

142. The complex of embodiment 141, wherein the linker coupling the CDN binding moiety to the lipid binding protein is a bifunctional linker.

143. The complex of embodiment 141 or embodiment 142, wherein the linker coupling the CDN binding moiety to the moiety to the lipid binding protein is a cleavable linker.

144. The complex of embodiment 143, wherein the cleavable linker coupling the CDN binding moiety to the lipid binding protein is a dipeptide linker.

145. The complex of embodiment 141 or embodiment 142, wherein the linker coupling the CDN binding moiety to the lipid binding protein is a non-cleavable linker.

146. The complex of any one of embodiments 1 to 145, wherein at least one CDN comprises two naturally occurring nucleobases.

147. The complex of embodiment 146, wherein the naturally occurring nucleobases are independently selected from adenine, guanine, cytosine, thymine, uracil, 5-methylcytosine, pseudouridine, dihydrouridine, inosine, 7-methylguanine, hypoxanthine, xanthine, 5,6-dihydrouracil, and 5-hydroxymethylcytosine.

148. The complex of embodiment 146, wherein the naturally occurring nucleobases are independently selected from adenine, guanine, cytosine, thymine, and uracil.

149. The complex of embodiment 146, wherein the naturally occurring nucleobases are independently selected from adenine and guanine.

150. The complex of any one of embodiments 1 to 149, wherein at least one CDN comprises one or two non-naturally occurring nucleobases.

151. The complex of embodiment 150, wherein at least one CDN comprises one non-naturally occurring nucleobase and one naturally occurring nucleobase.

152. The complex of embodiment 151, wherein the naturally occurring nucleobase is selected from adenine, guanine, cytosine, thymine, uracil, 5-methylcytosine, pseudouridine, dihydrouridine, inosine, 7-methylguanine, hypoxanthine, xanthine, 5,6-dihydrouracil, and 5-hydroxymethylcytosine.

153. The complex of embodiment 151, wherein the naturally occurring nucleobase is selected from adenine, guanine, cytosine, thymine, and uracil.

154. The complex of embodiment 151, wherein the naturally occurring nucleobase is selected from adenine and guanine.

155. The complex of embodiment 150, wherein at least one CDN comprises two non-naturally occurring nucleobases.

156. The complex of any one of embodiments 1 to 155, at least one CDN comprises a stable isotope, such as deuterium.

157. The complex of any one of embodiments 1 to 156, at least one CDN comprises a radioisotope, such as Carbon-14 or tritium.

158. The complex of any one of embodiments 1 to 157, wherein at least one CDN is a CDN of formula I:

Formula I where $N_1$ and $N_2$ are each an individually selected nucleobase, and $X_1$ and $X_2$ are each individually O or S.

159. The complex of any one of embodiments 1 to 158, wherein at least one CDN is a CDN of formula II:

Formula II

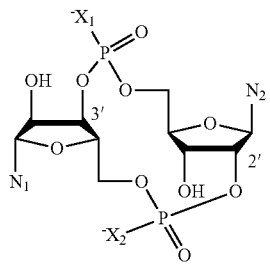

where $N_1$ and $N_2$ are each an individually selected nucleobase, and $X_1$ and $X_2$ are each individually O or S.

160. The complex of any one of embodiments 1 to 159, wherein at least one CDN is a CDN of formula III:

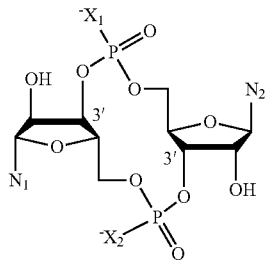

where $N_1$ and $N_2$ are each an individually selected nucleobase, and $X_1$ and $X_2$ are each individually O or S.

161. The complex of any one of embodiments 158 to 160, wherein $X_1$ is O.

162. The complex of any one of embodiments 158 to 160, wherein $X_1$ is S.

163. The complex of any one of embodiments 158 to 162, wherein $X_2$ is O.

164. The complex of any one of embodiments 158 to 162, wherein $X_2$ is S.

165. The complex of any one of embodiments 158 to 164, wherein $N_1$ and $N_2$ are each independently selected from adenine, guanine, cytosine, thymine, uracil, 5-methylcytosine, pseudouridine, dihydrouridine, inosine, 7-methylguanine, hypoxanthine, xanthine, 5,6-dihydrouracil, and 5-hydroxymethylcytosine.

166. The complex of any one of embodiments 158 to 164, wherein $N_1$ and $N_2$ are each independently selected from adenine, guanine, cytosine, thymine, and uracil.

167. The complex of any one of embodiments 158 to 164, wherein $N_1$ and $N_2$ are each individually selected from guanine and adenine.

168. The complex of any one of embodiments embodiment 158 to 167, wherein $N_1$ is guanine.

169. The complex of any one of embodiments embodiment 158 to 167, wherein $N_1$ is adenine.

170. The complex of any one of embodiments 158 to 169, wherein $N_2$ is guanine.

171. The complex of any one of embodiments 158 to 169, wherein $N_2$ is adenine.

172. The complex of any one of embodiments 1 to 171, wherein at least one CDN is a naturally occurring CDN.

173. The complex of any one of embodiments 1 to 172, wherein at least one CDN is a non-naturally occurring CDN.

174. The complex of embodiment 173, wherein at least one non-naturally occurring CDN comprises one or two thio substituted phosphate linkages.

175. The complex of any one of embodiments 1 to 174, wherein at least one CDN comprises cGAMP, c-di-GMP, or c-di-AMP.

176. The complex of any one of embodiments 1 to 175, wherein at least one CDN comprises a CDN set forth in Table 3, Table 4, Table 5, Table 6, Table 7, or Table 8.

177. The complex of embodiment 176, wherein at least one CDN comprises a CDN set forth in Table 3.

178. The complex of embodiment 176 or embodiment 177, wherein at least one CDN comprises a CDN set forth in Table 4.

179. The complex of any one of embodiments 176 to 178, wherein at least one CDN comprises a CDN set forth in Table 5.

180. The complex of any one of embodiments 176 to 179, wherein at least one CDN comprises a CDN set forth in Table 6.

181. The complex of any one of embodiments 176 to 180, wherein at least one CDN comprises a CDN set forth in Table 7.

182. The complex of any one of embodiments 176 to 181, wherein at least one CDN comprises a CDN set forth in Table 8.

183. The complex of any one of embodiments 1 to 182, wherein the lipid binding proteins comprise apolipoprotein molecules.

184. The complex of embodiment 183, wherein the apolipoprotein molecules comprise ApoA-I, ApoA-II, ApoA-IV, ApoA-V, ApoB, ApoC-I, ApoC-II, ApoC-III, ApoD, ApoE, ApoJ, or ApoH molecules or a combination thereof.

185. The complex of embodiment 184, wherein the apolipoprotein molecules comprise or consist of ApoA-I molecules.

186. The complex of embodiment 185, wherein said ApoA-I molecules are human ApoA-I molecules.

187. The complex of embodiment 185 or embodiment 186, wherein said ApoA-I molecules are recombinant.

188. The complex of any one of embodiments 185 to 187, wherein the ApoA-I molecules are Apolipoprotein A-$I_{Milano}$ (ApoA-$I_M$), Apolipoprotein A-$I_{Paris}$ (ApoA-$I_P$), or Apolipoprotein A-$I_{Zaragoza}$ (ApoA-$I_Z$) molecules.

189. The complex of any one of embodiments 183 to 188, wherein at least one CDN binding moiety is coupled to an apolipoprotein molecule.

190. The complex of embodiment 189, wherein the CDN binding moiety is coupled to the apolipoprotein molecule by a direct bond.

191. The complex of embodiment 189, wherein the CDN binding moiety is coupled to the apolipoprotein molecule by a linker.

192. The complex of embodiment 191, wherein the linker coupling the apolipoprotein molecule to the CDN binding moiety is a bifunctional linker.

193. The complex of embodiment 191 or embodiment 192, wherein the linker coupling the apolipoprotein molecule to the CDN binding moiety is a cleavable linker.

194. The complex of embodiment 193, wherein the linker coupling the apolipoprotein molecule to the CDN binding moiety is a dipeptide linker.

195. The complex of embodiment 191 or embodiment 192, wherein the linker coupling the apolipoprotein molecule to the CDN binding moiety is a non-cleavable linker.

196. The complex of any one of embodiments 1 to 182, wherein the lipid binding protein molecules comprise apolipoprotein peptide mimetic molecules and optionally one or more apolipoprotein molecule such as those described in any one of embodiments 184 to 188.

197. The complex of embodiment 196, wherein the apolipoprotein peptide mimetic molecules comprise an ApoA-I peptide mimetic, ApoA-II peptide mimetic, ApoA-IV peptide mimetic, or ApoE peptide mimetic or a combination thereof.

198. The complex of any one of embodiments 196 to 197, wherein at least one CDN binding moiety is coupled to an apolipoprotein peptide mimetic molecule.

199. The complex of embodiment 198, wherein the CDN binding moiety is coupled to the apolipoprotein peptide mimetic molecule by a direct bond.

200. The complex of embodiment 198, wherein the CDN binding moiety is coupled to the apolipoprotein peptide mimetic molecule by a linker.

201. The complex of embodiment 200, wherein the linker coupling the apolipoprotein peptide mimetic molecule to the CDN binding moiety is a bifunctional linker.

202. The complex of embodiment 200 or embodiment 201, wherein the linker coupling the apolipoprotein peptide mimetic molecule to the CDN binding moiety is a cleavable linker.

203. The complex of embodiment 202, wherein the linker coupling the apolipoprotein peptide mimetic molecule to the CDN binding moiety is a dipeptide linker.

204. The complex of embodiment 202 or embodiment 203, wherein the linker coupling the apolipoprotein peptide mimetic molecule to the CDN binding moiety is a non-cleavable linker.

205. The complex of any one of embodiments 1 to 204, which comprises 1 to 8 ApoA-I equivalents.

206. The complex of embodiment 205, which comprises 1 to 8 apolipoprotein molecules.

207. The complex of embodiment 205, wherein the amphipathic molecules, the CDN binding moieties, the CDNs and, if present, the anchors and/or linkers together contribute a net charge of at least +1 or −1 per apolipoprotein molecule in the complex.

208. The complex of embodiment 206 or embodiment 207, wherein the apolipoprotein to amphipathic molecule molar ratio ranges from 8:1 to 1:15.

209. The complex of embodiment 206 or embodiment 207, wherein the apolipoprotein to amphipathic molecule molar ratio ranges from 7:1 to 1:15.

210. The complex of embodiment 206 or embodiment 207, wherein the apolipoprotein to amphipathic molecule molar ratio ranges from 6:1 to 1:15.

211. The complex of embodiment 206 or embodiment 207, wherein the apolipoprotein to amphipathic molecule molar ratio ranges from 5:1 to 1:15.

212. The complex of embodiment 206 or embodiment 207, wherein the apolipoprotein to amphipathic molecule molar ratio ranges from 4:1 to 1:15.

213. The complex of embodiment 206 or embodiment 207, wherein the apolipoprotein to amphipathic molecule molar ratio ranges from 3:1 to 1:15.

214. The complex of embodiment 206 or embodiment 207, wherein the apolipoprotein to amphipathic molecule molar ratio ranges from 2:1 to 1:15.

215. The complex of embodiment 206 or embodiment 207, wherein the apolipoprotein to amphipathic molecule molar ratio ranges from 1:1 to 1:15.

216. The complex of embodiment 206 or embodiment 207, wherein the apolipoprotein to amphipathic molecule molar ratio ranges from 8:1 to 1:14.

217. The complex of embodiment 206 or embodiment 207, wherein the apolipoprotein to amphipathic molecule molar ratio ranges from 7:1 to 1:14.

218. The complex of embodiment 206 or embodiment 207, wherein the apolipoprotein to amphipathic molecule molar ratio ranges from 6:1 to 1:14.

219. The complex of embodiment 206 or embodiment 207, wherein the apolipoprotein to amphipathic molecule molar ratio ranges from 5:1 to 1:14.

220. The complex of embodiment 206 or embodiment 207, wherein the apolipoprotein to amphipathic molecule molar ratio ranges from 4:1 to 1:14.

221. The complex of embodiment 206 or embodiment 207, wherein the apolipoprotein to amphipathic molecule molar ratio ranges from 3:1 to 1:14.

222. The complex of embodiment 206 or embodiment 207, wherein the apolipoprotein to amphipathic molecule molar ratio ranges from 2:1 to 1:14.

223. The complex of embodiment 206 or embodiment 207, wherein the apolipoprotein to amphipathic molecule molar ratio ranges from 1:1 to 1:14.

224. The complex of embodiment 206 or embodiment 207, wherein the apolipoprotein to amphipathic molecule molar ratio ranges from 8:1 to 1:13.

225. The complex of embodiment 206 or embodiment 207, wherein the apolipoprotein to amphipathic molecule molar ratio ranges from 7:1 to 1:13.

226. The complex of embodiment 206 or embodiment 207, wherein the apolipoprotein to amphipathic molecule molar ratio ranges from 6:1 to 1:13.

227. The complex of embodiment 206 or embodiment 207, wherein the apolipoprotein to amphipathic molecule molar ratio ranges from 5:1 to 1:13.

228. The complex of embodiment 206 or embodiment 207, wherein the apolipoprotein to amphipathic molecule molar ratio ranges from 4:1 to 1:13.

229. The complex of embodiment 206 or embodiment 207, wherein the apolipoprotein to amphipathic molecule molar ratio ranges from 3:1 to 1:13.

230. The complex of embodiment 206 or embodiment 207, wherein the apolipoprotein to amphipathic molecule molar ratio ranges from 2:1 to 1:13.

231. The complex of embodiment 206 or embodiment 207, wherein the apolipoprotein to amphipathic molecule molar ratio ranges from 1:1 to 1:13.

232. The complex of embodiment 206 or embodiment 207, wherein the apolipoprotein to amphipathic molecule molar ratio ranges from 8:1 to 1:12.

233. The complex of embodiment 206 or embodiment 207, wherein the apolipoprotein to amphipathic molecule molar ratio ranges from 7:1 to 1:12.

234. The complex of embodiment 206 or embodiment 207, wherein the apolipoprotein to amphipathic molecule molar ratio ranges from 6:1 to 1:12.

235. The complex of embodiment 206 or embodiment 207, wherein the apolipoprotein to amphipathic molecule molar ratio ranges from 5:1 to 1:12.

236. The complex of embodiment 206 or embodiment 207, wherein the apolipoprotein to amphipathic molecule molar ratio ranges from 4:1 to 1:12.

237. The complex of embodiment 206 or embodiment 207, wherein the apolipoprotein to amphipathic molecule molar ratio ranges from 3:1 to 1:12.

238. The complex of embodiment 206 or embodiment 207, wherein the apolipoprotein to amphipathic molecule molar ratio ranges from 2:1 to 1:12.

239. The complex of embodiment 206 or embodiment 207, wherein the apolipoprotein to amphipathic molecule molar ratio ranges from 1:1 to 1:12.

240. The complex of embodiment 206 or embodiment 207, wherein the apolipoprotein to amphipathic molecule molar ratio ranges from 8:1 to 1:11.

241. The complex of embodiment 206 or embodiment 207, wherein the apolipoprotein to amphipathic molecule molar ratio ranges from 7:1 to 1:11.

242. The complex of embodiment 206 or embodiment 207, wherein the apolipoprotein to amphipathic molecule molar ratio ranges from 6:1 to 1:11.

243. The complex of embodiment 206 or embodiment 207, wherein the apolipoprotein to amphipathic molecule molar ratio ranges from 5:1 to 1:11.

244. The complex of embodiment 206 or embodiment 207, wherein the apolipoprotein to amphipathic molecule molar ratio ranges from 4:1 to 1:11.

245. The complex of embodiment 206 or embodiment 207, wherein the apolipoprotein to amphipathic molecule molar ratio ranges from 3:1 to 1:11.

246. The complex of embodiment 206 or embodiment 207, wherein the apolipoprotein to amphipathic molecule molar ratio ranges from 2:1 to 1:11.

247. The complex of embodiment 206 or embodiment 207, wherein the apolipoprotein to amphipathic molecule molar ratio ranges from 1:1 to 1:11.

248. The complex of embodiment 206 or embodiment 207, wherein the apolipoprotein to amphipathic molecule molar ratio ranges from 8:1 to 1:10.

249. The complex of embodiment 206 or embodiment 207, wherein the apolipoprotein to amphipathic molecule molar ratio ranges from 7:1 to 1:10.

250. The complex of embodiment 206 or embodiment 207, wherein the apolipoprotein to amphipathic molecule molar ratio ranges from 6:1 to 1:10.

251. The complex of embodiment 206 or embodiment 207, wherein the apolipoprotein to amphipathic molecule molar ratio ranges from 5:1 to 1:10.

252. The complex of embodiment 206 or embodiment 207, wherein the apolipoprotein to amphipathic molecule molar ratio ranges from 4:1 to 1:10.

253. The complex of embodiment 206 or embodiment 207, wherein the apolipoprotein to amphipathic molecule molar ratio ranges from 3:1 to 1:10.

254. The complex of embodiment 206 or embodiment 207, wherein the apolipoprotein to amphipathic molecule molar ratio ranges from 2:1 to 1:10.

255. The complex of embodiment 206 or embodiment 207, wherein the apolipoprotein to amphipathic molecule molar ratio ranges from 1:1 to 1:10.

256. The complex of embodiment 206 or embodiment 207, wherein the apolipoprotein to amphipathic molecule molar ratio ranges from 8:1 to 1:9.

257. The complex of embodiment 206 or embodiment 207, wherein the apolipoprotein to amphipathic molecule molar ratio ranges from 7:1 to 1:9.

258. The complex of embodiment 206 or embodiment 207, wherein the apolipoprotein to amphipathic molecule molar ratio ranges from 6:1 to 1:9.

259. The complex of embodiment 206 or embodiment 207, wherein the apolipoprotein to amphipathic molecule molar ratio ranges from 5:1 to 1:9.

260. The complex of embodiment 206 or embodiment 207, wherein the apolipoprotein to amphipathic molecule molar ratio ranges from 4:1 to 1:9.

261. The complex of embodiment 206 or embodiment 207, wherein the apolipoprotein to amphipathic molecule molar ratio ranges from 3:1 to 1:9.

262. The complex of embodiment 206 or embodiment 207, wherein the apolipoprotein to amphipathic molecule molar ratio ranges from 2:1 to 1:9.

263. The complex of embodiment 206 or embodiment 207, wherein the apolipoprotein to amphipathic molecule molar ratio ranges from 1:1 to 1:9.

264. The complex of embodiment 206 or embodiment 207, wherein the apolipoprotein to amphipathic molecule molar ratio ranges from 8:1 to 1:8.

265. The complex of embodiment 206 or embodiment 207, wherein the apolipoprotein to amphipathic molecule molar ratio ranges from 7:1 to 1:8.

266. The complex of embodiment 206 or embodiment 207, wherein the apolipoprotein to amphipathic molecule molar ratio ranges from 6:1 to 1:8.

267. The complex of embodiment 206 or embodiment 207, wherein the apolipoprotein to amphipathic molecule molar ratio ranges from 5:1 to 1:8.

268. The complex of embodiment 206 or embodiment 207, wherein the apolipoprotein to amphipathic molecule molar ratio ranges from 4:1 to 1:8.

269. The complex of embodiment 206 or embodiment 207, wherein the apolipoprotein to amphipathic molecule molar ratio ranges from 3:1 to 1:8.

270. The complex of embodiment 206 or embodiment 207, wherein the apolipoprotein to amphipathic molecule molar ratio ranges from 2:1 to 1:8.

271. The complex of embodiment 206 or embodiment 207, wherein the apolipoprotein to amphipathic molecule molar ratio ranges from 1:1 to 1:8.

272. The complex of embodiment 206 or embodiment 207, wherein the apolipoprotein to amphipathic molecule molar ratio ranges from 8:1 to 1:7.

273. The complex of embodiment 206 or embodiment 207, wherein the apolipoprotein to amphipathic molecule molar ratio ranges from 7:1 to 1:7.

274. The complex of embodiment 206 or embodiment 207, wherein the apolipoprotein to amphipathic molecule molar ratio ranges from 6:1 to 1:7.

275. The complex of embodiment 206 or embodiment 207, wherein the apolipoprotein to amphipathic molecule molar ratio ranges from 5:1 to 1:7.

276. The complex of embodiment 206 or embodiment 207, wherein the apolipoprotein to amphipathic molecule molar ratio ranges from 4:1 to 1:7.

277. The complex of embodiment 206 or embodiment 207, wherein the apolipoprotein to amphipathic molecule molar ratio ranges from 3:1 to 1:7.

278. The complex of embodiment 206 or embodiment 207, wherein the apolipoprotein to amphipathic molecule molar ratio ranges from 2:1 to 1:7.

279. The complex of embodiment 206 or embodiment 207, wherein the apolipoprotein to amphipathic molecule molar ratio ranges from 1:1 to 1:7.

280. The complex of embodiment 206 or embodiment 207, wherein the apolipoprotein to amphipathic molecule molar ratio ranges from 8:1 to 1:6.

281. The complex of embodiment 206 or embodiment 207, wherein the apolipoprotein to amphipathic molecule molar ratio ranges from 7:1 to 1:6.

282. The complex of embodiment 206 or embodiment 207, wherein the apolipoprotein to amphipathic molecule molar ratio ranges from 6:1 to 1:6.

283. The complex of embodiment 206 or embodiment 207, wherein the apolipoprotein to amphipathic molecule molar ratio ranges from 5:1 to 1:6.

284. The complex of embodiment 206 or embodiment 207, wherein the apolipoprotein to amphipathic molecule molar ratio ranges from 4:1 to 1:6.

285. The complex of embodiment 206 or embodiment 207, wherein the apolipoprotein to amphipathic molecule molar ratio ranges from 3:1 to 1:6.

286. The complex of embodiment 206 or embodiment 207, wherein the apolipoprotein to amphipathic molecule molar ratio ranges from 2:1 to 1:6.

287. The complex of embodiment 206 or embodiment 207, wherein the apolipoprotein to amphipathic molecule molar ratio ranges from 1:1 to 1:6.

288. The complex of embodiment 206 or embodiment 207, wherein the apolipoprotein to amphipathic molecule molar ratio ranges from 8:1 to 1:5.

289. The complex of embodiment 206 or embodiment 207, wherein the apolipoprotein to amphipathic molecule molar ratio ranges from 7:1 to 1:5.

290. The complex of embodiment 206 or embodiment 207, wherein the apolipoprotein to amphipathic molecule molar ratio ranges from 6:1 to 1:5.

291. The complex of embodiment 206 or embodiment 207, wherein the apolipoprotein to amphipathic molecule molar ratio ranges from 5:1 to 1:5.

292. The complex of embodiment 206 or embodiment 207, wherein the apolipoprotein to amphipathic molecule molar ratio ranges from 4:1 to 1:5.

293. The complex of embodiment 206 or embodiment 207, wherein the apolipoprotein to amphipathic molecule molar ratio ranges from 3:1 to 1:5.

294. The complex of embodiment 206 or embodiment 207, wherein the apolipoprotein to amphipathic molecule molar ratio ranges from 2:1 to 1:5.

295. The complex of embodiment 206 or embodiment 207, wherein the apolipoprotein to amphipathic molecule molar ratio ranges from 1:1 to 1:5.

296. The complex of embodiment 206 or embodiment 207, wherein the apolipoprotein to amphipathic molecule molar ratio ranges from 8:1 to 1:4.

297. The complex of embodiment 206 or embodiment 207, wherein the apolipoprotein to amphipathic molecule molar ratio ranges from 7:1 to 1:4.

298. The complex of embodiment 206 or embodiment 207, wherein the apolipoprotein to amphipathic molecule molar ratio ranges from 6:1 to 1:4.

299. The complex of embodiment 206 or embodiment 207, wherein the apolipoprotein to amphipathic molecule molar ratio ranges from 5:1 to 1:4.

300. The complex of embodiment 206 or embodiment 207, wherein the apolipoprotein to amphipathic molecule molar ratio ranges from 4:1 to 1:4.

301. The complex of embodiment 206 or embodiment 207, wherein the apolipoprotein to amphipathic molecule molar ratio ranges from 3:1 to 1:4.

302. The complex of embodiment 206 or embodiment 207, wherein the apolipoprotein to amphipathic molecule molar ratio ranges from 2:1 to 1:4.

303. The complex of embodiment 206 or embodiment 207, wherein the apolipoprotein to amphipathic molecule molar ratio ranges from 1:1 to 1:4.

304. The complex of embodiment 206 or embodiment 207, wherein the apolipoprotein to amphipathic molecule molar ratio ranges from 8:1 to 1:3.

305. The complex of embodiment 206 or embodiment 207, wherein the apolipoprotein to amphipathic molecule molar ratio ranges from 7:1 to 1:3.

306. The complex of embodiment 206 or embodiment 207, wherein the apolipoprotein to amphipathic molecule molar ratio ranges from 6:1 to 1:3.

307. The complex of embodiment 206 or embodiment 207, wherein the apolipoprotein to amphipathic molecule molar ratio ranges from 5:1 to 1:3.

308. The complex of embodiment 206 or embodiment 207, wherein the apolipoprotein to amphipathic molecule molar ratio ranges from 4:1 to 1:3.

309. The complex of embodiment 206 or embodiment 207, wherein the apolipoprotein to amphipathic molecule molar ratio ranges from 3:1 to 1:3.

310. The complex of embodiment 206 or embodiment 207, wherein the apolipoprotein to amphipathic molecule molar ratio ranges from 2:1 to 1:3.

311. The complex of embodiment 206 or embodiment 207, wherein the apolipoprotein to amphipathic molecule molar ratio ranges from 1:1 to 1:3.

312. The complex of embodiment 206 or embodiment 207, wherein the apolipoprotein to amphipathic molecule molar ratio ranges from 8:1 to 1:2.

313. The complex of embodiment 206 or embodiment 207, wherein the apolipoprotein to amphipathic molecule molar ratio ranges from 7:1 to 1:2.

314. The complex of embodiment 206 or embodiment 207, wherein the apolipoprotein to amphipathic molecule molar ratio ranges from 6:1 to 1:2.

315. The complex of embodiment 206 or embodiment 207, wherein the apolipoprotein to amphipathic molecule molar ratio ranges from 5:1 to 1:2.

316. The complex of embodiment 206 or embodiment 207, wherein the apolipoprotein to amphipathic molecule molar ratio ranges from 4:1 to 1:2.

317. The complex of embodiment 206 or embodiment 207, wherein the apolipoprotein to amphipathic molecule molar ratio ranges from 3:1 to 1:2.

318. The complex of embodiment 206 or embodiment 207, wherein the apolipoprotein to amphipathic molecule molar ratio ranges from 2:1 to 1:2.

319. The complex of embodiment 206 or embodiment 207, wherein the apolipoprotein to amphipathic molecule molar ratio ranges from 1:1 to 1:2.

320. The complex of embodiment 206 or embodiment 207, wherein the apolipoprotein to amphipathic molecule molar ratio ranges from 8:1 to 1:1.

321. The complex of embodiment 206 or embodiment 207, wherein the apolipoprotein to amphipathic molecule molar ratio ranges from 7:1 to 1:1.

322. The complex of embodiment 206 or embodiment 207, wherein the apolipoprotein to amphipathic molecule molar ratio ranges from 6:1 to 1:1.

323. The complex of embodiment 206 or embodiment 207, wherein the apolipoprotein to amphipathic molecule molar ratio ranges from 5:1 to 1:1.

324. The complex of embodiment 206 or embodiment 207, wherein the apolipoprotein to amphipathic molecule molar ratio ranges from 4:1 to 1:1.

325. The complex of embodiment 206 or embodiment 207, wherein the apolipoprotein to amphipathic molecule molar ratio ranges from 3:1 to 1:1.

326. The complex of embodiment 206 or embodiment 207, wherein the apolipoprotein to amphipathic molecule molar ratio ranges from 2:1 to 1:1.

327. The complex of embodiment 206 or embodiment 207, wherein the apolipoprotein to amphipathic molecule molar ratio ranges from 1.5:1 to 1:2.

328. The complex of embodiment 206 or embodiment 207, wherein the apolipoprotein to amphipathic molecule molar ratio ranges from 5:4 to 4:5.

329. The complex of embodiment 206 or embodiment 207, wherein the apolipoprotein to amphipathic molecule molar ratio ranges from 5:3 to 3:5.

330. The complex of embodiment 206 or embodiment 207, wherein the apolipoprotein to amphipathic molecule molar ratio ranges from 5:2 to 2:5.

331. The complex of embodiment 206 or embodiment 207, wherein the apolipoprotein to amphipathic molecule molar ratio ranges from 3:2 to 2:3.

332. The complex of any one of embodiments 206 to 331, which comprises 1 apolipoprotein molecule.

333. The complex of any one of embodiments 206 to 331, which comprises 2 apolipoprotein molecules.

334. The complex of embodiment 333 which has a Stokes radius of 3 nm or less.

335. The complex of embodiment 333 or embodiment 334 which comprises 2 apolipoprotein molecules and 1, 2 or 3 negatively charged phospholipid molecules per apolipoprotein molecule.

336. The complex of any one of embodiments 206 to 331, which comprises 4 apolipoprotein molecules.

337. The complex of embodiment 336, which has a Stokes radius of 4 nm or less.

338. The complex of embodiment 336 or embodiment 337, which comprises 4 apolipoprotein molecules and 1, 2 or 3 negatively charged phospholipid molecules per apolipoprotein molecule.

339. The complex of any one of embodiments 206 to 331, which comprises 8 apolipoprotein molecules.

340. The complex of embodiment 339, which has a Stokes radius of 5 nm or less.

341. The complex of embodiment 339 or embodiment 340, which comprises 8 apolipoprotein molecules and 1, 2 or 3 negatively charged phospholipid molecules per apolipoprotein molecule.

342. The complex of any one of embodiments 1 to 341, wherein the amphipathic molecules comprise a phospholipid, a detergent, a fatty acid, an apolar moiety or sterol covalently attached to a sugar, or a combination thereof.

343. The complex of embodiment 342, wherein the apolar moiety is an acyl or a diacyl chain.

344. The complex of embodiment 342 or embodiment 343, wherein the sugar is a modified sugar or a substituted sugar.

345. The complex of embodiment 342, wherein the amphipathic molecules comprise or consist of phospholipid molecules.

346. The complex of embodiment 345, wherein the phospholipid molecules comprise negatively charged phospholipids, neutral phospholipids, positively charged phospholipids or a combination thereof.

347. The complex of embodiment 346, wherein the phospholipid molecules contribute a net charge of 1-3 per apolipoprotein molecule in the complex.

348. The complex of embodiment 347, wherein the net charge is a negative net charge.

349. The complex of embodiment 347, wherein the net charge is a positive net charge.

350. The complex of any one of embodiments 346 to 348, wherein the phospholipid molecules consist of a combination of negatively charged and neutral phospholipids.

351. The complex of embodiment 350, wherein the molar ratio of negatively charge phospholipid to neutral phospholipid ranges from 1:1 to 1:3.

352. The complex of embodiment 351, wherein the molar ratio of negatively charged phospholipid to neutral phospholipid is about 1:1 or about 1:2.

353. The complex of any one of embodiments 342 to 352, wherein at least one of the amphipathic molecules is an anchor.

354. The complex of embodiment 353, wherein the at least one of the amphipathic molecules which is an anchor is coupled to one of the CDN binding moieties by a direct bond.

355. The complex of embodiment 353, wherein the at least one of the amphipathic molecules which is an anchor is coupled to one of the CDN binding moieties by a linker.

356. The complex of embodiment 355, wherein the linker coupling the amphipathic molecule(s) to the CDN binding moiety is a bifunctional linker.

357. The complex of embodiment 355 or embodiment 356, wherein the linker coupling the amphipathic molecule(s) to the CDN binding moiety is a cleavable linker.

358. The complex of embodiment 357, wherein the linker coupling the amphipathic molecule(s) to the CDN binding moiety is a dipeptide linker.

359. The complex of embodiment 355 or embodiment 356, wherein the linker coupling the amphipathic molecule(s) to the CDN binding moiety is a non-cleavable linker.

360. The complex of any one of embodiments 183 to 207, wherein the amphipathic molecules comprise neutral phospholipids.

361. The complex of embodiment 360, wherein the amphipathic molecules comprise neutral lipids and negatively charged phospholipids.

362. The complex of embodiment 361, wherein the amphipathic molecules comprise neutral lipids and negatively charged phospholipids in a weight ratio of 95:5 to 99:1.

363. The complex of embodiment 361 or embodiment 362, wherein the negatively charged phospholipids comprise a phosphatidylinositol, a phosphatidylserine, a phosphatidylglycerol, a phosphatidic acid, or a salt thereof, optionally wherein the salt is a sodium salt or a potassium salt.

364. The complex of embodiment 363, wherein the negatively charged phospholipids comprise a phosphatidylglycerol, a phosphatidylinositol, or a salt thereof.

365. The complex of embodiment 364, wherein the negatively charged phospholipid comprises 1,2-dipalmitoyl-sn-glycero-3-[phospho-rac-(1-glycerol)] (DPPG) or a salt thereof.

366. The complex of any one of embodiments 360 to 365, wherein the neutral phospholipid comprises a lecithin and/or a sphingomyelin.

367. The complex of embodiment 366, wherein the neutral lipid comprises a sphingomyelin.

368. The complex of embodiment 367, wherein the sphingomyelin is egg sphingomyelin, a plant sphingomyelin, or a synthetic sphingomyelin.

369. The complex of any one of embodiments 360 to 368, wherein apolipoprotein to phospholipid ratio is in the range of about 1:2 to about 1:3 by weight.

370. The complex of embodiment 369, wherein the apolipoprotein to phospholipid ratio is 1:2.7 by weight.

371. The complex of any one of embodiments 360 to 370, wherein at least one of the phospholipid molecules is an anchor.

372. The complex of embodiment 371, wherein the at least one of the phospholipid molecules which is an anchor is coupled to one of the CDN binding moieties by a direct bond.

373. The complex of embodiment 371, wherein the at least one of the phospholipid molecules which is an anchor is coupled to one of the CDN binding moieties by a linker.

374. The complex of embodiment 373, wherein the linker coupling the phospholipid molecule(s) to the CDN binding moiety is a bifunctional linker.

375. The complex of embodiment 373 or embodiment 374, wherein the linker coupling the phospholipid molecule(s) to the CDN binding moiety is a cleavable linker.

376. The complex of embodiment 375, wherein the linker coupling the phospholipid molecule(s) to the CDN binding moiety is a dipeptide linker.

377. The complex of embodiment 373 or embodiment 374, wherein the linker coupling the phospholipid molecule(s) to the CDN binding moiety is a non-cleavable linker.

378. The complex of any one of embodiments 371 to 377, wherein the at least one phospholipid molecule which is an anchor is a negatively charged phospholipid molecule.

379. The complex of any one of embodiments 371 to 377, wherein the at least one phospholipid molecule which is an anchor is a neutral phospholipid molecule.

380. A pharmaceutical composition comprising the complex of any one of embodiments 1 to 379 and one or more pharmaceutically acceptable carriers, diluents, excipients, or combination thereof.

381. A method of producing the complex of any one of embodiments 1 to 379, comprising combining a CDN-free complex comprising the lipid binding protein molecules, the CDN binding moieties, the amphipathic molecules if present and, if present, the anchors and/or linkers with the CDNs.

382. The method of embodiment 381, further comprising a step of making the CDN-free complex.

383. The method of embodiment 381 or embodiment 382, further comprising a mixing step after combining the CDN-free complex and the CDNs.

384. A method of producing the complex of any one of embodiments 1 to 379, comprising pre-complexing the CDN with the CDN binding moiety and, subsequently combining the pre-complexed CDN and CDN binding moiety with the lipid binding protein molecules and, if present, the amphipathic molecules and the anchors and/or linkers with the CDNs.

385. A method of administering a CDN to a subject comprising administering an amount of the complex of any one of embodiments 1 to 379 or the pharmaceutical composition of embodiment 380 to the subject.

386. A method of treating a subject, comprising administering to a subject in need thereof a therapeutically effective amount of the complex of any one of embodiments 1 to 379 or the pharmaceutical composition of embodiment 380 to the subject.

387. A method of treating a subject afflicted with a disease or condition associated with or modulated by STING comprising administering to a subject in need thereof a therapeutically effective amount of the complex of any one of embodiments 1 to 379 or the pharmaceutical composition of embodiment 380 to the subject.

388. A method of inducing an immune response in a subject, comprising administering to a subject in need thereof a therapeutically effective amount of the complex of any one of embodiments 1 to 379 or the pharmaceutical composition of embodiment 380 to the subject.

389. A method of treating a subject afflicted with cancer, comprising administering a therapeutically effective amount of the complex of any one of embodiments 1 to 379 or the pharmaceutical composition of embodiment 380 to the subject.

390. The method of embodiment 389, wherein the subject has a tumor.

391. The method of embodiment 390, wherein the tumor is stage T1 or higher according to according to the TNM classification system.

392. The method of embodiment 391, wherein the tumor is stage T1 according to according to the TNM classification system.

393. The method of embodiment 391, wherein the tumor is stage T2 or higher according to according to the TNM classification system.

394. The method of embodiment 391, wherein the tumor is stage T2 according to according to the TNM classification system.

395. The method of embodiment 391, wherein the tumor is stage T3 or higher according to according to the TNM classification system.

396. The method of embodiment 391, wherein the tumor is stage T3 according to according to the TNM classification system.

397. The method of embodiment 391, wherein the tumor is stage T4 according to according to the TNM classification system.

398. The method of any one of embodiments 390 to 397, wherein the tumor is a primary tumor.

399. The method of any one of embodiments 390 to 397, wherein the tumor is a secondary tumor.

400. The method of any one of embodiments 390 to 399, wherein cells in the tumor overexpress or are suspected of overexpressing scavenger receptor B1 (SR-B1).

401. The method of embodiment 400, wherein cells in the tumor overexpress SR-B1.

402. The method of embodiment 401, wherein the cells in the tumor that overexpress SR-B1 comprise tumor associated macrophages (TAMs).

403. The method of embodiment 401 or embodiment 402, wherein the cells in the tumor that overexpress SR-B1 comprise cancer cells.

404. The method of any one of embodiments 390 to 401, wherein cells in the tumor express or overexpress KRAS.

405. The method of embodiment 404, wherein the KRAS has one or more mutations.

406. The method of any one of embodiments 390 to 405, wherein cells in the tumor express or overexpress nerve growth factor (NGF).

407. The method of embodiment 406, wherein the NGF has one or more mutations.

408. The method of any one of embodiments 390 to 407, wherein cells in the tumor express or overexpress signal transducer and activator of transcription 3 (STAT3).

409. The method of embodiment 408, wherein the STAT3 has one or more mutations.

410. The method of any one of embodiments 390 to 409, wherein cells in the tumor express or overexpress Hungtintin.

411. The method of embodiment 410, wherein the Huntingtin has one or more mutations.

412. The method of any one of embodiments 390 to 411, wherein the tumor is an esophageal tumor, a breast tumor, an ovarian tumor, a prostate tumor, a lung tumor, a kidney tumor, a gastric tumor, a colon tumor, a testicular tumor, a head and neck tumor, a pancreas tumor, a bladder tumor, a thyroid tumor or a brain tumor. 413. The method of embodiment 412, wherein the tumor is an esophageal tumor.

414. The method of embodiment 412, wherein the tumor is a breast tumor. 415. The method of embodiment 412, wherein the tumor is an ovarian tumor.

416. The method of embodiment 412, wherein the tumor is a prostate tumor.

417. The method of embodiment 412, wherein the tumor is a lung tumor. 418. The method of embodiment 412, wherein the tumor is a kidney tumor.

419. The method of embodiment 412, wherein the tumor is a gastric tumor.

420. The method of embodiment 412, wherein the tumor is a colon tumor. 421. The method of embodiment 412, wherein the tumor is a testicular tumor.

422. The method of embodiment 412, wherein the tumor is a head and neck tumor.

423. The method of embodiment 412, wherein the tumor is a pancreas tumor.

424. The method of embodiment 412, wherein the tumor is a bladder tumor.

425. The method of embodiment 412, wherein the tumor is a thyroid tumor.

426. The method of embodiment 412, wherein the tumor is a brain tumor.

427. The method of any one of embodiments 389 to 426, wherein the subject is afflicted with acute myeloid leukemia, adrenal cancer, anal cancer, basal cell skin cancer, squamous cell skin cancer bile duct cancer, bladder cancer, bone cancer, brain cancer, breast cancer, castleman disease, cervical cancer, chronic lymphocytic leukemia, chronic myeloid leukemia, chronic myelomonocytic leukemia, colorectal cancer, endometrial cancer, esophageal cancer, ewing sarcoma, eye cancer, gallbladder cancer, gastrointestinal cancer, hodgkin lymphoma, kaposi sarcoma, kidney cancer, laryngeal cancer, hypopharyngeal cancer, leukemia, liver cancer, lung cancer, lymphoma, malignant mesothelioma, melanoma skin cancer, merkel cell skin cancer, multiple myeloma, myelodysplastic syndromes, nasal cavity cancer, paranasal sinuses cancer, nasopharyngeal cancer, neuroblastoma, non-hodgkin lymphoma, non-small cell lung cancer, oral cavity cancer, oropharyngeal cancer, osteosarcoma, ovarian cancer, pancreatic cancer, penile cancer, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer, uterine sarcoma, vaginal cancer, vulvar cancer, or waldenstrom macroglobulinemia.

428. The method of embodiment 427, wherein the subject is afflicted with acute myeloid leukemia.

429. The method of embodiment 427, wherein the subject is afflicted with adrenal cancer.

430. The method of embodiment 427, wherein the subject is afflicted with anal cancer.

431. The method of embodiment 427, wherein the subject is afflicted with basal cell skin cancer.

432. The method of embodiment 427, wherein the subject is afflicted with squamous cell skin cancer.

433. The method of embodiment 427, wherein the subject is afflicted with bile duct cancer.

434. The method of embodiment 427, wherein the subject is afflicted with bladder cancer.

435. The method of embodiment 427, wherein the subject is afflicted with bone cancer.

436. The method of embodiment 427, wherein the subject is afflicted with brain cancer.

437. The method of embodiment 427, wherein the subject is afflicted with breast cancer.

438. The method of embodiment 427, wherein the subject is afflicted with castleman disease.

439. The method of embodiment 427, wherein the subject is afflicted with cervical cancer.

440. The method of embodiment 427, wherein the subject is afflicted with chronic lymphocytic leukemia.

441. The method of embodiment 427, wherein the subject is afflicted with chronic myeloid leukemia.

442. The method of embodiment 427, wherein the subject is afflicted with chronic myelomonocytic leukemia.

443. The method of embodiment 427, wherein the subject is afflicted with colorectal cancer.

444. The method of embodiment 427, wherein the subject is afflicted with endometrial cancer.

445. The method of embodiment 427, wherein the subject is afflicted with esophageal cancer.

446. The method of embodiment 427, wherein the subject is afflicted with ewing sarcoma.

447. The method of embodiment 427, wherein the subject is afflicted with eye cancer.

448. The method of embodiment 427, wherein the subject is afflicted with gallbladder cancer.

449. The method of embodiment 427, wherein the subject is afflicted with gastrointestinal cancer.

450. The method of embodiment 427, wherein the subject is afflicted with hodgkin lymphoma.

451. The method of embodiment 427, wherein the subject is afflicted with kaposi sarcoma.

452. The method of embodiment 427, wherein the subject is afflicted with kidney cancer.

453. The method of embodiment 427, wherein the subject is afflicted with laryngeal cancer.

454. The method of embodiment 427, wherein the subject is afflicted with hypopharyngeal cancer.

455. The method of embodiment 427, wherein the subject is afflicted with leukemia.

456. The method of embodiment 427, wherein the subject is afflicted with liver cancer.

457. The method of embodiment 427, wherein the subject is afflicted with lung cancer.

458. The method of embodiment 427, wherein the subject is afflicted with lymphoma.

459. The method of embodiment 427, wherein the subject is afflicted with malignant mesothelioma.

460. The method of embodiment 427, wherein the subject is afflicted with melanoma skin cancer.

461. The method of embodiment 427, wherein the subject is afflicted with merkel cell skin cancer.

462. The method of embodiment 427, wherein the subject is afflicted with multiple myeloma.

463. The method of embodiment 427, wherein the subject is afflicted with myelodysplastic syndromes.

464. The method of embodiment 427, wherein the subject is afflicted with nasal cavity cancer.

465. The method of embodiment 427, wherein the subject is afflicted with paranasal sinuses cancer.

466. The method of embodiment 427, wherein the subject is afflicted with nasopharyngeal cancer.

467. The method of embodiment 427, wherein the subject is afflicted with neuroblastoma.

468. The method of embodiment 427, wherein the subject is afflicted with non-hodgkin lymphoma.

469. The method of embodiment 427, wherein the subject is afflicted with non-small cell lung cancer.

470. The method of embodiment 427, wherein the subject is afflicted with oral cavity cancer 471. The method of embodiment 427, wherein the subject is afflicted with oropharyngeal cancer.

472. The method of embodiment 427, wherein the subject is afflicted with osteosarcoma.

473. The method of embodiment 427, wherein the subject is afflicted with ovarian cancer.

474. The method of embodiment 427, wherein the subject is afflicted with pancreatic cancer.

475. The method of embodiment 427, wherein the subject is afflicted with penile cancer.

476. The method of embodiment 427, wherein the subject is afflicted with prostate cancer.

477. The method of embodiment 427, wherein the subject is afflicted with retinoblastoma.

478. The method of embodiment 427, wherein the subject is afflicted with rhabdomyosarcoma.

479. The method of embodiment 427, wherein the subject is afflicted with salivary gland cancer.

480. The method of embodiment 427, wherein the subject is afflicted with skin cancer.

481. The method of embodiment 427, wherein the subject is afflicted with small cell lung cancer.

482. The method of embodiment 427, wherein the subject is afflicted with small intestine cancer.

483. The method of embodiment 427, wherein the subject is afflicted with soft tissue sarcoma.

484. The method of embodiment 427, wherein the subject is afflicted with stomach cancer.

485. The method of embodiment 427, wherein the subject is afflicted with testicular cancer.

486. The method of embodiment 427, wherein the subject is afflicted with thymus cancer.

487. The method of embodiment 427, wherein the subject is afflicted with thyroid cancer.

488. The method of embodiment 427, wherein the subject is afflicted with uterine sarcoma.

489. The method of embodiment 427, wherein the subject is afflicted with vaginal cancer.

490. The method of embodiment 427, wherein the subject is afflicted with vulvar cancer.

491. The method of embodiment 427, wherein the subject is afflicted with waldenstrom macroglobulinemia.

492. The method of any one of embodiments 389 to 491, wherein administration of the complex is before and/or after surgery to remove a tumor from the subject.

493. The method of any one of embodiments 389 to 492, further comprising administering a an anti-cancer therapy to the subject.

494. The method of embodiment 493, wherein the anti-cancer therapy comprises radiation.

495. The method of embodiment 493 or embodiment 494, wherein the anti-cancer therapy comprises an anti-cancer agent.

496. The method of embodiment 495, wherein the anti-cancer agent comprises an antibody, a topoisomerase inhibitor, a DNA alkylating agent, a DNA strand break inducing agent, an anti-microtubule agent, an anti-metabolic agent, an anthracycline, a *vinca* alkaloid, or an epipodophyllotoxin, a tyrosine kinase inhibitor, a CDK inhibitor, a MAP kinase inhibitor, an EGFR inhibitor, a VEGF inhibitor, an immunotherapy agent, a checkpoint inhibitor, a neo-antigen, a siRNA, an antisense oligonucleotide, or a combination thereof.

497. The method of embodiment 496, wherein the anti-cancer agent comprises an antibody.

498. The method of embodiment 496, wherein the anti-cancer agent comprises a topoisomerase inhibitor.

499. The method of embodiment 496, wherein the anti-cancer agent comprises a DNA alkylating agent.

500. The method of embodiment 496, wherein the anti-cancer agent comprises a DNA strand break inducing agent.

501. The method of embodiment 496, wherein the anti-cancer agent comprises an anti-microtubule agent.

502. The method of embodiment 496, wherein the anti-cancer agent comprises an anti-metabolic agent.

503. The method of embodiment 496, wherein the anti-cancer agent comprises an anthracycline.

504. The method of embodiment 496, wherein the anti-cancer agent comprises a *vinca* alkaloid.

505. The method of embodiment 496, wherein the anti-cancer agent comprises an epipodophyllotoxin.

506. The method of embodiment 496, wherein the anti-cancer agent comprises a tyrosine kinase inhibitor.

507. The method of embodiment 496, wherein the anti-cancer agent comprises a CDK inhibitor.

508. The method of embodiment 496, wherein the anti-cancer agent comprises a MAP kinase inhibitor.

509. The method of embodiment 496, wherein the anti-cancer agent comprises an EGFR inhibitor.

510. The method of embodiment 496, wherein the anti-cancer agent comprises a VEGF inhibitor.

511. The method of embodiment 496, wherein the anti-cancer agent comprises an immunotherapy agent.

512. The method of embodiment 496, wherein the anti-cancer agent comprises a checkpoint inhibitor.

513. The method of embodiment 496, wherein the anti-cancer agent comprises a neo-antigen.

514. The method of embodiment 496, wherein the anti-cancer agent comprises a siRNA.

515. The method of embodiment 496, wherein the anti-cancer agent comprises an antisense oligonucleotide.

516. The method of any one of embodiments 496 to 515, wherein the anti-cancer agent is in the form of an antibody-drug conjugate (ADC).

517. The method of any one of embodiments 496 to 515, wherein the anti-cancer agent is in the form of a lipoprotein complex comprising the anti-cancer agent.

518. The method of embodiment 517, wherein the lipoprotein complex comprising the anti-cancer agent comprises CER-001, CSL-111, CSL-112, or ETC-216.

519. The method of embodiment 518, wherein the lipoprotein complex comprising an anti-cancer agent comprises CER-001.

520. The method of embodiment 518, wherein the lipoprotein complex comprising an anti-cancer agent comprises CSL-111.

521. The method of embodiment 518, wherein the lipoprotein complex comprising an anti-cancer agent comprises CSL-112.

522. The method of embodiment 518, wherein the lipoprotein complex comprising an anti-cancer agent comprises ETC-216.

523. A method of treating an infection or infectious disease in a subject, comprising administering to a subject in need thereof a therapeutically effective amount of the complex of any one of embodiments 1 to 379 or the pharmaceutical composition of embodiment 380 to the subject.

524. The method of embodiment 523, further comprising administering an anti-infective agent so the subject.

525. The method of embodiment 524, wherein the anti-infective agent comprises an anti-bacterial agent, an anti-viral agent, an anti-parasitic agent, an anti-fungal agent, or an anti-mycobacterial agent.

526. The method of embodiment 525, wherein the anti-infective agent comprises an anti-bacterial agent, optionally wherein the anti-bacterial agent is a β-lactam antibiotic, a penicillin, a cephalosporin, a β-lactamase inhibitor, vancomycin, an aminoglycoside, a tetracycline, chloramphenicol, erythromycin, lincomycin, clindamycin, rifampin, metronidazole, a polymyxin, a sulfonamide, or a quinoline.

527. The method of embodiment 525, wherein the anti-infective agent comprises an anti-viral agent, optionally wherein the anti-viral agent is amantadine, rimantadine, ribivarin, acyclovir, vidarabine, trifluorothymidine, ganciclovir, zidovudine, retinovir, or an interferon.

528. The method of embodiment 525, wherein the anti-infective agent comprises an anti-fungal agent, optionally wherein the anti-fungal agent is an imidazole, a triazoles, a polyene macrolide antibiotic, griseofulvin, amphotericin B, or flucytosine.

529. The method of embodiment 525, wherein the anti-infective agent comprises an anti-parasitic agent.

While various specific embodiments have been illustrated and described, it will be appreciated that various changes can be made without departing from the spirit and scope of the disclosure(s).

9. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A complex for carrying one or more cyclic dinucleotides (CDNs), consisting of:
   (a) one or more lipid binding protein molecules selected from apolipoprotein molecules;
   (b) one or more CDNs;
   (c) one or more CDN binding moieties that (i) non-covalently bind the one or more CDNs and (ii) indirectly couple the one or more CDNs to the one or more lipid binding protein molecules;
   (d) optionally, an amount of amphipathic molecules sufficient to solubilize the lipid binding protein molecules; and
   (e) optionally, one or more anchors non-covalently coupling one or more CDN binding moieties to the lipid binding protein molecules; or
   (f) optionally, one or more linkers covalently coupling one or more CDN binding moieties to one or more lipid binding protein molecules, one or more amphipathic molecules or one or more anchors.

2. The complex of claim 1, wherein the complex contains amphipathic molecules.

3. The complex of claim 1, wherein the CDN binding moiety is positively charged at physiological pH.

4. The complex of claim 1, wherein the CDN binding moiety is a positively charged peptide.

5. The complex of claim 4, wherein the positively charged peptide contains lysine residues, arginine residues, ornithine residues, histidine residues, or a combination thereof.

6. The complex of claim 1, wherein the CDN binding moiety is a loop forming oligonucleotide (LFO).

7. The complex of claim 6, wherein the LFO is 20 to 150 nucleotides in length.

8. The complex of claim 6, wherein the LFO is a riboswitch or a loop forming portion thereof.

9. The complex of claim 1, wherein at least one CDN binding moiety is coupled to an anchor.

10. The complex of claim 1, wherein at least one CDN binding moiety is coupled to the one or more lipid binding protein molecules.

11. The complex of claim 1, wherein at least one CDN is a naturally occurring CDN.

12. The complex of claim 1, wherein at least one CDN is a non-naturally occurring CDN.

13. The complex of claim 1, wherein the apolipoprotein molecules are selected from ApoA-I, ApoA-II, ApoA-IV, ApoA-V, ApoB, ApoC-I, ApoC-II, ApoC-III, ApoD, ApoE, ApoJ, or ApoH molecules or a combination thereof.

14. A pharmaceutical composition comprising the complex of claim 1 and one or more pharmaceutically acceptable carriers, diluents, excipients, or a combination of distinct agents thereof.

15. A method of administering a CDN to a subject in need thereof comprising administering to the subject an amount of the complex of claim 1.

16. A method of treating a subject afflicted with a disease or condition modulated by stimulator of interferon gene (STING), comprising administering to the subject a therapeutically effective amount of the complex of claim 1.

17. A method of inducing an immune response in a subject in need thereof, comprising administering to the subject a therapeutically effective amount of the complex of claim 1.

18. A method of treating a subject afflicted with cancer modulated by stimulator of interferon gene (STING), comprising administering to the subject a therapeutically effective amount of the complex of claim 1.

19. A method of treating a subject having an infection or infectious disease modulated by stimulator of interferon gene (STING), comprising administering to the subject a therapeutically effective amount of the complex of claim 1.

* * * * *